US012279994B2

(12) United States Patent
Augustine et al.

(10) Patent No.: US 12,279,994 B2
(45) Date of Patent: *Apr. 22, 2025

(54) RELOCATION MODULE AND METHODS FOR SURGICAL EQUIPMENT

(71) Applicant: Augustine Biomedical + Design, LLC, Eden Prairie, MN (US)

(72) Inventors: Scott D. Augustine, Deephaven, MN (US); Susan D. Augustine, Deephaven, MN (US); Garrett J. Augustine, Deephaven, MN (US); Brent M. Augustine, Savage, MN (US); Ryan S. Augustine, Minneapolis, MN (US); Randall C. Arnold, Minnetonka, MN (US)

(73) Assignee: Augustine Biomedical + Design, LLC, Eden Prairie, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 18/943,055

(22) Filed: Nov. 11, 2024

(65) Prior Publication Data

US 2025/0064660 A1   Feb. 27, 2025

Related U.S. Application Data

(63) Continuation of application No. 18/598,110, filed on Mar. 7, 2024, now Pat. No. 12,178,759, which is a
(Continued)

(51) Int. Cl.
*A61G 13/10* (2006.01)
*A61B 46/10* (2016.01)
(Continued)

(52) U.S. Cl.
CPC ............ *A61G 13/108* (2013.01); *A61B 50/13* (2016.02); *A61B 50/15* (2016.02); *A61M 16/06* (2013.01);
(Continued)

(58) Field of Classification Search
CPC ...... A61G 13/108; A61B 50/13; A61B 50/15; A61B 46/10; A61B 90/50;
(Continued)

(56) References Cited

U.S. PATENT DOCUMENTS

| 4,105,028 A | 8/1978 | Sadlier et al. |
| 4,531,956 A | 7/1985 | Howorth |

(Continued)

FOREIGN PATENT DOCUMENTS

| CN | 101980732 A | 2/2011 |
| CN | 109934097 A | 6/2019 |
| EP | 3103385 A1 | 12/2016 |
| WO | WO-2016025989 A1 | 2/2016 |

(Continued)

OTHER PUBLICATIONS

U.S. Appl. No. 15/935,524 U.S. Pat. No. 10,512,191, Mar. 26, 2018, Relocation Module for Patient Monitors and Surgical Equipment.
(Continued)

*Primary Examiner* — Kathleen Y Dulaney

(74) *Attorney, Agent, or Firm* — Schwegman Lundberg & Woessner, P.A.

(57) ABSTRACT

Module for housing electronic and electromechanical medical equipment including a portable digital camera and processing circuitry with machine vision and machine learning software for automatically documenting healthcare events and healthcare equipment operations in the electronic health record.

38 Claims, 36 Drawing Sheets

Related U.S. Application Data continuation of application No. 18/142,787, filed on May 3, 2023, now Pat. No. 12,023,281, which is a continuation of application No. 18/099,074, filed on Jan. 19, 2023, now abandoned, which is a continuation of application No. 17/874,963, filed on Jul. 27, 2022, now Pat. No. 11,648,166, which is a continuation of application No. 17/873,857, filed on Jul. 26, 2022, now Pat. No. 11,654,070, which is a continuation of application No. 17/528,832, filed on Nov. 17, 2021, now Pat. No. 11,432,982, which is a continuation-in-part of application No. 17/376,469, filed on Jul. 15, 2021, now Pat. No. 11,219,570, and a continuation-in-part of application No. 17/245,942, filed on Apr. 30, 2021, now Pat. No. 11,426,318, application No. 18/943,055 is a continuation-in-part of application No. 17/245,942, filed on Apr. 30, 2021, now Pat. No. 11,426,318, said application No. 17/376,469 is a continuation-in-part of application No. 17/199,722, filed on Mar. 12, 2021, now Pat. No. 11,173,089, said application No. 17/245,942 is a continuation-in-part of application No. 17/167,681, filed on Feb. 4, 2021, now Pat. No. 11,160,710, said application No. 17/199,722 is a continuation of application No. 17/092,681, filed on Nov. 9, 2020, now Pat. No. 10,993,865, said application No. 17/167,681 is a continuation-in-part of application No. 17/092,681, filed on Nov. 9, 2020, now Pat. No. 10,993,865, which is a continuation of application No. 16/879,406, filed on May 20, 2020, now Pat. No. 10,869,800, which is a continuation-in-part of application No. 16/601,924, filed on Oct. 15, 2019, now Pat. No. 10,702,436, which is a continuation of application No. 16/593,033, filed on Oct. 4, 2019, now Pat. No. 10,653,577, which is a continuation of application No. 16/364,884, filed on Mar. 26, 2019, now Pat. No. 10,507,153, which is a continuation-in-part of application No. 15/935,524, filed on Mar. 26, 2018, now Pat. No. 10,512,191.

(60) Provisional application No. 62/782,901, filed on Dec. 20, 2018.

(51) Int. Cl.
| | | |
|---|---|---|
| *A61B 50/13* | (2016.01) | |
| *A61B 50/15* | (2016.01) | |
| *A61B 90/50* | (2016.01) | |
| *A61M 16/01* | (2006.01) | |
| *A61M 16/06* | (2006.01) | |
| *A61M 16/18* | (2006.01) | |
| *B01D 46/00* | (2022.01) | |
| *G06F 16/10* | (2019.01) | |
| *G06F 16/48* | (2019.01) | |
| *G06T 7/70* | (2017.01) | |
| *G06V 10/00* | (2022.01) | |
| *G16H 10/60* | (2018.01) | |
| *G16H 20/17* | (2018.01) | |
| *G16H 20/40* | (2018.01) | |
| *G16H 30/20* | (2018.01) | |
| *G16H 30/40* | (2018.01) | |

(52) U.S. Cl.
CPC .............. *A61M 16/18* (2013.01); *G06T 7/70* (2017.01); *G06V 10/00* (2022.01); *G16H 10/60* (2018.01); *G16H 20/40* (2018.01); *G16H 30/20* (2018.01); *A61B 46/10* (2016.02); *A61B 2050/155* (2016.02); *A61B 90/50* (2016.02); *A61M 16/01* (2013.01); *B01D 46/0093* (2013.01); *G06F 16/10* (2019.01); *G06F 16/48* (2019.01); *G06T 2207/20081* (2013.01); *G06T 2207/30004* (2013.01); *G06T 2210/41* (2013.01); *G16H 20/17* (2018.01); *G16H 30/40* (2018.01)

(58) Field of Classification Search
CPC ... A61B 2050/155; A61B 90/94; A61B 90/96; A61B 90/98; A61M 16/06; A61M 16/18; A61M 16/01; A61M 5/1414; A61M 5/16845; A61M 5/16895; A61M 13/00; A61M 16/00; A61M 16/04; A61M 2016/003; A61M 2202/0208; A61M 2202/0241; A61M 2202/0275; A61M 2202/0283; A61M 2202/048; A61M 2205/18; A61M 2205/3306; A61M 2205/3334; A61M 2205/3553; A61M 2205/3561; A61M 2205/3592; A61M 2205/505; A61M 2205/52; A61M 2205/6054; A61M 2205/6072; A61M 2205/80; A61M 2209/084; A61M 2210/04; A61M 2210/0606; A61M 2230/04; A61M 2230/06; A61M 2230/10; A61M 2230/205; A61M 2230/30; A61M 2230/42; A61M 2230/43; A61M 2230/46; A61M 2230/50; G06T 7/70; G06T 2207/20081; G06T 2207/30004; G06T 2210/41; G06V 10/00; G16H 10/60; G16H 20/40; G16H 30/20; G16H 20/17; G16H 30/40; G16H 10/40; G16H 40/63; G16H 40/67; G16H 50/20; G16H 50/70; B01D 46/0093; G06F 16/10; G06F 16/48
USPC ....... 382/128; 55/385.2, 467, 473, 485, 410, 55/356; 96/134, 146; 604/319, 322, 902, 604/189; 235/462.02
See application file for complete search history.

(56) References Cited

U.S. PATENT DOCUMENTS

| | | |
|---|---|---|
| 4,967,320 A | 10/1990 | Paschal |
| 5,000,737 A | 3/1991 | Free et al. |
| 5,399,007 A | 3/1995 | Marconet |
| 5,409,511 A | 4/1995 | Paul |
| 5,516,313 A | 5/1996 | Lumpkin |
| 5,626,140 A | 5/1997 | Feldman |
| 5,655,905 A | 8/1997 | Jaimes et al. |
| 5,695,536 A | 12/1997 | Fabrizi |
| 7,494,536 B2 | 2/2009 | Kang et al. |
| 7,597,731 B2 | 10/2009 | Palmerton et al. |
| 7,674,436 B1 | 3/2010 | Feldman et al. |
| 7,753,977 B2 | 7/2010 | Lyons et al. |
| 9,603,956 B2 | 3/2017 | Newham |
| 10,312,191 B2 | 6/2019 | Jung et al. |
| 10,507,153 B2 | 12/2019 | Augustine et al. |
| 10,512,191 B2 | 12/2019 | Augustine et al. |
| 10,638,638 B2 | 4/2020 | Augustine et al. |
| 10,652,577 B2 | 5/2020 | Thoreau et al. |
| 10,653,577 B2 | 5/2020 | Augustine et al. |
| 10,702,436 B2 | 7/2020 | Augustine et al. |
| 10,869,800 B2 | 12/2020 | Augustine et al. |
| 10,888,482 B2 | 1/2021 | Augustine et al. |
| 10,993,865 B2 | 5/2021 | Augustine et al. |
| 10,993,885 B1 | 5/2021 | Fernandez |
| 11,035,377 B2 | 6/2021 | Niwa et al. |
| 11,045,377 B2 | 6/2021 | Augustine et al. |
| 11,160,710 B1 | 11/2021 | Augustine et al. |
| 11,173,089 B2 | 11/2021 | Augustine et al. |
| 11,219,569 B2 | 1/2022 | Augustine et al. |

(56) References Cited

U.S. PATENT DOCUMENTS

| | | |
|---|---|---|
| 11,219,570 B2 | 1/2022 | Augustine et al. |
| 11,285,065 B2 | 3/2022 | Augustine et al. |
| 11,291,602 B2 | 4/2022 | Augustine et al. |
| 11,426,318 B2 | 8/2022 | Augustine et al. |
| 11,426,319 B2 | 8/2022 | Augustine et al. |
| 11,426,320 B2 | 8/2022 | Augustine et al. |
| 11,432,982 B2 | 9/2022 | Augustine et al. |
| 11,432,983 B2 | 9/2022 | Augustine et al. |
| 11,446,196 B2 | 9/2022 | Augustine et al. |
| 11,523,960 B2 | 12/2022 | Augustine et al. |
| 11,564,856 B2 | 1/2023 | Augustine et al. |
| 11,583,459 B2 | 2/2023 | Augustine et al. |
| 11,583,460 B2 | 2/2023 | Augustine et al. |
| 11,583,461 B2 | 2/2023 | Augustine et al. |
| 11,583,998 B2 | 2/2023 | Moon |
| 11,642,270 B2 | 5/2023 | Augustine et al. |
| 11,648,166 B2 | 5/2023 | Augustine et al. |
| 11,654,070 B2 | 5/2023 | Augustine et al. |
| 11,666,500 B1 | 6/2023 | Augustine et al. |
| 11,679,052 B2 | 6/2023 | Augustine et al. |
| 11,701,282 B2 | 7/2023 | Augustine et al. |
| 11,744,755 B2 | 9/2023 | Augustine et al. |
| 11,752,056 B1 | 9/2023 | Augustine et al. |
| 11,766,372 B2 | 9/2023 | Augustine et al. |
| 11,766,373 B2 | 9/2023 | Augustine et al. |
| 12,023,281 B2 | 7/2024 | Augustine et al. |
| 12,121,478 B2 | 10/2024 | Augustine et al. |
| 2001/0035702 A1 | 11/2001 | Murphy et al. |
| 2002/0074403 A1 | 6/2002 | Krichever et al. |
| 2002/0120211 A1 | 8/2002 | Wardle et al. |
| 2002/0183599 A1 | 12/2002 | Castellanos |
| 2003/0033790 A1 | 2/2003 | Hague |
| 2003/0141687 A1 | 7/2003 | Wixted et al. |
| 2003/0150328 A1 | 8/2003 | Hansson et al. |
| 2004/0103789 A1 | 6/2004 | Lan et al. |
| 2004/0176984 A1 | 9/2004 | White et al. |
| 2004/0247016 A1 | 12/2004 | Faries et al. |
| 2004/0249673 A1 | 12/2004 | Smith |
| 2004/0262146 A1 | 12/2004 | Platt et al. |
| 2005/0016982 A1 | 1/2005 | Campf et al. |
| 2005/0060974 A1 | 3/2005 | Palmerton et al. |
| 2005/0087256 A1 | 4/2005 | Clark |
| 2005/0097870 A1 | 5/2005 | Moshenrose |
| 2005/0261551 A1* | 11/2005 | Couvillon, Jr. .... A61B 1/00059 600/109 |
| 2006/0030820 A1 | 2/2006 | Alheidt et al. |
| 2006/0042205 A1 | 3/2006 | Kalous et al. |
| 2006/0144942 A1 | 7/2006 | Evans et al. |
| 2006/0163829 A1 | 7/2006 | Livengood et al. |
| 2006/0229506 A1 | 10/2006 | Castellanos |
| 2007/0199287 A1 | 8/2007 | Wiser |
| 2007/0225690 A1 | 9/2007 | Sekiguchi et al. |
| 2007/0253596 A1* | 11/2007 | Murata .............. G06V 30/2504 382/218 |
| 2007/0260487 A1 | 11/2007 | Bartfeld et al. |
| 2008/0097315 A1 | 4/2008 | Miner et al. |
| 2008/0173178 A1 | 7/2008 | Metteer |
| 2008/0314978 A1* | 12/2008 | Fedorko ................ G16H 70/40 235/385 |
| 2009/0141947 A1* | 6/2009 | Kyyko ................ G06V 40/165 382/118 |
| 2009/0188311 A1 | 7/2009 | Cadieux et al. |
| 2010/0094262 A1 | 4/2010 | Tripathi et al. |
| 2010/0172550 A1* | 7/2010 | Gilley ................ G11B 27/034 382/218 |
| 2010/0191541 A1 | 7/2010 | Prokoski |
| 2010/0324380 A1 | 12/2010 | Perkins et al. |
| 2010/0324936 A1 | 12/2010 | Vishnubhatla et al. |
| 2011/0030560 A1 | 2/2011 | Bohlen et al. |
| 2011/0054310 A1* | 3/2011 | Taylor .................. A61B 5/0059 600/425 |
| 2011/0196304 A1 | 8/2011 | Kramer et al. |
| 2011/0264136 A1 | 10/2011 | Choi et al. |
| 2011/0305376 A1* | 12/2011 | Neff ...................... G16H 40/20 382/128 |
| 2011/0317004 A1 | 12/2011 | Tao |
| 2012/0022443 A1 | 1/2012 | Robertson et al. |
| 2012/0024154 A1 | 2/2012 | Augustine et al. |
| 2012/0026308 A1 | 2/2012 | Johnson et al. |
| 2012/0154120 A1 | 6/2012 | Alloro et al. |
| 2012/0154582 A1 | 6/2012 | Johnson et al. |
| 2012/0177256 A1* | 7/2012 | Keefe .................... G16H 30/20 382/115 |
| 2012/0305787 A1 | 12/2012 | Henson |
| 2013/0041258 A1 | 2/2013 | Patrick et al. |
| 2013/0225945 A1 | 8/2013 | Prince et al. |
| 2013/0243647 A1 | 9/2013 | Garner et al. |
| 2013/0269714 A1 | 10/2013 | Roe et al. |
| 2013/0277430 A1* | 10/2013 | Zumsteg ............ G06K 7/10009 235/462.08 |
| 2014/0081175 A1 | 3/2014 | Telfort |
| 2014/0194793 A1 | 7/2014 | Nakata et al. |
| 2014/0262553 A1 | 9/2014 | Pollock et al. |
| 2015/0168207 A1 | 6/2015 | Pollock et al. |
| 2015/0209510 A1* | 7/2015 | Burkholz ................ G06F 3/011 604/93.01 |
| 2015/0220080 A1 | 8/2015 | Nixon et al. |
| 2015/0223890 A1 | 8/2015 | Miller et al. |
| 2015/0224237 A1 | 8/2015 | Reasoner et al. |
| 2015/0363566 A1 | 12/2015 | Johnson et al. |
| 2016/0001213 A1 | 1/2016 | Balcik |
| 2016/0042623 A1 | 2/2016 | Riley et al. |
| 2016/0085922 A1 | 3/2016 | Sweeney |
| 2016/0103967 A1 | 4/2016 | Bulut et al. |
| 2016/0119593 A1 | 4/2016 | Schultz et al. |
| 2016/0125137 A1 | 5/2016 | Ott |
| 2016/0188831 A1 | 6/2016 | Kurtz et al. |
| 2016/0225144 A1* | 8/2016 | Spahn .................. A61B 5/7425 |
| 2016/0247277 A1* | 8/2016 | Kriheli .................... G06V 20/52 |
| 2016/0283691 A1 | 9/2016 | Ali |
| 2016/0362234 A1 | 12/2016 | Peret et al. |
| 2016/0379504 A1 | 12/2016 | Bailey et al. |
| 2017/0039227 A1 | 2/2017 | Herbst et al. |
| 2017/0095170 A1 | 4/2017 | Verkruijsse et al. |
| 2017/0112954 A1 | 4/2017 | Dayton |
| 2017/0140125 A1 | 5/2017 | Hogg et al. |
| 2017/0142933 A1 | 5/2017 | Neskin et al. |
| 2017/0147787 A1* | 5/2017 | Albrecht ................ G16H 40/67 |
| 2017/0156661 A1 | 6/2017 | Hughes et al. |
| 2017/0173262 A1 | 6/2017 | Veltz |
| 2017/0185717 A1* | 6/2017 | Williams ................ G16H 70/20 |
| 2017/0209658 A1 | 7/2017 | Tobia et al. |
| 2017/0235913 A1* | 8/2017 | Aly ........................ G16H 30/40 705/2 |
| 2017/0238842 A1 | 8/2017 | Jacquel et al. |
| 2017/0251990 A1 | 9/2017 | Kheradpir et al. |
| 2017/0262614 A1 | 9/2017 | Vishnubhatla et al. |
| 2017/0300385 A1 | 10/2017 | Huang |
| 2017/0326385 A1 | 11/2017 | Fishman |
| 2017/0333626 A1 | 11/2017 | Mansour |
| 2017/0337493 A1 | 11/2017 | Paramasivan et al. |
| 2018/0008787 A1 | 1/2018 | Schriver et al. |
| 2018/0036583 A1 | 2/2018 | Lagree et al. |
| 2018/0067484 A1 | 3/2018 | Troy et al. |
| 2018/0132966 A1 | 5/2018 | Desaulniers et al. |
| 2018/0169327 A1* | 6/2018 | Iddon .................... A61M 5/14546 |
| 2018/0182475 A1 | 6/2018 | Cossler et al. |
| 2018/0225346 A1 | 8/2018 | Liu et al. |
| 2018/0303574 A1 | 10/2018 | Ramirez Luna et al. |
| 2018/0353698 A1 | 12/2018 | Saint et al. |
| 2018/0365385 A1 | 12/2018 | Cooney et al. |
| 2019/0057760 A1 | 2/2019 | Schwartz et al. |
| 2019/0105120 A1 | 4/2019 | Norman et al. |
| 2019/0183591 A1 | 6/2019 | Johnson et al. |
| 2019/0197466 A1 | 6/2019 | Hand, III et al. |
| 2019/0201126 A1 | 7/2019 | Shelton, IV et al. |
| 2019/0201158 A1 | 7/2019 | Shelton, IV et al. |
| 2019/0290524 A1 | 9/2019 | Augustine et al. |
| 2019/0294965 A1 | 9/2019 | Buhrmann et al. |
| 2019/0297745 A1 | 9/2019 | Augustine et al. |
| 2019/0328598 A1 | 10/2019 | Mangiardi |
| 2019/0333621 A1 | 10/2019 | Bengtsson et al. |

(56) References Cited

U.S. PATENT DOCUMENTS

| | | | |
|---|---|---|---|
| 2019/0357382 | A1 | 11/2019 | Augustine et al. |
| 2020/0004027 | A1* | 1/2020 | Grootjans .......... G02B 27/0101 |
| 2020/0038274 | A1 | 2/2020 | Augustine et al. |
| 2020/0046590 | A1 | 2/2020 | Augustine et al. |
| 2020/0121496 | A1 | 4/2020 | Prokop et al. |
| 2020/0160057 | A1 | 5/2020 | Roxas et al. |
| 2020/0230316 | A1 | 7/2020 | Guerra et al. |
| 2020/0268315 | A1 | 8/2020 | Burwinkel et al. |
| 2020/0273581 | A1 | 8/2020 | Wolf et al. |
| 2020/0281790 | A1 | 9/2020 | Augustine et al. |
| 2020/0286610 | A1 | 9/2020 | Wartena et al. |
| 2020/0289354 | A1 | 9/2020 | Augustine et al. |
| 2020/0305713 | A1 | 10/2020 | Sipe et al. |
| 2021/0052454 | A1 | 2/2021 | Augustine et al. |
| 2021/0100710 | A1 | 4/2021 | Augustine et al. |
| 2021/0196550 | A1 | 7/2021 | Augustine et al. |
| 2021/0251835 | A1 | 8/2021 | Augustine et al. |
| 2021/0316633 | A1 | 10/2021 | Kalligeros et al. |
| 2021/0338510 | A1 | 11/2021 | Augustine et al. |
| 2021/0338511 | A1 | 11/2021 | Augustine et al. |
| 2021/0345954 | A1 | 11/2021 | Shelton, IV et al. |
| 2021/0361507 | A1 | 11/2021 | Augustine et al. |
| 2021/0361508 | A1 | 11/2021 | Augustine et al. |
| 2021/0361509 | A1 | 11/2021 | Augustine et al. |
| 2021/0375480 | A1 | 12/2021 | Mahon et al. |
| 2022/0062084 | A1 | 3/2022 | Augustine et al. |
| 2022/0071828 | A1 | 3/2022 | Augustine et al. |
| 2022/0096305 | A1 | 3/2022 | Augustine et al. |
| 2022/0104987 | A1 | 4/2022 | Augustine et al. |
| 2022/0183915 | A1 | 6/2022 | Augustine et al. |
| 2022/0202639 | A1 | 6/2022 | Augustine et al. |
| 2022/0280085 | A1 | 9/2022 | Retzkin et al. |
| 2022/0347031 | A1 | 11/2022 | Augustine et al. |
| 2022/0354723 | A1 | 11/2022 | Augustine et al. |
| 2022/0362085 | A1 | 11/2022 | Augustine et al. |
| 2022/0362086 | A1 | 11/2022 | Augustine et al. |
| 2022/0362087 | A1 | 11/2022 | Augustine et al. |
| 2022/0362493 | A1 | 11/2022 | White |
| 2022/0367020 | A1 | 11/2022 | Augustine et al. |
| 2022/0370275 | A1 | 11/2022 | Augustine et al. |
| 2023/0149236 | A1 | 5/2023 | Augustine et al. |
| 2023/0149237 | A1 | 5/2023 | Augustine et al. |
| 2023/0149238 | A1 | 5/2023 | Augustine et al. |
| 2023/0149239 | A1 | 5/2023 | Augustine et al. |
| 2023/0157918 | A1 | 5/2023 | Augustine et al. |
| 2023/0233394 | A1 | 7/2023 | Augustine et al. |
| 2023/0270609 | A1 | 8/2023 | Augustine et al. |
| 2023/0270610 | A1 | 8/2023 | Augustine et al. |
| 2023/0293374 | A1 | 9/2023 | Augustine et al. |
| 2023/0293375 | A1 | 9/2023 | Augustine et al. |
| 2023/0346621 | A1 | 11/2023 | Augustine et al. |
| 2023/0346622 | A1 | 11/2023 | Augustine et al. |
| 2023/0346623 | A1 | 11/2023 | Augustine et al. |
| 2023/0355457 | A1 | 11/2023 | Augustine et al. |
| 2023/0360790 | A1* | 11/2023 | Burkholz .............. G16H 20/17 |
| 2023/0404830 | A1 | 12/2023 | Augustine et al. |
| 2023/0414432 | A1 | 12/2023 | Augustine et al. |
| 2023/0414433 | A1 | 12/2023 | Augustine et al. |
| 2024/0207122 | A1 | 6/2024 | Augustine et al. |
| 2024/0423857 | A1 | 12/2024 | Augustine et al. |

FOREIGN PATENT DOCUMENTS

| | | | |
|---|---|---|---|
| WO | WO-2017161131 | A1 | 9/2017 |
| WO | WO-2019191081 | A1 | 10/2019 |
| WO | WO-2021236077 | A1 | 11/2021 |
| WO | WO-2021236182 | A1 | 11/2021 |
| WO | WO-2021236319 | A1 | 11/2021 |

OTHER PUBLICATIONS

U.S. Appl. No. 16/529,283 U.S. Pat. No. 10,638,638, Aug. 1, 2019, Relocation Module for Patient Monitors and Surgical Equipment.

U.S. Appl. No. 16/364,884 U.S. Pat. No. 10,507,153, Mar. 26, 2019, Relocation Modules and Methods for Surgical Field.

U.S. Appl. No. 18/222,711, filed Jul. 17, 2023, Relocation Modules and Methods for Surgical Field.

U.S. Appl. No. 16/593,033 U.S. Pat. No. 10,653,577, Oct. 4, 2019, Relocation Modules and Methods for Surgical Field.

U.S. Appl. No. 16/601,924 U.S. Pat. No. 10,702,436, Oct. 15, 2019, Relocation Modules and Methods for Surgical Field.

U.S. Appl. No. 16/885,715 U.S. Pat. No. 10,888,482, May 28, 2020, Relocation Modules and Methods for Surgical Field.

U.S. Appl. No. 17/103,426 U.S. Pat. No. 11,045,377, Nov. 24, 2020, Relocation Modules and Methods for Surgical Field.

U.S. Appl. No. 17/308,437 U.S. Pat. No. 11,285,065, May 5, 2021, Relocation Modules and Methods for Surgical Field.

U.S. Appl. No. 17/523,549 U.S. Pat. No. 11,426,319, Nov. 10, 2021, Relocation Modules and Methods for Surgical Field.

U.S. Appl. No. 17/873,907 U.S. Pat. No. 11,642,270, Jul. 26, 2022, Relocation Modules and Methods for Surgical Field.

U.S. Appl. No. 18/191,115 U.S. Pat. No. 11,766,373, Mar. 28, 2023, Relocation Modules and Methods for Surgical Field.

U.S. Appl. No. 16/879,406 U.S. Pat. No. 10,869,800, May 20, 2020, Relocation Module and Methods for Surgical Equipment.

U.S. Appl. No. 18/830,087, filed Sep. 10, 2024, Relocation Module and Methods for Surgical Equipment.

U.S. Appl. No. 17/092,681 U.S. Pat. No. 10,993,865, Nov. 9, 2020, Relocation Module and Methods for Surgical Equipment.

U.S. Appl. No. 17/199,722 U.S. Pat. No. 11,173,089, Mar. 12, 2021, Relocation Module and Methods for Surgical Equipment.

U.S. Appl. No. 17/375,546 U.S. Pat. No. 11,291,602, Jul. 14, 2021, Relocation Module and Methods for Surgical Equipment.

U.S. Appl. No. 17/697,398 U.S. Pat. No. 11,523,960, Mar. 17, 2022, Relocation Module and Methods for Surgical Equipment.

U.S. Appl. No. 17/875,055 U.S. Pat. No. 11,583,461, Jul. 27, 2022, Relocation Module and Methods for Surgical Equipment.

U.S. Appl. No. 18/099,475 U.S. Pat. No. 11,666,500, Jan. 20, 2023, Relocation Module and Methods for Surgical Equipment.

U.S. Appl. No. 18/136,141 U.S. Pat. No. 11,752,056, Apr. 18, 2023, Relocation Module and Methods for Surgical Equipment.

U.S. Appl. No. 18/218,344 U.S. Pat. No. 12,121,478 filed Jul. 5, 2023, Relocation Module and Methods for Surgical Equipment.

U.S. Appl. No. 17/167,681 U.S. Pat. No. 11,160,710, Feb. 4, 2021, Relocation Module and Methods for Surgical Equipment.

U.S. Appl. No. 17/332,523 U.S. Pat. No. 11,219,569, May 27, 2021, Relocation Module and Methods for Surgical Equipment.

U.S. Appl. No. 17/550,611 U.S. Pat. No. 11,426,320, Dec. 14, 2021, Relocation Module and Methods for Surgical Equipment.

U.S. Appl. No. 17/862,971 U.S. Pat. No. 11,583,459, Jul. 12, 2022, Relocation Module and Methods for Surgical Equipment.

U.S. Appl. No. 18/099,500 U.S. Pat. No. 11,744,755, Jan. 20, 2023, Relocation Module and Methods for Surgical Equipment.

U.S. Appl. No. 18/203,297, filed May 30, 2023, Relocation Module and Methods for Surgical Equipment.

U.S. Appl. No. 17/245,942 U.S. Pat. No. 11,426,318, Apr. 30, 2021, Medical Module Including Automated Dose-Response Record System.

U.S. Appl. No. 17/873,975 U.S. Pat. No. 11,583,460, Jul. 26, 2022, Medical Module Including Automated Dose-Response Record System.

U.S. Appl. No. 18/099,557 U.S. Pat. No. 11,679,052, Jan. 20, 2023, Medical Module Including Automated Dose-Response Record System.

U.S. Appl. No. 18/142,776 U.S. Pat. No. 11,766,372, May 3, 2023, Medical Module Including Automated Dose-Response Record System.

U.S. Appl. No. 18/218,350, filed Jul. 5, 2023, Medical Module Including Automated Dose-Response Record System.

U.S. Appl. No. 18/243,820, filed Sep. 8, 2023, Medical Module Including Automated Dose-Response Record System.

U.S. Appl. No. 17/376,469 U.S. Pat. No. 11,219,570, Jul. 15, 2021, Relocation Module and Methods for Surgical Equipment.

U.S. Appl. No. 17/550,696 U.S. Pat. No. 11,432,983, Dec. 14, 2021, Relocation Module and Methods for Surgical Equipment.

(56) References Cited

OTHER PUBLICATIONS

U.S. Appl. No. 17/874,998 U.S. Pat. No. 11,564,856, Jul. 27, 2022, Relocation Module and Methods for Surgical Equipment.
U.S. Appl. No. 18/092,532 U.S. Pat. No. 11,701,282, Jan. 3, 2023, Relocation Module and Methods for Surgical Equipment.
U.S. Appl. No. 18/203,936, filed May 31, 2023, Relocation Module and Methods for Surgical Equipment.
U.S. Appl. No. 18/243,223, filed Sep. 7, 2023, Relocation Module and Methods for Surgical Equipment.
U.S. Appl. No. 17/678,550 U.S. Pat. No. 11,446,196, Feb. 23, 2022, Relocation Module and Methods for Surgical Equipment.
U.S. Appl. No. 17/528,832 U.S. Pat. No. 11,432,982, Nov. 17, 2021, Relocation Module and Methods for Surgical Equipment.
U.S. Appl. No. 17/873,857 U.S. Pat. No. 11,654,070, Jul. 26, 2022, Relocation Module and Methods for Surgical Equipment.
U.S. Appl. No. 17/874,963 U.S. Pat. No. 11,648,166, Jul. 27, 2022, Relocation Module and Methods for Surgical Equipment.
U.S. Appl. No. 18/099,074, filed Jan. 19, 2023, Relocation Module and Methods for Surgical Equipment.
U.S. Appl. No. 18/142,787 U.S. Pat. No. 12,023,281, May 3, 2023, Relocation Module and Methods for Surgical Equipment.
U.S. Appl. No. 18/242,894, filed Sep. 6, 2023, Relocation Module and Methods for Surgical Equipment.
U.S. Appl. No. 18/598,110, filed Mar. 7, 2024, Relocation Module and Methods for Surgical Equipment.
"U.S. Appl. No. 15/935,524, Corrected Notice of Allowability mailed Jul. 18, 2019", 2 pgs.
"U.S. Appl. No. 15/935,524, Corrected Notice of Allowability mailed Aug. 21, 2019", 2 pgs.
"U.S. Appl. No. 15/935,524, Non Final Office Action mailed Mar. 8, 2019", 8 pgs.
"U.S. Appl. No. 15/935,524, Non Final Office Action mailed Sep. 19, 2018", 8 pgs.
"U.S. Appl. No. 15/935,524, Notice of Allowance mailed Jun. 12, 2019", 9 pgs.
"U.S. Appl. No. 15/935,524, Response filed May 15, 2019 to Non Final Office Action mailed Mar. 8, 2019", 10 pgs.
"U.S. Appl. No. 15/935,524, Response filed Dec. 12, 2018 to Non Final Office Action mailed Sep. 19, 2018", 18 pgs.
"U.S. Appl. No. 16/364,884, Corrected Notice of Allowability mailed Aug. 29, 2019", 3 pgs.
"U.S. Appl. No. 16/364,884, Corrected Notice of Allowability mailed Nov. 8, 2019", 3 pgs.
"U.S. Appl. No. 16/364,884, Non Final Office Action mailed Jul. 3, 2019", 9 pgs.
"U.S. Appl. No. 16/364,884, Notice of Allowance mailed Aug. 20, 2019", 10 pgs.
"U.S. Appl. No. 16/364,884, Response filed Jun. 18, 2019 to Restriction Requirement mailed May 1, 2019", 9 pgs.
"U.S. Appl. No. 16/364,884, Response filed Jul. 24, 2019 to Non Final Office Action mailed Jul. 3, 2019", 9 pgs.
"U.S. Appl. No. 16/364,884, Restriction Requirement mailed May 1, 2019", 5 pgs.
"U.S. Appl. No. 16/519,677, Non Final Office Action mailed Nov. 13, 2019", 6 pgs.
"U.S. Appl. No. 16/519,677, Response filed Dec. 17, 2019 to Non Final Office Action mailed Nov. 13, 2019", 9 pgs.
"U.S. Appl. No. 16/529,283, Corrected Notice of Allowability mailed Mar. 6, 2020", 2 pgs.
"U.S. Appl. No. 16/529,283, Non Final Office Action mailed Sep. 18, 2019", 8 pgs.
"U.S. Appl. No. 16/529,283, Notice of Allowance mailed Jan. 10, 2020", 10 pgs.
"U.S. Appl. No. 16/529,283, Response filed Dec. 13, 2019 to Non Final Office Action mailed Sep. 18, 2019", 8 pgs.
"U.S. Appl. No. 16/593,033, Notice of Allowance mailed Jan. 14, 2020", 10 pgs.
"U.S. Appl. No. 16/601,924, Non Final Office Action mailed Dec. 5, 2019", 6 pgs.
"U.S. Appl. No. 16/601,924, Notice of Allowance mailed Mar. 11, 2020", 8 pgs.
"U.S. Appl. No. 16/601,924, Response filed Feb. 26, 2020 to Non Final Office Action mailed Dec. 5, 2019", 9 pgs.
"U.S. Appl. No. 16/879,406, Corrected Notice of Allowability mailed Oct. 21, 2020", 2 pgs.
"U.S. Appl. No. 16/879,406, Non Final Office Action mailed Jun. 9, 2020", 9 pgs.
"U.S. Appl. No. 16/879,406, Notice of Allowance mailed Sep. 10, 2020", 8 pgs.
"U.S. Appl. No. 16/879,406, Response filed Sep. 2, 2020 to Non Final Office Action mailed Jun. 9, 2020", 12 pgs.
"U.S. Appl. No. 16/885,715, Non Final Office Action mailed Jun. 23, 2020", 9 pgs.
"U.S. Appl. No. 16/885,715, Notice of Allowance mailed Sep. 22, 2020", 8 pgs.
"U.S. Appl. No. 16/885,715, Notice of Non-Compliant Amendment mailed Sep. 10, 2020", 2 pgs.
"U.S. Appl. No. 16/885,715, Response filed Sep. 2, 2020 to Non Final Office Action mailed Jun. 23, 2020", 12 pgs.
"U.S. Appl. No. 16/885,715, Response filed Sep. 14, 2020 to Notice of Non-Compliant Amendment mailed Sep. 10, 2020", 12 pgs.
"U.S. Appl. No. 17/092,681, Non Final Office Action mailed Dec. 17, 2020", 8 pgs.
"U.S. Appl. No. 17/092,681, Notice of Allowance mailed Feb. 2, 2021", 9 pgs.
"U.S. Appl. No. 17/092,681, Response filed Jan. 22, 2021 to Non Final Office Action mailed Dec. 17, 2020", 13 pgs.
"U.S. Appl. No. 17/103,426, Non Final Office Action mailed Jan. 25, 2021", 8 pgs.
"U.S. Appl. No. 17/103,426, Notice of Allowance mailed Mar. 12, 2021", 8 pgs.
"U.S. Appl. No. 17/103,426, Response filed Mar. 2, 2021 to Non Final Office Action mailed Jan. 25, 2021", 9 pgs.
"U.S. Appl. No. 17/167,681, Corrected Notice of Allowability mailed Sep. 21, 2021", 2 pgs.
"U.S. Appl. No. 17/167,681, Non Final Office Action mailed Apr. 5, 2021", 8 pgs.
"U.S. Appl. No. 17/167,681, Notice of Allowance mailed May 17, 2021", 9 pgs.
"U.S. Appl. No. 17/167,681, Notice of Allowance mailed Aug. 25, 2021", 12 pgs.
"U.S. Appl. No. 17/167,681, Response filed May 5, 2021 to Non Final Office Action mailed Apr. 5, 2021", 10 pgs.
"U.S. Appl. No. 17/199,722, Non Final Office Action mailed May 12, 2021", 7 pgs.
"U.S. Appl. No. 17/199,722, Notice of Allowance mailed Jul. 26, 2021", 9 pgs.
"U.S. Appl. No. 17/199,722, Preliminary Amendment filed Apr. 12, 2021", 12.
"U.S. Appl. No. 17/199,722, Response filed Jul. 14, 2021 to Non Final Office Action mailed May 12, 2021", 15 pgs.
"U.S. Appl. No. 17/245,942, Corrected Notice of Allowability mailed Aug. 2, 2022", 2 pgs.
"U.S. Appl. No. 17/245,942, Final Office Action mailed Mar. 2, 2022", 9 pgs.
"U.S. Appl. No. 17/245,942, Non Final Office Action mailed Jun. 30, 2021", 11 pgs.
"U.S. Appl. No. 17/245,942, Non Final Office Action mailed Nov. 19, 2021", 13 pgs.
"U.S. Appl. No. 17/245,942, Notice of Allowance mailed May 2, 2022", 10 pgs.
"U.S. Appl. No. 17/245,942, Notice of Allowance mailed Jul. 27, 2021", 9 pgs.
"U.S. Appl. No. 17/245,942, Response filed Feb. 15, 2022 to Non Final Office Action mailed Nov. 19, 2021", 14 pgs.
"U.S. Appl. No. 17/245,942, Response filed Apr. 15, 2022 to Final Office Action mailed Mar. 2, 2022", 15 pgs.
"U.S. Appl. No. 17/245,942, Response filed Jul. 14, 2021 to Non Final Office Action mailed Jun. 30, 2021", 14 pgs.
"U.S. Appl. No. 17/308,437, Non Final Office Action mailed Jul. 15, 2021", 8 pgs.

(56) References Cited

OTHER PUBLICATIONS

"U.S. Appl. No. 17/308,437, Notice of Allowance mailed Dec. 6, 2021", 9 pgs.
"U.S. Appl. No. 17/308,437, Response filed Nov. 10, 2021 to Non Final Office Action mailed Jul. 15, 2021", 11 pgs.
"U.S. Appl. No. 17/332,523, Non Final Office Action mailed Jul. 29, 2021", 8 pgs.
"U.S. Appl. No. 17/332,523, Notice of Allowance mailed Oct. 29, 2021", 9 pgs.
"U.S. Appl. No. 17/332,523, Response filed Sep. 29, 2021 to Non Final Office Action mailed Jul. 29, 2021", 13 pgs.
"U.S. Appl. No. 17/375,546, Non Final Office Action mailed Oct. 27, 2021", 8 pgs.
"U.S. Appl. No. 17/375,546, Notice of Allowance mailed Feb. 25, 2022", 10 pgs.
"U.S. Appl. No. 17/375,546, Response filed Jan. 27, 2022 to Non Final Office Action mailed Oct. 27, 2021", 14 pgs.
"U.S. Appl. No. 17/376,469, Non Final Office Action mailed Sep. 17, 2021", 9 pgs.
"U.S. Appl. No. 17/376,469, Notice of Allowance mailed Nov. 23, 2021", 9 pgs.
"U.S. Appl. No. 17/376,469, Response filed Sep. 29, 2021 to Non Final Office Action mailed Sep. 17, 2021", 11 pgs.
"U.S. Appl. No. 17/523,549, Corrected Notice of Allowability mailed Jun. 2, 2022", 2 pgs.
"U.S. Appl. No. 17/523,549, Final Office Action mailed Apr. 19, 2022", 8 pgs.
"U.S. Appl. No. 17/523,549, Non Final Office Action mailed Jan. 13, 2022", 8 pgs.
"U.S. Appl. No. 17/523,549, Notice of Allowance mailed May 3, 2022", 9 pgs.
"U.S. Appl. No. 17/523,549, Response filed Apr. 13, 2022 to Non Final Office Action mailed Jan. 13, 2022", 12 pgs.
"U.S. Appl. No. 17/523,549, Response filed Apr. 19, 2022 to Final Office Action mailed Apr. 19, 2022", 12 pgs.
"U.S. Appl. No. 17/528,832, Final Office Action mailed Apr. 22, 2022", 10 pgs.
"U.S. Appl. No. 17/528,832, Non Final Office Action mailed Feb. 8, 2022", 11 pgs.
"U.S. Appl. No. 17/528,832, Notice of Allowance mailed Jun. 29, 2022", 10 pgs.
"U.S. Appl. No. 17/528,832, Response filed Apr. 15, 2022 to Non Final Office Action mailed Feb. 8, 2022", 13 pgs.
"U.S. Appl. No. 17/528,832, Response filed Jun. 20, 2022 to Final Office Action mailed Apr. 22, 2022", 13 pgs.
"U.S. Appl. No. 17/550,611, Corrected Notice of Allowability mailed May 4, 2022", 2 pgs.
"U.S. Appl. No. 17/550,611, Corrected Notice of Allowability mailed Jul. 15, 2022", 2 pgs.
"U.S. Appl. No. 17/550,611, Non Final Office Action mailed Feb. 10, 2022", 8 pgs.
"U.S. Appl. No. 17/550,611, Notice of Allowance mailed Apr. 25, 2022", 9 pgs.
"U.S. Appl. No. 17/550,611, Response filed Apr. 15, 2022 to Non Final Office Action mailed Feb. 10, 2022", 13 pgs.
"U.S. Appl. No. 17/550,696, Corrected Notice of Allowability mailed Aug. 8, 2022", 3 pgs.
"U.S. Appl. No. 17/550,696, Non Final Office Action mailed Feb. 10, 2022", 8 pgs.
"U.S. Appl. No. 17/550,696, Notice of Allowance mailed May 17, 2022", 10 pgs.
"U.S. Appl. No. 17/550,696, Response filed May 9, 2022 to Non Final Office Action mailed Feb. 10, 2022", 12 pgs.
"U.S. Appl. No. 17/678,550, Final Office Action mailed Jun. 3, 2022", 7 pgs.
"U.S. Appl. No. 17/678,550, Non Final Office Action mailed May 13, 2022", 7 pgs.
"U.S. Appl. No. 17/678,550, Notice of Allowance mailed Aug. 11, 2022", 9 pgs.
"U.S. Appl. No. 17/678,550, Preliminary Amendment filed Apr. 7, 2022", 11 pgs.
"U.S. Appl. No. 17/678,550, Response filed May 23, 2022 to Non Final Office Action mailed May 13, 2022", 14 pgs.
"U.S. Appl. No. 17/678,550, Response filed Aug. 1, 2022 to Final Office Action mailed Jun. 3, 2022", 14 pgs.
"U.S. Appl. No. 17/678,550, Supplemental Amendment filed Aug. 2, 2022", 13 pgs.
"U.S. Appl. No. 17/697,398, Non Final Office Action mailed May 27, 2022", 7 pgs.
"U.S. Appl. No. 17/697,398, Notice of Allowance mailed Aug. 19, 2022", 9 pgs.
"U.S. Appl. No. 17/697,398, Response filed Aug. 2, 2022 to Non Final Office Action mailed May 27, 2022", 12 pgs.
"U.S. Appl. No. 17/862,971, Non Final Office Action mailed Nov. 15, 2022", 7 pgs.
"U.S. Appl. No. 17/862,971, Notice of Allowance mailed Nov. 20, 2022", 9 pgs.
"U.S. Appl. No. 17/862,971, Notice of Allowance mailed Dec. 20, 2022", 9 pgs.
"U.S. Appl. No. 17/862,971, Response filed Dec. 5, 2022 to Non Final Office Action mailed Nov. 15, 2022", 11 pgs.
"U.S. Appl. No. 17/873,857, Corrected Notice of Allowability mailed Apr. 13, 2023", 2 pgs.
"U.S. Appl. No. 17/873,857, Non Final Office Action mailed Nov. 14, 2022", 7 pgs.
"U.S. Appl. No. 17/873,857, Notice of Allowance mailed Dec. 21, 2022", 9 pgs.
"U.S. Appl. No. 17/873,857, Response filed Dec. 5, 2022 to Non Final Office Action mailed Nov. 14, 2022", 13 pgs.
"U.S. Appl. No. 17/873,857, Supplemental Notice of Allowability mailed Mar. 14, 2023", 5 pgs.
"U.S. Appl. No. 17/873,907, Final Office Action mailed Dec. 13, 2022", 7 pgs.
"U.S. Appl. No. 17/873,907, Non Final Office Action mailed Nov. 14, 2022", 7 pgs.
"U.S. Appl. No. 17/873,907, Notice of Allowance mailed Jan. 25, 2023", 9 pgs.
"U.S. Appl. No. 17/873,907, Response filed Dec. 5, 2022 to Non Final Office Action mailed Nov. 14, 2022", 12 pgs.
"U.S. Appl. No. 17/873,907, Response filed Dec. 14, 2022 to Final Office Action mailed Dec. 13, 2022", 10 pgs.
"U.S. Appl. No. 17/873,975, Non Final Office Action mailed Nov. 15, 2022", 7 pgs.
"U.S. Appl. No. 17/873,975, Notice of Allowance mailed Dec. 21, 2022", 9 pgs.
"U.S. Appl. No. 17/873,975, Response filed Dec. 5, 2022 to Non Final Office Action mailed Nov. 15, 2022", 14 pgs.
"U.S. Appl. No. 17/874,963, Corrected Notice of Allowability mailed Apr. 13, 2023", 2 pgs.
"U.S. Appl. No. 17/874,963, Non Final Office Action mailed Nov. 14, 2022", 7 pgs.
"U.S. Appl. No. 17/874,963, Notice of Allowance mailed Dec. 21, 2022", 9 pgs.
"U.S. Appl. No. 17/874,963, Response filed Dec. 5, 2022 to Non Final Office Action mailed Nov. 14, 2022", 12 pgs.
"U.S. Appl. No. 17/874,963, Supplemental Notice of Allowability mailed Mar. 14, 2023", 6 pgs.
"U.S. Appl. No. 17/874,998, Non Final Office Action mailed Nov. 15, 2022", 7 pgs.
"U.S. Appl. No. 17/874,998, Notice of Allowance mailed Dec. 16, 2022", 9 pgs.
"U.S. Appl. No. 17/874,998, Response filed Dec. 5, 2022 to Non Final Office Action mailed Nov. 15, 2022", 13 pgs.
"U.S. Appl. No. 17/875,055, Non Final Office Action mailed Nov. 15, 2022", 8 pgs.
"U.S. Appl. No. 17/875,055, Notice of Allowance mailed Dec. 22, 2022", 9 pgs.
"U.S. Appl. No. 17/875,055, Response filed Dec. 5, 2022 to Non Final Office Action mailed Nov. 15, 2022", 11 pgs.
"U.S. Appl. No. 18/092,532, Non Final Office Action mailed Apr. 14, 2023", 7 pgs.

(56) References Cited

OTHER PUBLICATIONS

"U.S. Appl. No. 18/092,532, Notice of Allowance mailed May 24, 2023", 8 pgs.
"U.S. Appl. No. 18/092,532, Response filed Apr. 27, 2023 to Non Final Office Action mailed Apr. 14, 2023", 12 pgs.
"U.S. Appl. No. 18/099,074, Non Final Office Action mailed Apr. 17, 2023", 8 pgs.
"U.S. Appl. No. 18/099,074, Non Final Office Action mailed Oct. 20, 2023", 90 pgs.
"U.S. Appl. No. 18/099,074, Notice of Allowance mailed Aug. 7, 2023", 8 pgs.
"U.S. Appl. No. 18/099,074, Response filed Jul. 13, 2023 to Non Final Office Action mailed Apr. 17, 2023", 12 pgs.
"U.S. Appl. No. 18/099,475, Corrected Notice of Allowability mailed Apr. 19, 2023", 2 pgs.
"U.S. Appl. No. 18/099,475, Non Final Office Action mailed Mar. 8, 2023", 7 pgs.
"U.S. Appl. No. 18/099,475, Notice of Allowance mailed Apr. 4, 2023", 8 pgs.
"U.S. Appl. No. 18/099,475, Response filed Mar. 17, 2023 to Non Final Office Action mailed Mar. 8, 2023", 13 pgs.
"U.S. Appl. No. 18/099,500, Notice of Allowance mailed May 5, 2023", 9 pgs.
"U.S. Appl. No. 18/099,557, Corrected Notice of Allowability mailed Apr. 14, 2023", 2 pgs.
"U.S. Appl. No. 18/099,557, Non Final Office Action mailed Mar. 6, 2023", 7 pgs.
"U.S. Appl. No. 18/099,557, Notice of Allowance mailed Apr. 5, 2023", 8 pgs.
"U.S. Appl. No. 18/099,557, Response filed Mar. 17, 2023 to Non Final Office Action mailed Mar. 6, 2023", 13 pgs.
"U.S. Appl. No. 18/136,141, Corrected Notice of Allowability mailed Aug. 16, 2023", 2 pgs.
"U.S. Appl. No. 18/136,141, Non Final Office Action mailed Jun. 12, 2023", 7 pgs.
"U.S. Appl. No. 18/136,141, Notice of Allowance mailed Jul. 11, 2023", 8 pgs.
"U.S. Appl. No. 18/136,141, Preliminary Amendment filed Apr. 18, 2023".
"U.S. Appl. No. 18/136,141, Response filed Jun. 28, 2023 to Non Final Office Action mailed Jun. 12, 2023", 11 pgs.
"U.S. Appl. No. 18/142,776, Non Final Office Action mailed Jun. 13, 2023", 7 pgs.
"U.S. Appl. No. 18/142,776, Notice of Allowance mailed Jul. 19, 2023", 8 pgs.
"U.S. Appl. No. 18/142,776, Response filed Jun. 28, 2023 to Non Final Office Action mailed Jun. 13, 2023", 13 pgs.
"U.S. Appl. No. 18/142,787, Non Final Office Action mailed Jan. 24, 2024", 23 pgs.
"U.S. Appl. No. 18/142,787, Non Final Office Action mailed Aug. 4, 2023", 9 pgs.
"U.S. Appl. No. 18/142,787, Notice of Allowance mailed Mar. 6, 2024", 11 pgs.
"U.S. Appl. No. 18/142,787, Notice of Allowance mailed Aug. 30, 2023", 9 pgs.
"U.S. Appl. No. 18/142,787, Response filed Feb. 22, 2024 to Non Final Office Action mailed Jan. 24, 2024", 15 pgs.
"U.S. Appl. No. 18/142,787, Response filed Aug. 21, 2023 to Non Final Office Action mailed Aug. 4, 2023", 14 pgs.
"U.S. Appl. No. 18/142,787, Supplemental Notice of Allowability mailed May 20, 2024", 3 pgs.
"U.S. Appl. No. 18/191,115, Non Final Office Action mailed Jun. 12, 2023", 7 pgs.
"U.S. Appl. No. 18/191,115, Notice of Allowance mailed Jul. 19, 2023", 8 pgs.
"U.S. Appl. No. 18/191,115, Response filed Jun. 28, 2023 to Non Final Office Action mailed Jun. 12, 2023", 8 pgs.
"U.S. Appl. No. 18/203,297, Examiner Interview Summary mailed Jul. 24, 2024", 2 pgs.
"U.S. Appl. No. 18/203,297, Final Office Action mailed Sep. 9, 2024", 6 pgs.
"U.S. Appl. No. 18/203,297, Non Final Office Action mailed Mar. 25, 2024", 15 pgs.
"U.S. Appl. No. 18/203,297, Non Final Office Action mailed Sep. 22, 2023", 8 pgs.
"U.S. Appl. No. 18/203,297, Notice of Allowance mailed Nov. 22, 2023", 9 pgs.
"U.S. Appl. No. 18/203,297, Response filed Mar. 5, 2024 to Restriction Requirement mailed Feb. 14, 2024", 9 pgs.
"U.S. Appl. No. 18/203,297, Response filed Aug. 21, 2024 to Non Final Office Action mailed Mar. 25, 2024", 12 pgs.
"U.S. Appl. No. 18/203,297, Response filed Oct. 3, 2023 to Non Final Office Action mailed Sep. 22, 2023", 11 pgs.
"U.S. Appl. No. 18/203,297, Restriction Requirement mailed Feb. 14, 2024", 5 pgs.
"U.S. Appl. No. 18/203,936, Non Final Office Action mailed Jan. 17, 2024", 42 pgs.
"U.S. Appl. No. 18/203,936, Non Final Office Action mailed Aug. 15, 2023", 8 pgs.
"U.S. Appl. No. 18/203,936, Notice of Allowance mailed Sep. 13, 2023", 9 pgs.
"U.S. Appl. No. 18/203,936, Response filed Sep. 5, 2023 to Non Final Office Action mailed Aug. 15, 2023", 12 pgs.
"U.S. Appl. No. 18/218,344, Non Final Office Action mailed Mar. 7, 2024", 21 pgs.
"U.S. Appl. No. 18/218,344, Non Final Office Action mailed Aug. 21, 2023", 8 pgs.
"U.S. Appl. No. 18/218,344, Notice of Allowance mailed Jun. 26, 2024", 10 pgs.
"U.S. Appl. No. 18/218,344, Notice of Allowance mailed Sep. 21, 2023", 8 pgs.
"U.S. Appl. No. 18/218,344, Response filed Jun. 4, 2024 to Non Final Office Action mailed Mar. 7, 2024", 14 pgs.
"U.S. Appl. No. 18/218,344, Response filed Sep. 12, 2023 to Non Final Office Action mailed Aug. 21, 2023", 12 pgs.
"U.S. Appl. No. 18/218,350, Non Final Office Action mailed Jan. 24, 2024", 36 pgs.
"U.S. Appl. No. 18/218,350, Non Final Office Action mailed Aug. 21, 2023", 7 pgs.
"U.S. Appl. No. 18/218,350, Notice of Allowance mailed Sep. 13, 2023", 9 pgs.
"U.S. Appl. No. 18/218,350, Response filed Sep. 5, 2023 to Non Final Office Action mailed Aug. 21, 2023", 13 pgs.
"U.S. Appl. No. 18/222,711, Non Final Office Action mailed Apr. 30, 2024", 186.
"U.S. Appl. No. 18/222,711, Non Final Office Action mailed Sep. 8, 2023", 8 pgs.
"U.S. Appl. No. 18/222,711, Notice of Allowance mailed Nov. 22, 2023", 8 pgs.
"U.S. Appl. No. 18/222,711, Response filed Oct. 2023 to Non Final Office Action mailed Sep. 8, 2023", 8 pgs.
"U.S. Appl. No. 18/242,894, Non Final Office Action mailed Jan. 31, 2024", 42 pgs.
"U.S. Appl. No. 18/243,223, Non Final Office Action mailed Feb. 5, 2024", 74 pgs.
"U.S. Appl. No. 18/243,223, Response filed Aug. 1, 2024 to Non Final Office Action mailed Feb. 5, 2024".
"U.S. Appl. No. 18/243,820, Non Final Office Action mailed Jan. 24, 2024", 47 pgs.
"U.S. Appl. No. 18/243,820, Non Final Office Action mailed Dec. 15, 2023", 8 pgs.
"U.S. Appl. No. 18/243,820, Response filed Dec. 21, 2023 to Non Final Office Action mailed Dec. 15, 2023", 10 pgs.
"U.S. Appl. No. 18/598,110, Non Final Office Action mailed Aug. 8, 2024", 15 pgs.
"U.S. Appl. No. 18/598,110, Notice of Allowance mailed Sep. 3, 2024", 7 pgs.
"U.S. Appl. No. 18/598,110, Response filed Jun. 17, 2024 to Restriction Requirement mailed May 2, 2024", 12 pgs.
"U.S. Appl. No. 18/598,110, Response filed Aug. 22, 2024 to Non Final Office Action mailed Aug. 8, 2024", 13 pgs.

(56) References Cited

OTHER PUBLICATIONS

"U.S. Appl. No. 18/598,110, Restriction Requirement mailed May 2, 2024", 6 pgs.
"U.S. Appl. No. 18/830,087, Non Final Office Action mailed Oct. 23, 2024", 13 pgs.
"European Application Serial No. 20936131.0, Extended European Search Report mailed Jun. 21, 2023", 9 pgs.
"European Application Serial No. 20936131.0, Response filed Jan. 10, 2024 to Extended European Search Report mailed Jun. 21, 2023", 57 pgs.
"European Application Serial No. 21807934.1, Extended European Search Report mailed Sep. 4, 2024", 8 pgs.
"European Application Serial No. 21807934.1, Response to Communication pursuant to Rules 161(1) and 162 EPC filed Jun. 13, 2023", 28 pgs.
"European Application Serial No. 21808856.5, Extended European Search Report mailed Sep. 18, 2023", 8 pgs.
"European Application Serial No. 21808856.5, Response filed Mar. 4, 2024 to Extended European Search Report mailed Sep. 18, 2023", 24 pgs.
"European Application Serial No. 22206766.2, Extended European Search Report mailed Mar. 22, 2023", 9 pgs.
"International Application Serial No. PCT/US2019/024054, International Preliminary Report on Patentability mailed Oct. 8, 2020", 9 pgs.
"International Application Serial No. PCT/US2019/024054, International Search Report mailed Jul. 25, 2019", 5 pgs.
"International Application Serial No. PCT/US2019/024054, Invitation to Pay Additional Fees mailed May 29, 2019", 3 pgs.
"International Application Serial No. PCT/US2019/024054, Written Opinion mailed Jul. 25, 2019", 7 pgs.
"International Application Serial No. PCT/US2020/033804, International Preliminary Report on Patentability mailed Dec. 1, 2022", 12 pgs.
"International Application Serial No. PCT/US2020/033804, International Search Report mailed Aug. 28, 2020", 3 pgs.
"International Application Serial No. PCT/US2020/033804, Written Opinion mailed Aug. 28, 2020", 10 pgs.
"International Application Serial No. PCT/US2021/016585, International Preliminary Report on Patentability mailed Dec. 1, 2022", 15 pgs.
"International Application Serial No. PCT/US2021/016585, International Search Report mailed Jun. 30, 2021", 5 pgs.
"International Application Serial No. PCT/US2021/016585, Invitation to Pay Additional Fees mailed Apr. 22, 2021", 3 pgs.
"International Application Serial No. PCT/US2021/016585, Written Opinion mailed Jun. 30, 2021", 13 pgs.
"International Application Serial No. PCT/US2021/030182, International Preliminary Report on Patentability mailed Dec. 1, 2022", 19 pgs.
"International Application Serial No. PCT/US2021/030182, International Search Report mailed Aug. 16, 2021", 2 pgs.
"International Application Serial No. PCT/US2021/030182, Written Opinion mailed Aug. 16, 2021", 17 pgs.
Nishidate, I, et al., "Evaluation of arterial oxygen saturation using RGB camera-based remote photoplethysmography", InOptical Diagnostics and Sensing XVIII: Toward Point-of-Care Diagnostics, (Feb. 20, 2018), 208-214.
Secerbegovic, Alma, et al., "Blood pressure estimation using video plethysmography", IEEE 13th international symposium on biomedical imaging (ISBI), (2016), 4 pgs.
Sharidan, Parr K, et al., "Automated mapping of laboratory tests to LOINC codes using noisy labels in a national electronic health record system database", Journal of the American Medical Informatics Association 25, (2018), 1292-1300.
"U.S. Appl. No. 18/203,297, Notice of Allowance mailed Nov. 26, 2024", 12 pgs.
"U.S. Appl. No. 18/203,297, Response filed Nov. 11, 2024 to Final Office Action mailed Sep. 9, 2024", 11 pgs.
"U.S. Appl. No. 18/830,087, Examiner Interview Summary mailed Nov. 25, 2024", 2 pgs.

\* cited by examiner

RELOCATION MODULE AND METHODS FOR SURGICAL EQUIPMENT

PRIORITY

This application is a continuation of U.S. application Ser. No. 18/598,110, filed Mar. 7, 2024, which is a continuation of U.S. application Ser. No. 18/142,787, filed May 3, 2023, now issued as U.S. Pat. No. 12,023,281, which is a continuation of U.S. application Ser. No. 18/099,074, filed Jan. 19, 2023, which is a continuation of U.S. application Ser. No. 17/874,963, filed Jul. 27, 2022, now issued as U.S. Pat. No. 11,648,166, which is a continuation of U.S. application Ser. No. 17/873,857, filed Jul. 26, 2022, now U.S. Pat. No. 11,654,070, which is a continuation of U.S. application Ser. No. 17/528,832 filed Nov. 17, 2021, now issued as U.S. Pat. No. 11,432,982, which is a continuation-in-part of U.S. application Ser. No. 17/376,469 filed Jul. 15, 2021, now issued as U.S. Pat. No. 11,219,570, which is a continuation-in-part of U.S. application Ser. No. 17/199,722 filed Mar. 12, 2021, now issued as U.S. Pat. No. 11,173,089, which is a continuation of U.S. application Ser. No. 17/092,681, filed Nov. 9, 2020, now issued as U.S. Pat. No. 10,993,865, which is a continuation of U.S. application Ser. No. 16/879,406, filed May 20, 2020, now issued as U.S. Pat. No. 10,869,800, which is a continuation-in-part of U.S. application Ser. No. 16/601,924, filed Oct. 15, 2019, now issued as U.S. Pat. No. 10,702,436, which is a continuation of U.S. application Ser. No. 16/593,033, filed Oct. 4, 2019, now issued as U.S. Pat. No. 10,653,577, which is a continuation of U.S. application Ser. No. 16/364,884, filed Mar. 26, 2019, now issued as U.S. Pat. No. 10,507,153, which claims the benefit of priority to U.S. Provisional Patent Application 62/782,901, filed Dec. 20, 2018. U.S. application Ser. No. 16/364,884, filed Mar. 26, 2019, now issued as U.S. Pat. No. 10,507,153 is also a continuation-in-part of U.S. application Ser. No. 15/935,524, filed Mar. 26, 2018, now issued as U.S. Pat. No. 10,512,191.

U.S. application Ser. No. 17/376,469, now U.S. Pat. No. 11,219,570, is also a continuation-in-part of U.S. application Ser. No. 17/245,942, filed Apr. 30, 2021, now U.S. Pat. No. 11,426,318, which is a continuation-in-part of U.S. application Ser. No. 17/167,681, filed Feb. 4, 2021, now issued as U.S. Pat. No. 11,160,710, which is a continuation-in-part of U.S. application Ser. No. 17/092,681, filed Nov. 9, 2020, now issued as U.S. Pat. No. 10,993,865, which is a continuation of U.S. application Ser. No. 16/879,406, filed May 20, 2020, now issued as U.S. Pat. No. 10,869,800.

The disclosures of each of these applications is incorporated herein by reference in its entirety.

TECHNICAL FIELD

This document pertains generally, but not by way of limitation, to systems and methods for improving safety in operating rooms and hospitals. In particular, the systems and methods described herein may include but are not limited to, anesthetic, surgical and medical equipment storage and operational data capture, automated anesthetic and patient monitoring data capture and electronic record input.

BACKGROUND

Anesthesia monitors and equipment as well as surgical equipment have been invented, developed and sporadically introduced into surgical practice over more than a century. This equipment is made by a wide variety of companies who have no incentive to coordinate with one another to create the most efficient operating room. Equipment throughout the operating room has been placed in one location or another, generally without a plan and then decades later, is still sitting in that unplanned location.

Over the past 20 years, there has been a gradual movement to replacing paper anesthetic records with electronic anesthetic records (EAR). The digital electronic data outputs of the patient's physiologic monitors have been relatively easy to input into the EAR. However, the identity, dosing and timing of IV and inhaled drug administration, IV fluid administration, oxygen and ventilation gas administration and anesthetic events such as intubation have required manual input to the EAR by way of a computer keyboard and mouse. Blood, fluid and urine outputs have also required manual input to the EAR by way of a computer keyboard and mouse. The surgical equipment scattered around the operating room either does not produce a digital output that could memorialize the equipment's operation to the electronic record, that output is not automatically captured, or the output is not provided in a way that provides meaningful context.

Carefully observing the patient in various conditions and situations including surgery has been an important source medical information for centuries. However, in this age of electronic monitoring, patient observation by the healthcare provider is becoming a lost art that is infrequently done and if it is done it may not be entered into the record so the information is lost.

Most electronic medical equipment, especially equipment constituting dose events, do not produce an electronic data record documenting the equipment's operating parameters. A complete electronic health record (EHR) requires instant documentation of all dose events in order to allow meaningful clinical decision support (CDS) and AI analysis of dose and response events.

The concept of "garbage in, garbage out" is of the utmost importance for medical algorithms trained on healthcare datasets. The majority of data categories in the acute care setting are manually inputted, basically a digitized paper record. Manually inputted data is sporadic and prone to errors and omissions. It is also not time-stamped for temporal correlations. The result is that when those data are aggregated into a "big data" database, the data is incomplete, inconsistent, missing and often unusable. Further, clinicians hate the data entry part of their jobs, seeing it as time consuming and distracting from patient care. Several studies have linked manual data entry to the electronic record as a significant contributor to physician burnout.

SUMMARY

In some examples, the automated data consolidation module of this disclosure minimizes "garbage in" of healthcare "big data" by automating the data input process.

As a result of the current medical practices described, the majority of the input to the electronic anesthetic and medical records has been the data from the vital signs monitors, recording the patient's "response." The "dose" events (things that are given or done to the patient leading to the "response") are manually entered into the record, resulting in mistakes, omissions and no temporal correlation between the dose and response. The incomplete and inaccurate records make any analysis with artificial intelligence and machine learning software problematic, either for that individual patient or for "big data" analysis of populations of patients.

This document pertains generally to systems and methods for improving safety for patients receiving intravenous (IV) medications and fluids, by avoiding medication or fluid errors and documenting the administration. This document pertains generally, but not by way of limitation, to systems and methods for constructing granular (beat-by-beat) anesthetic, surgical and patient records that include both "dose" events (things that are given or done to the patient) and "response" events (inputs from electronic monitors, measurement devices and machine vision "observations"). The dose and response events are precisely temporally related and recorded in the patient's electronic record and may be pooled with the records of other patients in a database that can be analyzed with artificial intelligence and machine learning software.

Illustrative examples of an automated data consolidation module that systematizes surgical safety for patients and OR personnel. In some examples, this automated data consolidation module is designed to house nearly all of the operating room patient monitors and support equipment. Even dissimilar types of equipment that are normally kept separate from one another. In some examples, this unique automated data consolidation module is specially designed to fit next to and under the arm-board of the surgical table—a location traditionally occupied by an IV pole. For the past 100 years, this location has been a wasted "no-man's land" between the anesthesia and surgical sides of the operating room. In reality, the unique space next to and under the arm-board, is truly the "prime real estate" of the entire operating room: it is immediately adjacent the patient for optimal monitoring while simultaneously maintaining observation of the patient and surgical procedure; equipment controls can be conveniently accessed by both the anesthesia and surgical staff; short cables and hoses are adequate to reach the patient; and it is uniquely accessible from both the anesthesia and surgical sides of the anesthesia screen. The unique space next to and under the arm-board is the only location in the entire operating room where cables, cords and hoses from both the anesthesia side and the sterile surgical field side, do not need to traverse the floor or even touch the floor in order to connect to their respective monitor or patient support equipment-truly a remarkable location that has been wasted by conventional systems.

In some examples, an illustrative automated data consolidation module can house both anesthesia related and non-anesthesia related equipment. In some examples, the illustrative relocation module can house a variety of non-proprietary OR equipment such as patient vital sign monitors, electro-surgical generators, anesthesia machines and mechanical ventilators. In some examples, the automated data consolidation module is designed to also house newer proprietary safety equipment such as: air-free electric patient warming, surgical smoke evacuation, waste alcohol and oxygen evacuation, evacuation of the flow-boundary dead-zones that cause disruption of the OR ventilation and the evacuation and processing of waste heat and air discharged from OR equipment. In some examples, this automated data consolidation module may also house dissimilar equipment (e.g., unrelated to anesthesia monitoring) such as: air mattress controls and air pumps; sequential compression legging controls and air pumps; capacitive coupling electrosurgical grounding; RFID counting and detection of surgical sponges; the waste blood and fluid disposal systems; and "hover" mattress inflators. Any of these devices may be stored in the automated data consolidation module together with (or without) anesthesia equipment.

In some examples, the automated data consolidation module is a specialized and optimally shaped rack for holding and protecting the patient monitors and other electronic and electromechanical surgical equipment, in a unique location. A location that is very different from just setting anesthesia monitors on top of the anesthesia machine and scattering other equipment across the floor of the operating room. The automated data consolidation module may be used anywhere throughout the hospital or long term care settings.

The various pieces of electronic and electromechanical equipment housed within the automated data consolidation module disclosed herein can produce relatively large amounts of waste heat. In some examples, the automated data consolidation module may include a waste heat management system to safely dispose of the waste heat created by the electronic and electromechanical equipment housed within the automated data consolidation module.

It would be difficult or even impossible to manage the uncontained waste heat produced by electronic and electromechanical equipment mounted on a simple open rack because it can escape in any direction. In some examples, the module can include a "cowling" covering some or all of the outer surface. The cowling not only protects the equipment from accidental fluid damage but also confines the waste heat from the electronic and electromechanical equipment mounted within the module, to the inside of the module and cowling. In some examples, the confined waste heat can then be safely managed.

In some examples, the cowling cover of the automated data consolidation module can form or support a waste heat management system. In some examples, the cowling can be provided on an inner surface of the housing. In some examples, the cowling can be described as an insulation. In some examples, the housing can include other types of insulation from heat and/or water. Any suitable type of insulated housing suitable for use in a surgical field can be provided.

In some examples, the automated data consolidation module of the instant invention may also contain the components of the anesthesia gas machine. So-called "gas machines" are relatively simple assortments of piping, valves, flow meters, vaporizers and a ventilator. These could be located within the automated data consolidation module or attached to the automated data consolidation module for further consolidation of equipment and for improved access to the patient.

In some examples, locating the anesthesia machine in or on the automated data consolidation module allows direct access for and sensors and monitors related to the anesthesia machine, to input data to the electronic anesthetic record being recorded by equipment in the automated dose/response record system.

In some examples, the collection canisters for waste fluid and blood may be conveniently mounted on the module.

In some examples, the controls and display screens for the surgical equipment housed in the automated data consolidation module may be wirelessly connected to a portable display screen such as an iPad or "smart tablet," for convenient access by the nurse anywhere in the room. A remote display screen can also allow remote supervision and consultation.

In some examples the automated data consolidation module may be located next to the patient's bed in the ICU, ER, on the ward or in long term care. While most of the data collected by the automated data consolidation module will occur in the acute care setting, it should be understood that the automated data consolidation module concept for automatically collecting and consolidating data from a wide variety of data sources including monitors and other medical equipment, can be applied throughout the healthcare delivery system.

Doctors and nurses dislike record keeping and the switch to the electronic record has made the act of record keeping more difficult and time consuming. Entering the electronic record into the computer sometime after the event occurred and the case has settled down, is not only distracting from patient care but leads to inaccurate records. Hand entered records also bypass the opportunity for the computer to add to patient safety by checking drug identities, dosages, side effects, allergies and alerting the clinician to potential problems or even physically stopping the drug administration. Manually entered records are not useful for managing drug inventories because a given medication administration is not tied to a specific drug bottle or syringe. Finally, the computer mouse and keyboards have been shown to be contaminated by a wide variety of infective organisms and are virtually impossible to clean. Automatic anesthetic data entry to the EAR would improve patient safety, improve clinician job satisfaction and improve OR inventory management.

In general, doctors and nurses are not interested in replacing themselves and their jobs with automated drug delivery or automated anesthesia systems. However, they may be more open to automated record keeping. The challenge with automated record keeping is automating the data input that documents the numerous activities, anesthesia related events, fluid, gas and medication administration that constitute an anesthetic experience or another medical situation.

The second challenge in implementing an automated electronic anesthetic record (EAR) or automated electronic medical record (EMR) is to force as little change in routine as possible onto the anesthesiologist and other clinicians using this system. Anesthesiologists and surgeons are notoriously tradition-bound and resistant to any changes in their "tried and true" way of doing things. Therefore, a successful automated EAR must interact seamlessly with current anesthesia practices and operating room workflow without causing any disruptions.

In some examples, the automated data consolidation module of this disclosure includes a system for automatically measuring and recording the administration of IV medications and fluids. The system for automatically measuring and recording the administration of IV medications and fluids can include one or more sensors, such as one or more of a barcode reader and an RFID interrogator for accurately identifying a medication or fluid for IV administration.

In some examples, the system for automatically measuring and recording the administration of IV medications and fluids can also include one or more digital cameras with machine vision software ("machine vision") for accurately measuring the volume of medication administered from a syringe or fluid administered from an IV bag through a drip chamber into an IV tubing. The digital cameras with machine vision software essentially duplicate the clinician's vision of an activity, injection of a drug from a syringe for example, without interfering in the normal activity and yet allows automatic recording of the activity in the EAR. The machine vision software can include one or more machine-readable mediums that when implemented on hardware processing circuitry of the system or in electrical communication with the system, can perform the functions described herein.

In some examples, the automated data consolidation module of this disclosure uses machine vision to unobtrusively "observe" the flow rate of the ventilation gas flow meters and inhaled anesthetic vaporizers.

In some examples, the automated data consolidation module of this disclosure captures input data from the blood and fluid collection and urine output collection systems of this disclosure.

In some examples, the automated data consolidation module of this disclosure lets the computer (e.g., a processor and memory for performing instructions) add to patient safety by checking drug identities, dosages, side effects, allergies, the patients' medical history and vital signs and alerting the clinician to potential problems or even physically stopping the drug administration. In some examples, the automated data consolidation module of this disclosure eliminates medication errors by checking the drug to be injected against the physician's medication orders before the injection can occur. In some examples, the automated data consolidation module of this disclosure is useful for managing drug inventories because a given medication administration is tied to a specific drug bottle or syringe.

In some examples, the automated data consolidation module of this disclosure may also automatically record and display many other functions including but not limited to: IV fluid administration, medication infusions, the patient's vital signs, urine output, blood loss, ventilator settings, inspired gases, electrosurgical settings, pneumoperitoneum insufflation settings, RFID surgical sponge counts, surgical information and video, dialysis or other medical procedure information and patient activity.

"Dose/response" is one of the most basic of all medical processes. Since the beginning of medical practice, both the art and science of medicine have relied on giving something to the patient (a medicine for example) or doing something to the patient (mechanical ventilation or surgery for example)—the "dose", and then observing the patient's "response." The problem now seen with electronic records is that the only data that is timely recorded is the "response" data provided by the physiologic monitors. Even that response data is frequently not recorded beat-by-beat but rather intermittently recorded every 5 minutes or 30 minutes or 4 hours for example. All of the "dose" data is entered into the electronic record by hand and therefore is prone to mistakes, omissions and unknown timing. Therefore, with current EMRs, the dose and response data cannot be temporally correlated with any accuracy, vastly reducing the analytical and predictive value of the electronic database and record.

In some examples, the automated data consolidation module of this disclosure includes systems and methods for constructing granular (beat-by-beat, second-by-second) anesthetic, surgical and patient records that include both "dose" events—the things that are given or done to the patient (inputs from medication injection and fluid monitors, various support equipment and machine vision "observations" for example) and "response" events (inputs from electronic monitors, measurement devices and machine vision "observations" for example). In some examples, the invention of this disclosure automatically enters both dose and response events into the electronic record. In some examples, the invention of this disclosure automatically enters both dose and response events into the electronic record and temporally correlates the dose and response events, such as but not limited to, when they are recorded. In some examples, the automatically entered, temporally correlated dose and response events in the patient's electronic record may be analyzed by artificial intelligence (AI) and/or machine learning (ML) software stored in a memory of a storage device electrically coupled to the processing circuitry of the module for immediate advice, alerts and feedback to the clinician. In some examples, the automatically entered, temporally correlated dose and response events in the patient's electronic record may be pooled with the records of other patients in a database that can be analyzed with artificial intelligence and machine learning software.

Machine Learning (ML) is an application that provides computer systems the ability to perform tasks, without explicitly being programmed, by making inferences based on patterns found in the analysis of data. Machine learning explores the study and construction of algorithms (e.g., tools), that may learn from existing data and make predictions about new data. Such machine-learning algorithms operate by building an ML model from example training data, in order to make data-driven predictions or decisions expressed as outputs or assessments. The principles presented herein may be applied using any suitable machine-learning tools.

In some examples, the AI or ML software can compare dose and response events from different periods of time for the same patient to learn and identify the particular patient's responses. In some examples the machine learning software can be trained to identify a patient's responses using training obtained from a plurality of patients that may include or not include the patient being monitored. Any suitable AI or ML can be implemented to interpret the data generated by the module. Current methods of obtaining data in medical settings cannot generate, store or aggregate such data for analysis using AI or ML. Thus, the dose-response systems described herein provide a technical solution to a technical problem.

Machine vision cameras and software are very good at measuring distances, movements, sizes, looking for defects, fluid levels, precise colors and many other quality measurements of manufactured products. Machine vision cameras and software can also be "taught" through AI and ML to analyze complex and rapidly evolving scenes, such as those in front of a car driving down the road.

In some examples, the automated data consolidation module of this disclosure includes novel systems and methods for using portable machine vision cameras and software to "observe" the operating parameters of various dose event and other equipment. In some examples, the automated data consolidation module of this disclosure includes novel systems and methods for using portable machine vision cameras and software to "observe" the response parameters of various response event equipment. In some examples, the portable machine vision cameras may include: laser pointers to aid in aiming and coded labels on the items or devices to be identified to aid in ML identification. In some examples, the laser pointers and coded labels help to structure the scene so that ML can be simplified.

In some examples, the automated data consolidation module of this disclosure includes novel systems and methods for using machine vision cameras and software to "observe" the patient. If the patient is in surgery, the patient's head may be the focus of the observation. In some examples, during surgery the machine vision cameras and software may be "looking" for dose events including but not limited to mask ventilation or endotracheal intubation. In some examples, during surgery the machine vision cameras and software may be "looking" for response events including but not limited to grimacing or tearing or coughing or changes in skin color.

If the patient is on the ward or in the nursing home or other long-term care facility, the whole patient may be the focus of the observation. In some examples, if the patient is on the ward or in the nursing home or other long-term care facility the machine vision cameras, processing circuitry and software may be configured to "look" for dose events (e.g., sense) including but not limited to repositioning the patient, suctioning the airway or assisting the patient out of bed or any other nursing procedure, eating and drinking. In some examples, if the patient is on the ward or in the nursing home or other long-term care facility (including at home) the machine vision cameras, processing circuitry and software may be configured to "look" for response events (e.g., sense) including but not limited to restlessness or getting out of bed without assistance or coughing or breathing pattern. In some examples, the system can go beyond traditional physiologic monitors. Even physiologic response information such as pain may be detected by facial expression analysis.

In some examples, vital signs such as heart rate, respiration rate, blood oxygen saturation and temperature can be measured (e.g., sensed, monitored) remotely via camera-based methods. Vital signs can be extracted from the optical detection of blood-induced skin color variations—remote photoplethysmography (rPPG).

In some examples, the automated data consolidation module may allow remote viewing of the displayed patient information. In some examples, the remotely displayed patient information may be used for remote medical supervision such as an anesthesiologist providing remote supervision to a nurse anesthetist who is administering the anesthetic. In some examples, the remotely displayed patient information may be used for remote medical consultation. In some examples, the remotely displayed patient information may be used to document the involvement of remote medical supervision or consultation for billing purposes.

In some examples, the automated data consolidation module allows rules to be applied to the various medical equipment that is housed within the module, mounted on the module, or is in electrical communication with or in wireless communication with the module. In some examples, the rules can include one or more of the following: that all equipment produce data reflecting the equipment's operating parameters and sensor inputs, the data is produced in prescribed data formats, the data include all prescribed input record fields for that specific type of equipment, the data is instantly and continuously provided.

In some examples, the automated data consolidation module includes processing circuitry and software that accept the data inputted from the various medical equipment. In some examples, the processing circuitry and software can translate data that is not inputted in the prescribed format. In some examples, the processing circuitry and software can add time stamps to the data to add a temporal context. In some examples, the processing circuitry and software can do data "filtering" in the presence of large size data to discard information that is not useful for healthcare monitoring based on a defined criterion. This may include for example, intermittently recording data that changes slowly such as the patient's temperature, rather than continuously recording. In some examples, the processing circuitry and software can do data "cleaning" such as normalization, noise reduction and missing data management. Sensor fusion is a technique that may be utilized to simultaneously analyze data from multiple sensors, in order to detect erroneous data from a single sensor. In some examples, the processing circuitry and software can be used in many other ways to cleanse, organize and prepare the input data.

In some examples, the processing circuitry and software execute "stream processing" for applications requiring real-time feedback. In some examples, streaming data analytics in healthcare can be defined as a systematic use of continuous waveform and related medical record information developed through applied analytical disciplines, to drive decision making for the patient care.

In some examples, when the objective is to deliver data to a "big data" database, the data must be pooled. Data in the "raw" state needs to be processed or transformed. In a service-oriented architectural approach, the data may stay raw and services are used to call, retrieve and process the data. In the data warehousing approach, data from various sources is aggregated and made ready for processing, although the data is not available in real-time. The steps of extract, transform, and load (ETL) can be used to cleans and ready data from diverse sources.

In some examples, with "big data" database data, the processing circuitry and software may execute "batch processing," analyzing and processing the data over a specified period of time. Batch processing aims to process a high volume of data by collecting and storing batches to be analyzed in order to generate results. In some examples, the processing circuitry and software can serve as a "node" in batch computing, where big data is split into small pieces that are distributed to multiple nodes in order to obtain intermediate results. Once data processing by nodes is terminated, outcomes will be aggregated in order to generate the final results.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various examples discussed in the present document. Any combination of the features shown and described in this disclosure, including combinations of fewer or more features is within the content of this disclosure. Modules, systems and methods including individual features described herein, without combinations of features as shown in the examples (for the sake of brevity), are also within the scope of this disclosure.

DETAILED DESCRIPTION

The following detailed description is exemplary in nature and is not intended to limit the scope, applicability, or configuration of the invention in any way. Rather, the following description provides practical illustrations for implementing exemplary examples of the present invention. Examples of constructions, materials, dimensions, and manufacturing processes are provided for selected elements, and all other elements employ that which is known to those of skill in the field of the invention. Those skilled in the art will recognize that many of the examples provided have suitable alternatives that can be utilized.

As described herein, operably coupled can include, but is not limited to, any suitable coupling, such as a fluid (e.g., liquid, gas) coupling, an electrical coupling or a mechanical coupling that enables elements described herein to be coupled to each other and/or to operate together with one another (e.g., function together).

"Dose/response" can be a useful medical tool. Dose/response involves giving something to the patient (a medicine for example) or doing something to the patient (mechanical ventilation or surgery for example)—the "dose", and then observing the patient's "response."

Throughout this disclosure, the word "dose" or "dose event" means something that was given to or done to the patient. In some examples, "dose events" involve giving something to the patient including but not limited to: the injection or ingestion of medications, the infusion of medications, the infusion of IV fluids, inspired gases such as oxygen or nitrous oxide or volatile anesthetics or nitric oxide.

In some examples, "dose events" are things done to the patient, including but not limited to: mask ventilation, tracheal intubation, mechanical ventilation, pneumoperitoneum insufflation, patient positioning and surgery.

In some examples, "dose events" are applications of electricity to the patient, including but not limited to: train-of-four determination of muscle relaxation, nerve conduction studies, cardiac pacing, cardioversion, electrical stimulation of nerves and electroconvulsive therapy. Many other "dose events" are anticipated.

Throughout this disclosure, the word "response" or "response event" means a physiologic, reflexive motor response or volitional motor response from the patient. In some examples, "response events" involve measuring a physiologic response of the patient measured by the physiologic monitors, including but not limited to: an electrocardiogram (EKG), pulse oximetry, blood pressure, end tidal gases, electroencephalogram (EEG), bispectral index (BIS), laboratory blood studies, urine output, blood loss and pulmonary compliance.

In some examples, "response events" involve measuring a motor response of the patient, including but not limited to: a train-of-four, grimacing, coughing, movements of many sorts and tearing, that may be measured by a machine vision camera and software.

Figure 1:
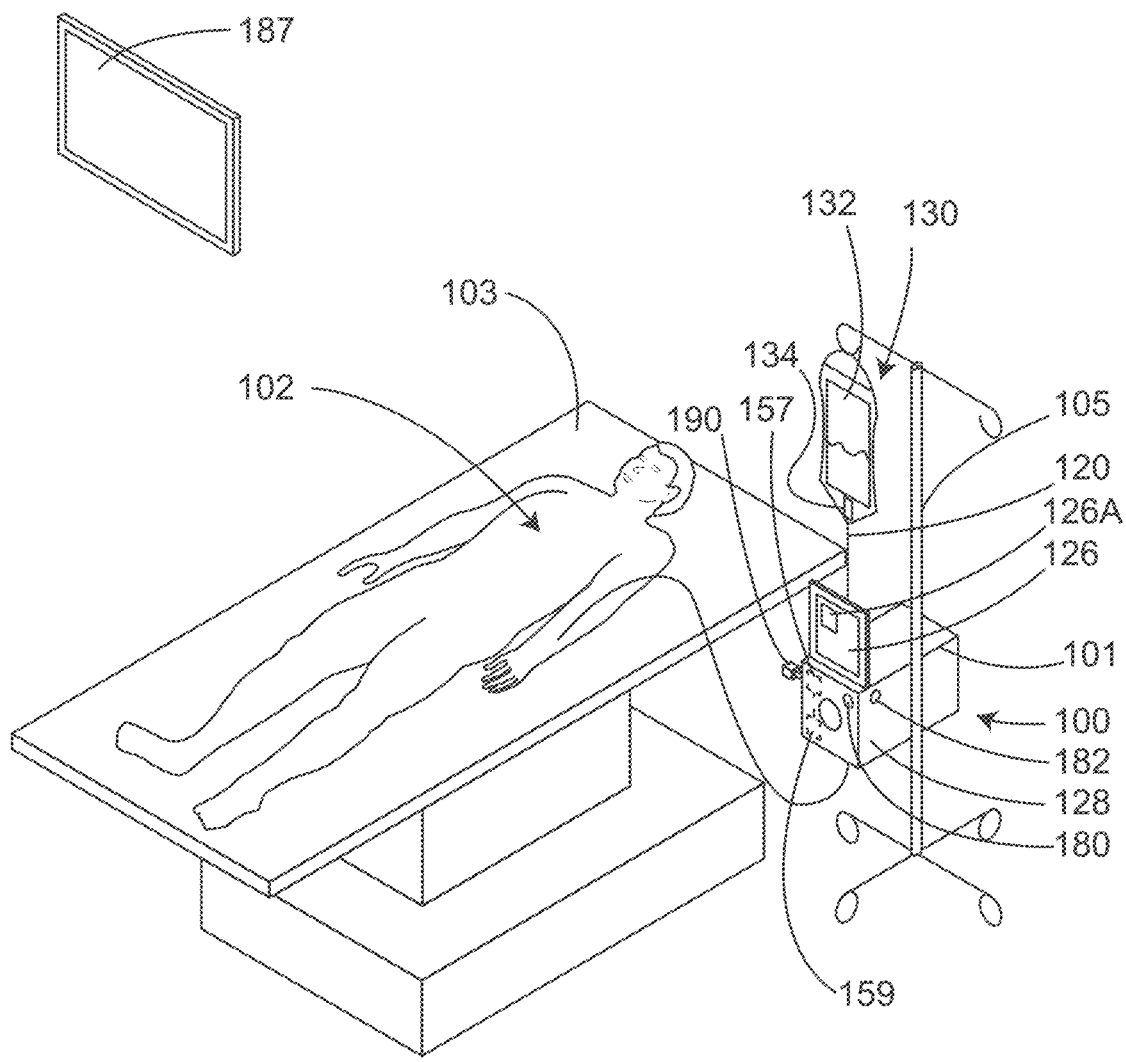
FIG. 1 illustrates an isometric view of an example module including a system for generating an automated electronic anesthetic record located proximate to a patient, in accordance with at least one example of this disclosure.

FIG. 1 illustrates an isometric view of an example automated data consolidation module 100 for generating an automated electronic anesthetic record (EAR) or electronic medical record (EMR) located proximate to a patient. Some aspects of FIG. 1 are also described with respect to the description of other figures, including FIG. 14.

As shown in FIG. 1, the automated data consolidation module 100 may be attached to and portions can be stored within a module 101. The module 101 can conveniently provide direct access to the patient 102. An IV pole 105 may provide a convenient mounting support location for the automated data consolidation module for IV medications 100 (hereinafter, "automated data consolidation module 100"). In some examples, the components and systems of the automated data consolidation module 100 of this disclosure can be supported by other mounting supports, including but not limited to a boom-mounted rack system, a wheeled rack system and a bed 103 mounting bracket. One or more computers including processing circuitry 157, of the automated data consolidation module 100 of this disclosure may be conveniently and safely housed inside the module 101.

In some examples, it is anticipated that some or all of the components of the automated data consolidation module 100 of this disclosure could be used in other healthcare settings such as the intensive care unit, the emergency room or on the ward. As shown in FIG. 1, the module 101 may be mounted on an IV pole 105 or other suitable mounting structure located near the patient 102.

In some examples, a touch-screen electronic record display 126 can convert to a qwerty-type keyboard to allow uncommon anesthetic and surgical events or deviations from pre-recorded scripts, to be manually documented. In some examples, natural language speech recognition software may be included in the processing circuitry 157 allowing the operator to simply dictate the record. This allows the standard computer keyboard that is used for data entry in most electronic anesthetic records, to be eliminated. Standard keyboards are known to be contaminated with pathogenic organisms and are nearly impossible to clean and decontaminate due to their irregular surfaces. In contrast, the smooth glass or plastic face of a touch-screen monitor is easy to clean with no crevasses to hide organisms.

In some examples, the automated data consolidation module for IV medications 100 of this disclosure can include a system for automatically measuring and recording the administration of IV medications. In some examples, the system for automatically measuring and recording the administration of IV medications includes a medication identification and measurement system 128. In some examples, aspects of the automated data consolidation module 100 can be provided together with or separately from other aspects of the IV medication identification and measurement system 128 (hereinafter, "medication identification and measurement system 128"). Likewise, aspects of the medication identification and measurement system 128 can be provided together with or separately from other aspects of the automated data consolidation module 100.

Figure 2:
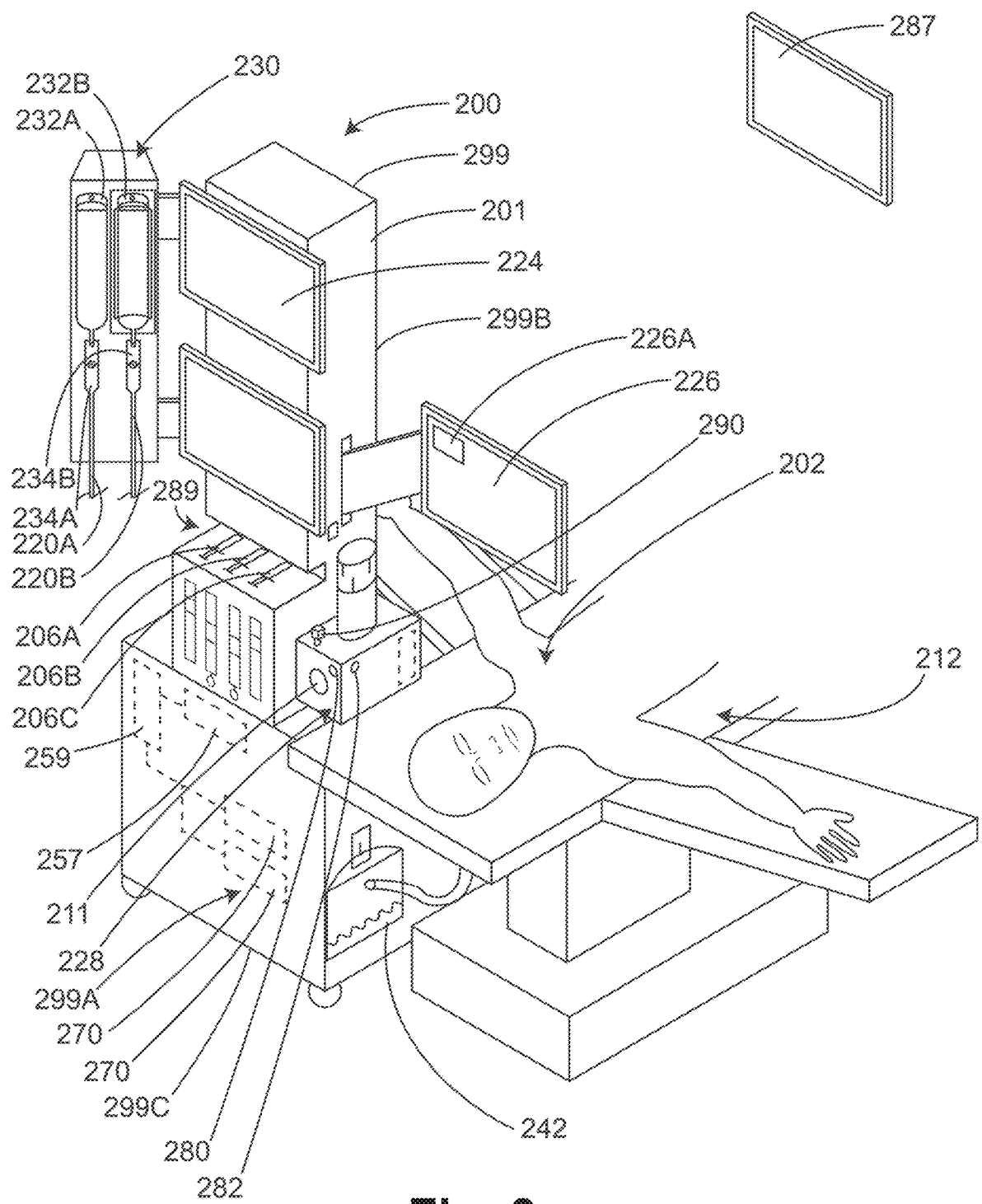
FIG. 2 illustrates an isometric view of an example module including a system for generating an automated electronic anesthetic record located proximate to a patient, in accordance with at least one example of this disclosure.

FIG. 2 illustrates an isometric view of an example automated data consolidation module 200 for generating an automated electronic anesthetic record located proximate to a patient 202. Features of the automated data consolidation module 100 of FIG. 1 may be included in the automated data consolidation module 200 of FIG. 2, and vice-versa, therefore all aspects may not be described in further detail. Like numerals can represent like elements. Aspects of FIGS. 1 and 2 may also be described together. Some aspects of FIG. 2, including an IV fluid identification and measurement system 130, are described with respect other figures, including the description of IV fluid identification and measurement system 1430 of FIG. 14.

As shown in FIG. 2, an example medication identification and measurement system 228 may be attached to a relocation module 201 that may be advantageously positioned proximate the patient 202, such as near the patient's head on a surgical table 212. In this position medications can be conveniently administered by medical personnel while also tending to and observing the patient 202 during surgery.

It would be difficult or even impossible to manage the uncontained waste heat produced by electronic and electromechanical equipment mounted on a simple open rack because it can escape in any direction. In some examples, the automated data consolidation module 100,200 can include a cowling (e.g., 299C; FIG. 2) covering substantially the entire outer surface of the housing 299. The cowling 299C not only protects the equipment from accidental fluid damage but also confines the waste heat from the electronic and electromechanical equipment mounted within the automated data consolidation module 100,200 to the inside of the module 201 and cowling 299C. In some examples, the confined waste heat can then be safely managed.

In some examples, the cowling 299C cover of the automated data consolidation module 100,200 can form or support a waste heat management system. In some examples, the cowling 299C can be provided on an inner surface of the housing 299. In some examples, the cowling 299C can be described as an insulation. In some examples, the housing 299 can include other types of insulation from heat and/or water. Any suitable type of insulated housing suitable for use in a surgical field can be provided.

In some examples, the medication identification and measurement system 128 (FIG. 1), 228 (FIG. 2) may include one or more sensors, such as one or more of: a barcode reader or QR code reader (e.g., 436, FIG. 4), a radio-frequency identification (RFID) interrogator (e.g., 438, FIG. 4), or any other suitable sensor for accurately and reliably identifying a medication for IV administration. As defined herein, a barcode reader can include any other type of identifying reader, such as, but not limited to, a QR code reader. Likewise, the RFID interrogator can be any type of interrogator and is not limited to those interrogators based on radio frequency. Examples of such sensors are described herein, such as in FIGS. 4 and 5.

In some examples, instead of, or in addition to one or more of an RFID interrogator 438 and a barcode reader 436, the medication identification and measurement system 128, 228 can receive an input to determine the identity. For example, the medication identification and measurement system 128, 228 can include one or more of: a sensor, such as barcode reader 436 of FIG. 4, configured to identify the one or more IV medications or fluids, or an input configured to receive the identity of the one or more IV medications or fluids, such as via the anesthetic record input component 224.

In some examples, the barcode reader (e.g., 436, FIG. 4) may be a "computer vision" or "machine vision" camera with the capability of reading barcodes. The term "machine vision" is often associated with industrial applications of a computer's ability to see, while the term "computer vision" is often used to describe any type of technology in which a computer is tasked with digitizing an image, processing the data it contains and taking some kind of action. In this disclosure the terms "machine vision" and "computer vision" may be used interchangeably. Traditionally, machine vision includes technology and methods used to provide imaging-based automatic inspection and analysis, process control, and robot guidance. Machine vision is sometimes used in manufacturing environments. Machine vision refers to many technologies, software and hardware products including processing circuitry, integrated systems and methods.

The inventors have discovered that machine vision can be useful beyond its traditional uses. The inventors discovered that machine vision can be advantageous in implementing an automated data consolidation module 100, 200 because it offers reliable measurements, gauging, object recognition, pattern recognition and liquid fill level measurements. Machine vision does not get tired or distracted. Machine vision excels at quantitative measurement of a structured scene because of its speed, accuracy and repeatability. However, it may require the scene to be structured to perform the desired function.

Machine vision can be very accurate for measuring size of an object at a known distance or the distance of an object of known size. However, it cannot do both. Therefore, in some examples it is important to know the exact location of a syringe (e.g., 406, FIG. 4) and thus know the distance from the camera (e.g., 436, FIG. 4) to the syringe (e.g., 406, FIG. 4) in order for the machine vision to calculate the distance of the movement of the plunger (e.g., 446, FIG. 5) within the syringe (e.g., 406, FIG. 5). This is what we mean by the "scene being structured."

Machine vision may be advantageous for the automated data consolidation module 100, 200 of this disclosure because it "sees" and measures, but does not touch or interfere with the healthcare provider doing their normal job of injecting medications or administering IV fluids. Further, the same visual image that is used by the machine vision software can be transmitted and displayed on a screen 126, 226 to give the operator (whose fingers can be pushing the plunger 446 of the syringe 406, a close-up view of the syringe 406. FIG. 5 is a cross-section view taken at 5-5 of FIG. 4. The machine vision camera 436 can be looking at the same view of the syringe 406 as the operator and it is the same or similar view that the operator would see if they were injecting IV medications the traditional way.

The machine vision camera, or digital camera, can include machine vision software, or the machine vision camera can be in electrical communication with (e.g., operably coupled to) one or more hardware processors, such as processing circuitry 157, 257 and one or more machine-readable mediums 159, 259. The one or more machine-readable mediums 159, 259 can include instructions (e.g., software), that when implemented on the processing circuitry 157, 257, can perform the functions described herein. The processing circuitry 157, 257 can be stored in the module 101, relocation module 201 or remote from the modules 101, 201 (e.g. in a wired or wireless manner). The one or more machine-readable mediums 159 can be a storage device, such as a memory located in the module 201 or remote from the module 101, 201.

In some examples, the RFID interrogator 438 may be either High Frequency (HF) or Near Field (NF) RFID in order to advantageously limit the read-range to a distance of less than 12 inches. In some examples, the RFID read-range may advantageously be limited, such as to less than 8 inches so that only a specific medication injection is identified at any time. In a possibly more preferred example, the RFID read-range may be limited to less than 4 inches to further prevent mis-readings. NF-RFID has a short read-range by definition and the read-range of HF-RFID can be easily limited by restricting the size of the antenna on the tag. In contrast, longer read-range RFID such as Ultra-high Frequency (UHF-RFID) may confusingly interrogate every RFID tag in the operating room and thus be unable to identify which medication is being delivered to the medication identification and measurement system 128, 228. However, any suitable RFID range for a particular application may be used.

Figure 3:
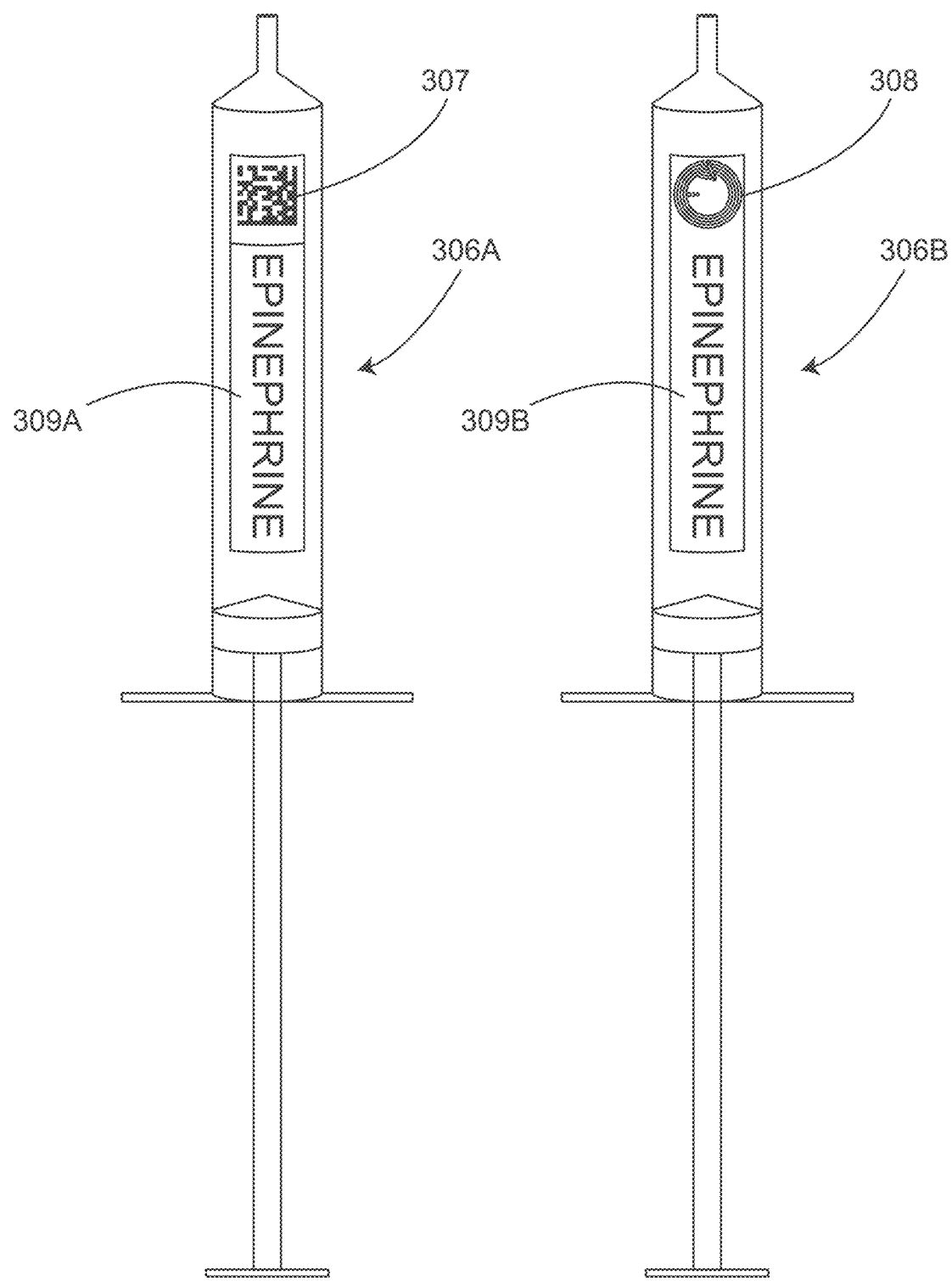
FIG. 3 illustrates a plan view of an example of preloaded syringes that can be used with the system of FIGS. 1 and 2, in accordance with at least one example of this disclosure.

FIG. 3 illustrates a plan view of an example of preloaded syringes 306A and 306B that can be used with the automated data consolidation module 200 of FIG. 2.

The one or more preloaded syringes 306A and 306B may be labeled with a unique barcode label 307 or an RFID tag 308 that may identify one or more of the drug, the concentration, the lot number, the expiration date, the manufacturer and other important information. In some examples, a unique barcode label 307 may be a "2-D" barcode label in order to include more information on a smaller area than traditional barcode labels. In some examples, the barcode label 307 or RFID tag 308 includes the drug identifying label 309A and 309B for convenient use by the caregiver.

In some examples, the syringes 306A and 306B can be filled at the point of use and may be labeled with drug labels 309A and 309B and either barcode labels 307 or RFID tags 308 that are removably attached to the drug bottle or vial at the factory or pharmacy. The drug labels 309A and 309B and either barcode labels 307 or RFID tags 308 may be easily removed from the drug bottle or vial and adhesively attached to the syringe 306A or 306B at the time that the syringe 306A or 306B is loaded with the drug by the caregiver. Instead of, or in addition to the barcode labels 307 or RFID tags 308, any other suitable "tag/reader" system known in the arts, may be used.

Figure 4:
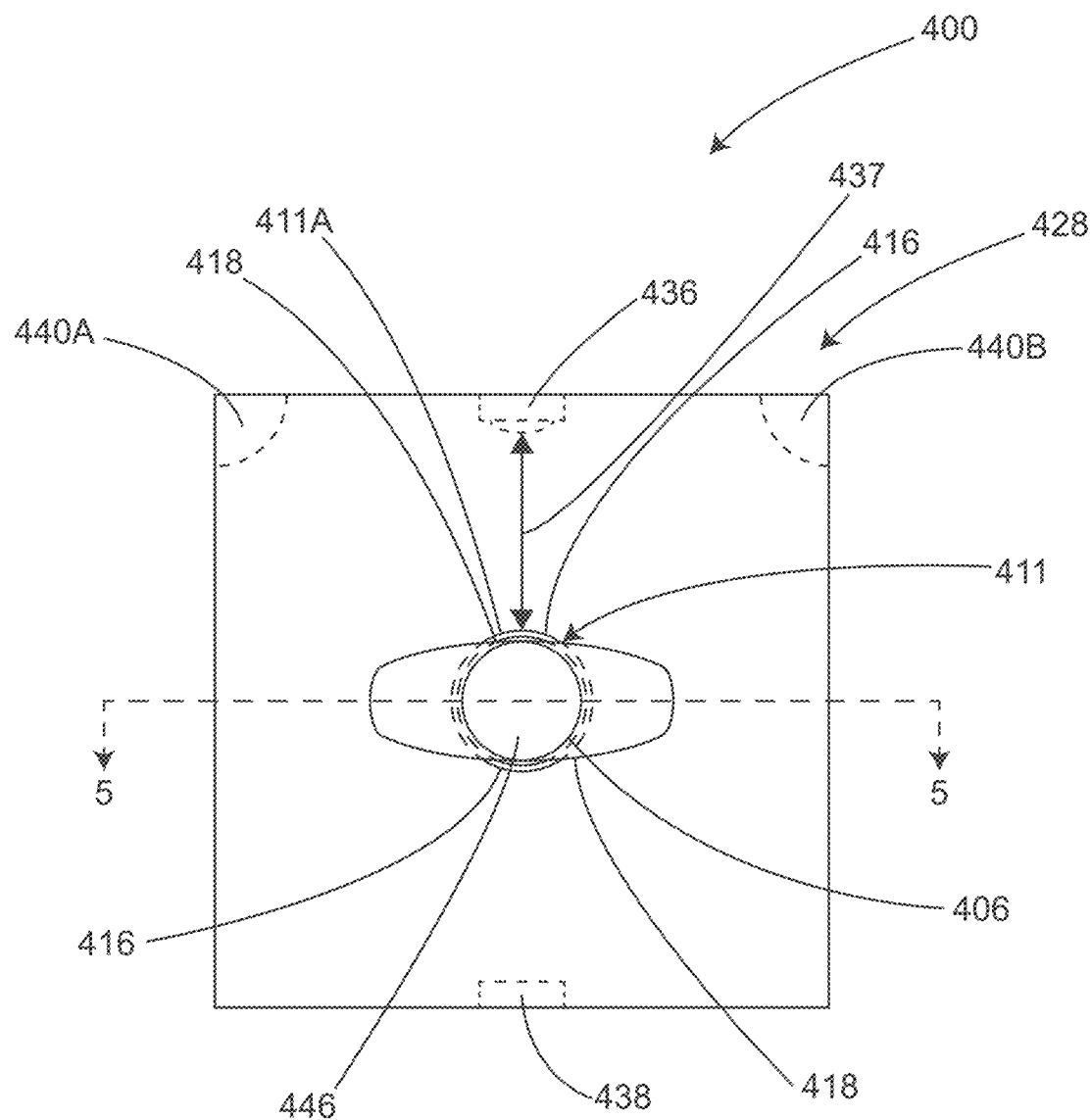
FIG. 4 illustrates a side view of an example medication identification and measurement system and a syringe that can be used with the system of FIGS. 1 and 2, to monitor drug delivery, in accordance with at least one example of this disclosure.
Figure 5:
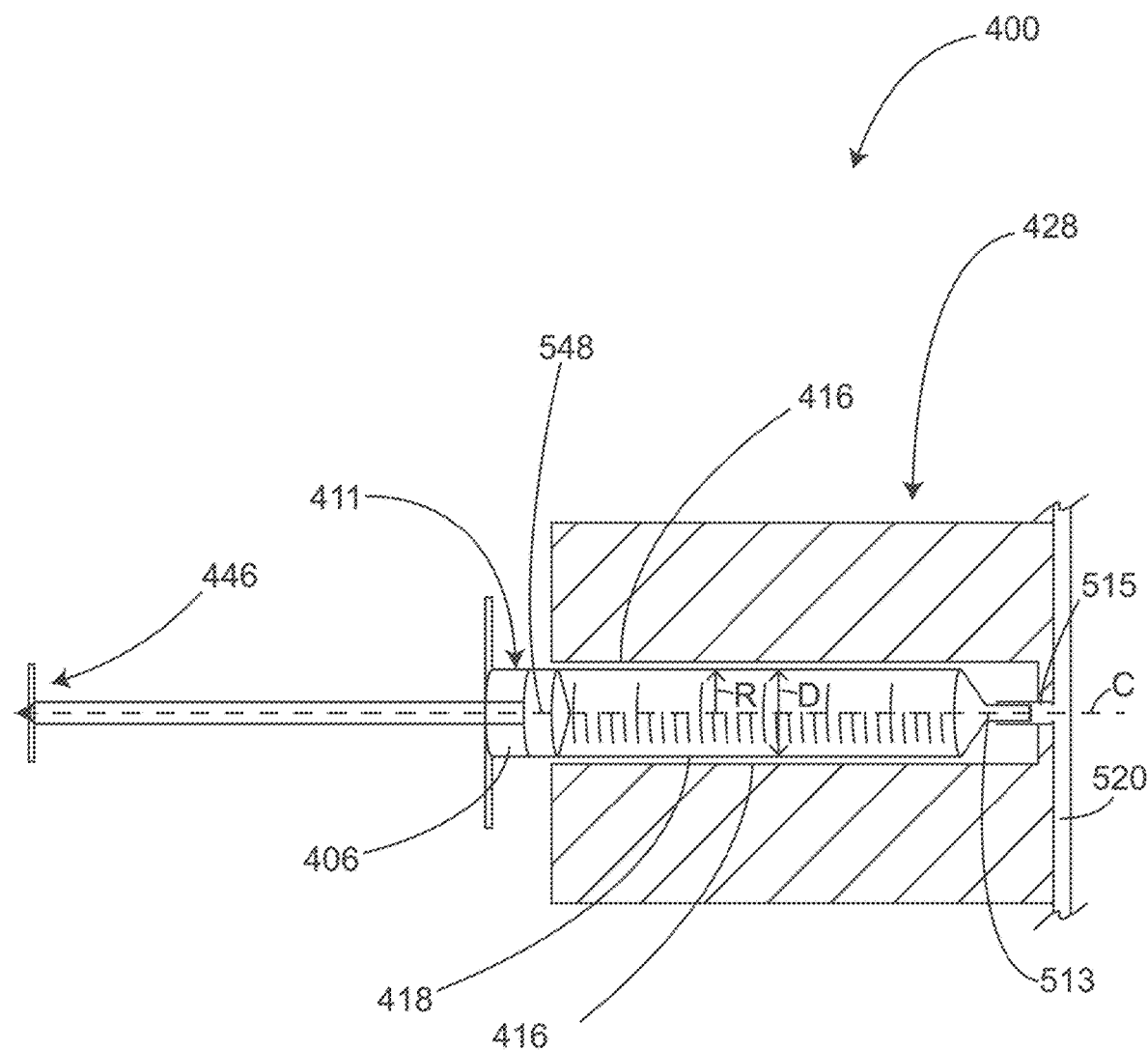
FIG. 5 illustrates a cross-sectional view of the medication identification and measurement system and a syringe (not shown in cross-section) of FIG. 4, taken along line 5-5, in accordance with at least one example of this disclosure.

FIGS. 4-10 illustrate examples of medication identification and measurement systems 428, 628, 828 that can be used with the automated data consolidation module 100, 200 of FIGS. 1 and 2. However, aspects of the medication identification and measurement systems 428, 628 and 828 may be used with other systems, and other medication identification and measurement systems may be used with the automated data consolidation module 100, 200. Furthermore, some examples of the automated data consolidation module 100, 200 can omit aspects of the medication identification and measurement systems, or can omit a medication identification and measurement system altogether. FIG. 4 illustrates a portion of an automated data consolidation module 400 including a side view of an example medication identification and measurement system 428 and a syringe 406 that can be used with the automated data consolidation module 100, 200 of FIGS. 1 and 2, to monitor drug delivery. FIG. 5 illustrates a cross-sectional view of the medication identification and measurement system 428 and the syringe 406 (not shown in cross-section) of FIG. 4, taken along line 5-5. FIGS. 4 and 5 are described together.

As shown in FIGS. 4 and 5, the medication identification and measurement system 428 may include at least one injection portal 411. The injection portal 411 may be a receptacle for accommodating a syringe 406 in a fixed and known location and can be configured to orient the Luer taper connector 513 to mate with an injection port 515. The injection port 515 can be secured within the injection portal 411 and can be in fluid communication with IV tubing 520. In some examples, the injection portal 411 may include an injection portal tube 416, such as a transparent tube that is sized to receive and accommodate a syringe barrel 418 of a syringe 406. In some examples, the injection portal can be configured to receive a specific size syringe barrel 418. In some examples, multiple injection portals 411 can be provided to accommodate syringes 406 of different sizes.

Figure 6:
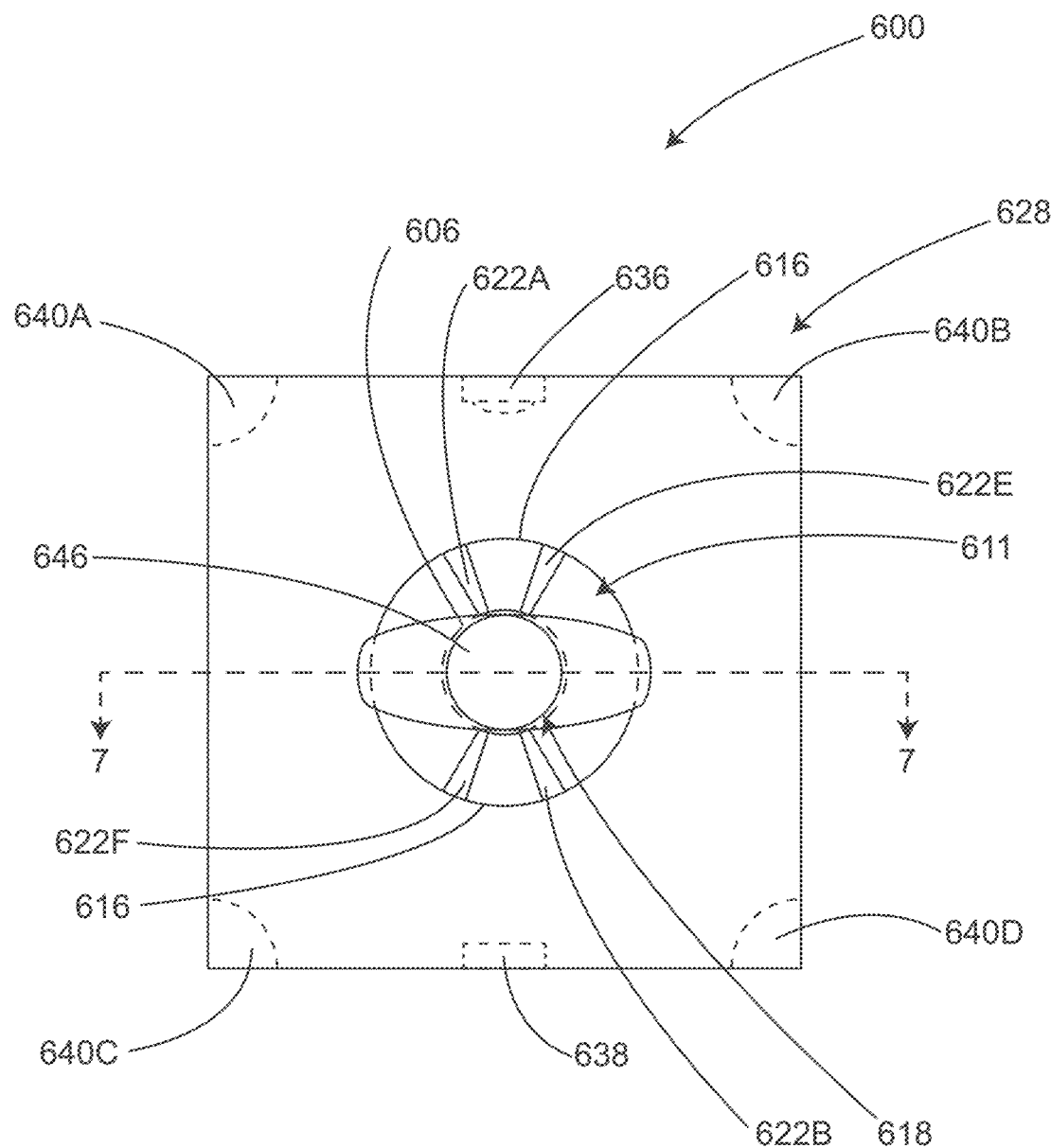
FIG. 6 illustrates a side view of a second example medication identification and measurement system and a syringe that can be used with the system of FIGS. 1 and 2, in accordance with at least one example of this disclosure.
Figure 7:
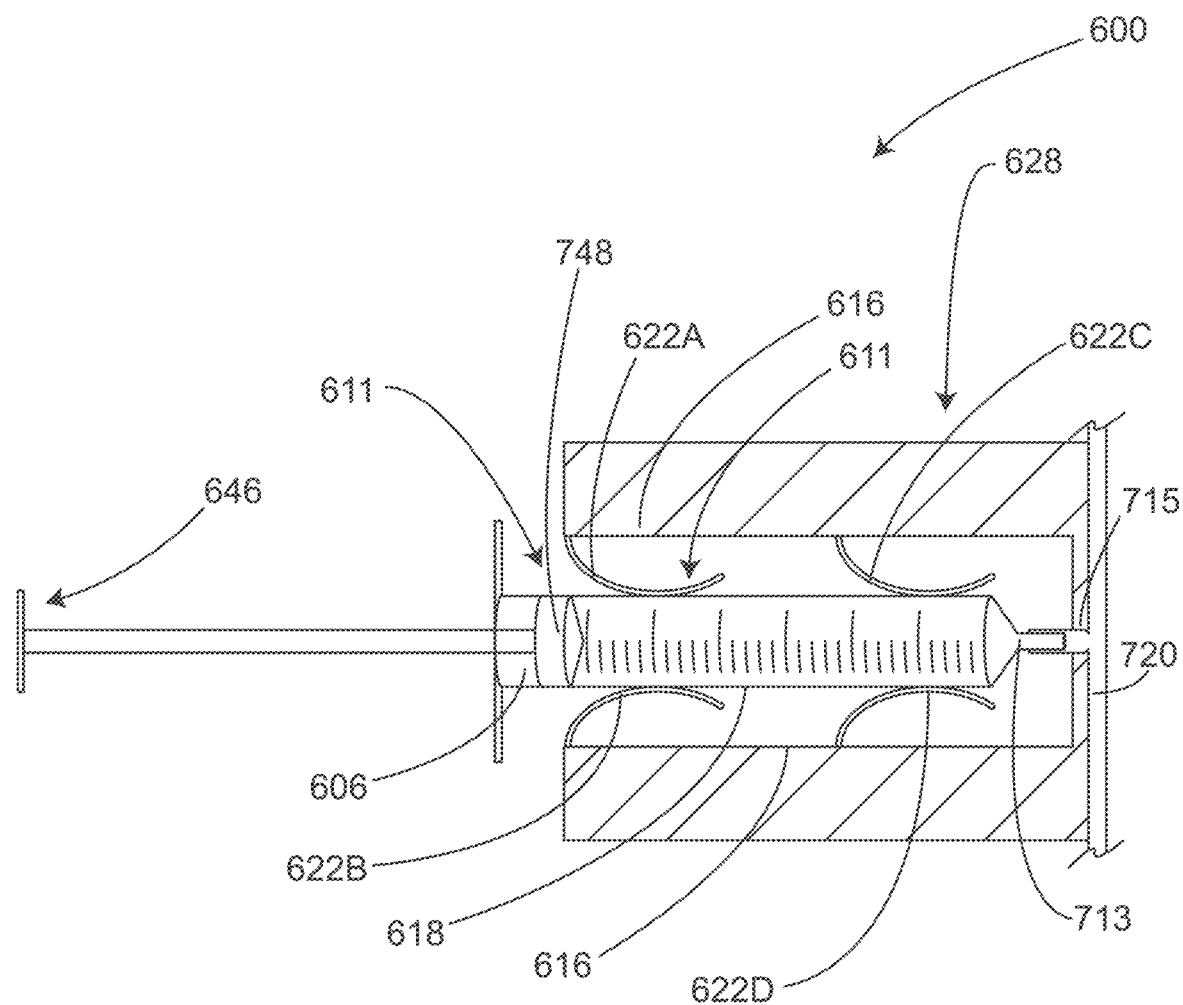
FIG. 7 illustrates a cross-sectional view of the second example of a medication identification and measurement system and the syringe (not shown in cross-section) of FIG. 6, taken along line 7-7, in accordance with at least one example of this disclosure.

FIG. 6 illustrates a portion of an automated data consolidation module 600 including a side view of a second example of a medication identification and measurement system 628 and a syringe 606 that can be used with the automated data consolidation module 100, 200 of FIGS. 1 and 2, to monitor drug delivery. FIG. 7 illustrates a cross-sectional view of the second example of a medication identification and measurement system 628 and the syringe 606 (not shown in cross-section) of FIG. 6, taken along line 7-7. FIGS. 6 and 7 are described together.

As shown in FIGS. 6 and 7, the injection portal 611 of the medication identification and measurement system 628 may be large enough to accommodate syringes 606 of multiple sizes within the space defined by a real or imaginary injection portal tube 616. In this example, accurately orienting the Luer taper connector 713 to mate with an injection port 715 may be accomplished by one or more orienting members such as one or more spring positioning members 622A-F that engage with the syringe barrel 618 to center it in the injection portal 611. In some examples, there may be two or more rows of spring positioning members 622A-F. For example, spring positioning members 622A, B, E, F may be located near the entrance to the injection portal 611 and spring positioning members 622C, D may be located near the injection port 715 to assure accurate positioning for mating with the Luer taper connector 713. Spring positioning members 622A-F may include not only spring wires or metal or polymer or plastic spring pieces but any flexible material or combination of materials or shapes that can be deformed by the syringe barrel 618 entering the injection portal 611 and retain a memory (e.g., elastically deformable, substantially elastically deformable, resiliently deformable, resilient member) so as to urge the syringe barrel 618 into a centered position within the space defined by a real or imaginary injection portal tube 616.

One objective of the spring positioning members 622A-F can be to "automatically" center and align the Luer taper connector 713 of the syringe 606 with the injection port 715, so that the operator can simply and conveniently push the syringe 606 into the injection portal 611 and no further manual alignment may be needed. The spring positioning members 622A-F can also obviate the need for the operator to touch either the Luer taper connector 713 of the syringe 606 or the injection port 715, thus beneficially preventing accidental infectious contamination by the operators' fingers and gloves.

Figure 8:
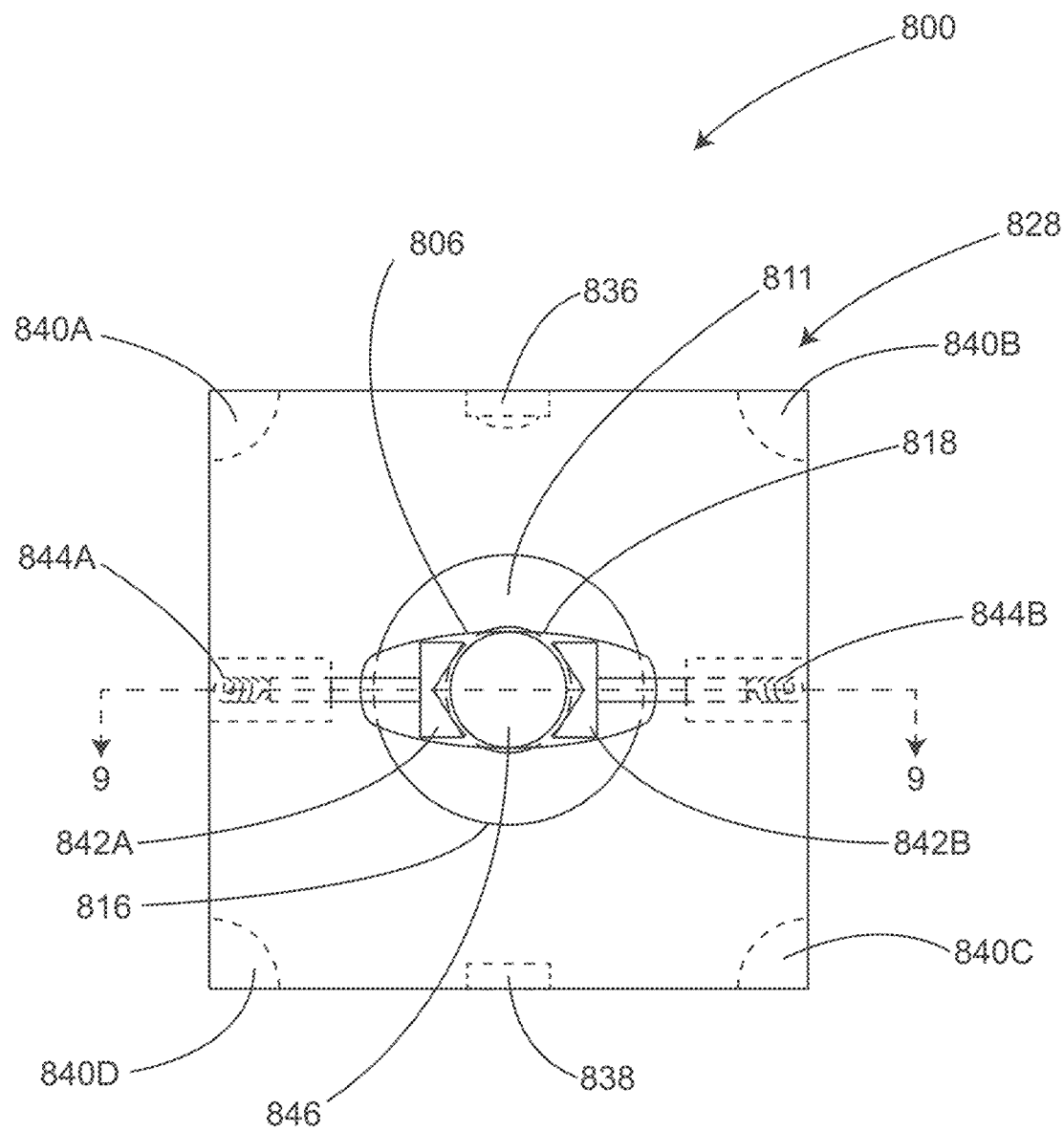
FIG. 8 illustrates a side view of a third example of a medication identification and measurement system and a syringe that can be used with the system of FIGS. 1 and 2, in accordance with at least one example of this disclosure.
Figure 9:
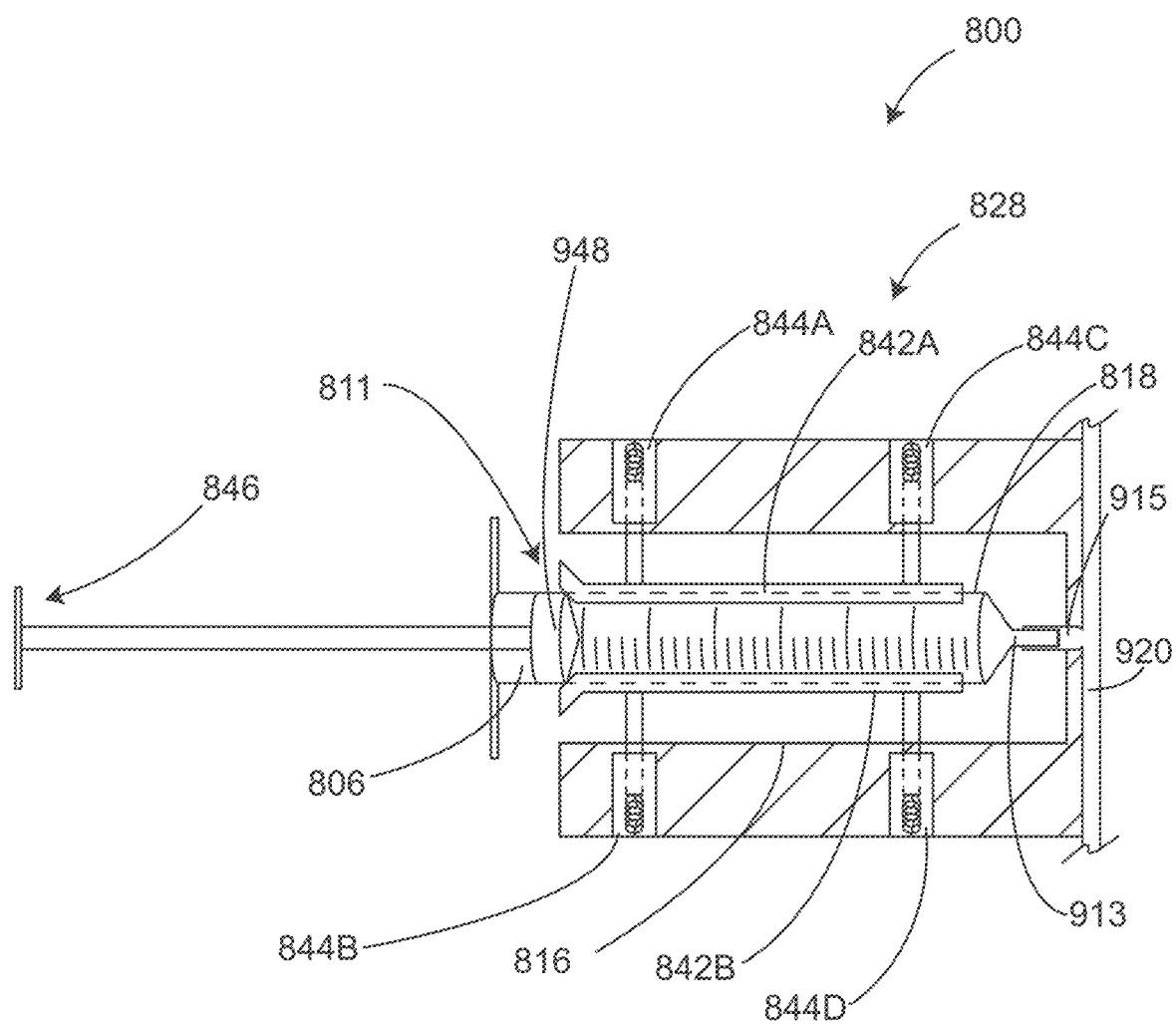
FIG. 9 illustrates a cross-sectional view of the third example of a medication identification and measurement system and the syringe (not shown in cross-section) of FIG. 8, taken along line 9-9, in accordance with at least one example of this disclosure.

FIG. 8 illustrates a portion of an automated data consolidation module 800 including a side view of a third example of a medication identification and measurement system 828 and a syringe 806 that can be used with the automated data consolidation module 100, 200 of FIGS. 1 and 2. FIG. 9 illustrates a cross-sectional view of the third example of a medication identification and measurement system 828 and the syringe 806 (not shown in cross-section) of FIG. 8, taken along line 9-9. FIGS. 8 and 9 are described together.

As shown in FIGS. 8 and 9, a syringe barrel 818 may be centered and held in place by one or more orienting members, such as compression positioning members 842A,B. The compression positioning members 842A, B may be urged apart by inserting the syringe barrel 818 there between. Springs 844A-D can compress and create a pressure pushing the compression positioning members 842A,B against syringe barrel 818. The compression positioning members 842A,B shown in FIGS. 8 and 9 are merely illustrative, and many other sizes, shapes, numbers and locations of compression positioning members 842 are anticipated.

Compression positioning members 842A,B may be simple spring 844A-D activated devices (e.g., resilient members) as shown in FIGS. 8 and 9 or may be any mechanism that can expand (e.g., resiliently expand) to accommodate syringe barrels of various sizes and urge the syringe barrel 818 into a centered position within the space defined by a real or imaginary injection portal tube 816. This example shows spring 844A-D activated compression positioning members 842A,B but many other mechanical activation mechanisms are anticipated. The compression positioning members 842A,B can be elastically deformable, substantially elastically deformable, resiliently deformable, include one or more resilient members.

Other examples of positioning members designed to hold an inserted syringe 806 in the center of the injection portal 811 and thus orienting the Luer taper 913 for mating with the injection port 915 are anticipated. Positioning the inserted syringe 806 in the center of the injection portal 811 allows the machine vision to work from a known distance and thus calculations of syringe plunger 948 movement can be very accurate.

In some examples, instead of the positioning members shown in the examples of FIGS. 6-9 holding a syringe centrally, the positioning members 622A-F or 842A,B can be designed to hold an inserted syringe 606, 806 at a known, but off center position in the injection portal 611, 811, such as when the injection port 715, 915 (FIGS. 7 and 9) is positioned off center in the injection portal 611, 811. Any arrangement of at least one positioning member that aligns an inserted syringe at a known position may be provided.

In some examples, and as shown in FIGS. 4, 6 and 8 the medication identification and measurement system 428, 628, 828 of this disclosure may include one or more "machine vision" cameras 436, 636, 836 that input digital images into one or more processors having processing circuitry 157, 257 as shown and described in FIGS. 1,2, that is programed to analyze machine vision images. In some examples, one of the images that the machine vision cameras 436, 636, 836 may "see" is a barcode label 307 on the syringe 406, 606, 806, that has been inserted into the injection portal 411, 611, 811, for identifying the medication in the syringe 406, 606, 806. As previously noted, the barcode label 307 can identify the brand name and/or generic name of the medication in the syringe. In some examples, the barcode label 307 also may identify one or more of the concentration of the medication, the lot number, the expiration date and other information that may be useful for inventory management.

As shown in FIGS. 4, 6 and 8, the automated data consolidation module 400, 600, 800 of this disclosure can include one or more radio frequency identification (RFID) interrogation antennas 438, 638, 838 that input RFID information into a processor, such as processing circuitry 157, 257 as shown and described in FIGS. 1 and 2, that is programed to analyze RFID data. In some examples, the RFID interrogation antennas 438, 638, 838 can interrogate a RFID tag 308 (FIG. 3) attached to the syringe 406, 606, 806, that has been inserted into the injection portal 411, 611, 811, for identifying the medication in the syringe 406, 606, 806. In some examples, short range RFID such as near field (NF) or high frequency (HF) may be advantageous because they may only detect the syringe 406, 606, 806 that is adjacent to or inside the security system for IV medications 400, 600, 800, and not detect the various other medication syringes that may be sitting on the worktable such as 206A-206C in FIG. 2.

As shown in FIGS. 4, 6 and 8 the medication identification and measurement system 428, 628, 828 of this disclosure may include a RFID interrogator 438, 638, 838. In some examples, the RFID interrogator 438, 638, 838 that can include antennas that may be located inside the medication identification and measurement system 428, 628, 828. In some examples, the RFID interrogator antennas 438, 638, 838 may be located external to but proximate the medication identification and measurement system 428, 628, 828. As the syringe 406, 606, 806 is brought into proximity of the medication identification and measurement system, the RFID interrogator 438, 638, 838 can interrogate the RFID tag 308 on the syringe 406, 606, 806, thereby accurately and reliably identifying a medication for IV administration. In some examples, the RFID tag 308 or other marker may include one or more of: the generic and brand name of the drug, the concentration, the lot number, the expiration date, the manufacturer and other important information that may be recorded. In some examples, the generic and brand name of the drug and the concentration of the drug can be displayed in the injection section of a display such as the display 126, 226 (FIGS. 1, 2).

Machine vision is very accurate for measuring the size of an object at a known distance or the distance of an object of known size. However, it cannot do both. Therefore, in some examples it is important to know the exact location of a syringe and thus know the distance from the camera to the syringe in order to accurately calculate the distance of the movement of the plunger within the syringe.

Syringes are available in multiple sizes such as 3 cc, 6 cc and 12 cc, each of which is a different diameter. The machine vision processor must know both the internal diameter of the barrel of the syringe and the distance that the syringe plunger moves down the barrel, in order to calculate the volume of medication injected, unless it has another source of information. The machine vision of this disclosure can measure the diameter of the syringe because in the examples the syringe 406, 606, 806 is held at known distance and in a centered location relative to the machine vision cameras 436, 636, 836. Alternately, the automated data consolidation module 400, 600, 800 of this disclosure may be programed to know that the particular hospital uses only Monoject® syringes for example and the internal diameter of each Monoject® syringe size may be pre-programed into the computer. In this case, the machine vision only needs to differentiate 3 cc, 6 cc and 12 cc syringe sizes from each other. The machine vision processor can determine the internal diameter of the barrel of the syringe. In some examples, the syringe size may be included in the information provided by the barcode 307 or RFID 308 (FIG. 3).

In some examples, such as the examples of FIGS. 4-9, the machine vision system, including the machine vision camera 436, 636, 836 and the processor 157, 257 of FIGS. 1 and 2 (e.g., processing circuitry) in electrical communication with the machine vision camera 436, 636, 836, can visually detect and determine other geometry information about the syringe 406, 606, 806 besides the outside diameter, such as determining the inside diameter, or the inner or outer length of the syringe. The medication identification and measurement systems 428, 628, 828 can use the geometry information to determine the size or type of the syringe 406, 606, 806, or can use the geometry information to calculate a volume of the syringe 406, 606, 806.

In some examples, as the syringe 406, 606, 806 is advanced into the injection portal 411, 611, 811, the image of the syringe 406, 606, 806 entering the injection portal 411, 611, 811 is displayed in real time in an injection section 126a, 226a of the display 126, 226 (FIGS. 1 and 2). Therefore, the caregiver can watch the syringe 406, 606, 806 advance and engage with the injection port 515, 715, 915. In some examples, the injection portal tube 416, 616, 816 or the spring positioning members 622A-E or the compression positioning members 842A,B, urge the syringe 606, 806 into position to mate with the injection port 715, 915 but the actual connection can also be observed as it is happening by the caregiver on the display 126, 226. Even though the caregiver is not physically holding the injection port 515, 715, 915 as they typically would, they can watch the engagement of the Luer connector 513, 713, 913 with the injection port 515, 715, 915 on a display 126, 226, the view is essentially identical to the thousands of injections that they have made during their career. In some examples, the actual image of the syringe 406, 606, 806 can be displayed on the display 126, 226, while in other examples the data obtained by the camera 436, 636, 836 can be converted to a representation of the syringe displayed on the display 126, 226.

In some examples, once the syringe 406, 606, 806 is securely connected to the injection port 515, 715, 915, the caregiver pushes on the plunger 446, 646, 846 of the syringe 406, 606, 806, injecting the medication into the injection port 515, 715, 915 and IV tubing 520, 720, 920. The caregiver can visualize the plunger seal 548, 748, 948 move down the syringe barrel 418, 618, 818 and can determine the volume of medication injected by the graduated markings on the syringe 406, 606, 806. Thus, the engagement of the Luer connector 513, 713, 913 with the injection port 515, 715, 915 and the injected volume are observed by the caregiver on the display 126, 226 and the traditional method and routine of injection is minimally altered by implementing the automated data consolidation module 100, 200 including the example medication identification and measurement systems 428, 628, 828.

In some examples, the processing circuitry 157, 257 (FIGS. 1 and 2) or a computer may also simultaneously generate data representing a running total of the volume and dosage of the injected medication and can transmit the generated data to the display 126, 226 to display volume and dosage information on the display 126, 226. In some examples, the processing circuitry 157, 257 or a computer may also generate its own graduated scale and transmit the generated graduated scale information to the display 126, 226 to superimpose the scale on the image of the syringe 406, 606, 806 or next to the image of the syringe 406, 606, 806, for added visual clarity of the injected volume and dose.

In some examples, the machine vision determination of the injected volume may be calculated by multiplying the internal cross-sectional area of the syringe ($\pi r^2$) by the distance that the syringe plunger moves. The radius of the syringe may be determined in one or more ways. For example, the machine vision function may determine that the syringe approximates a 3 cc or 12 cc syringe and the computer is programmed to know that the hospital uses a specific brand of syringes and the internal diameter (radius) of each of these syringe sizes is precisely known. (An example of diameter d, radius r is shown in FIG. 5) Another example may require the machine vision camera to measure the outer diameter of the syringe and then subtract an approximated wall thickness (either measured or known value stored in a memory) from the measured diameter to determine the internal diameter. In another example, the internal diameter of the syringe may be supplied to the processing circuitry 157, 257 or a computer as part of the RFID 308 or barcode 307 information. In another example, the machine vision may determine the inner diameter of the syringe by determining an outer diameter of the plunger as viewed through the transparent or semi-transparent syringe and determine the wall thickness, In yet another example, the machine vision may be able to visibly determine the inner diameter or radius directly through the transparent or semi-transparent syringe. Any other suitable determination, calculation or algorithm may be used to determine the radius, diameter and injected volume.

In some examples, the machine vision determination of the distance that the syringe plunger 446, 646, 846 moves may be by "observing" the movement of the black rubber plunger seal 548, 748, 948 against the visible scale printed on the syringe 406, 606, 806. In this example, the machine vision can be programmed to recognize the markings on the syringe 406, 606, 806.

In some examples, the machine vision determination of the distance that the syringe plunger 446, 646, 846 moves may be by observing the movement of the black rubber plunger seal 548, 748, 948 relative to a scale calculated by the processing circuitry 157, 257 (FIGS. 1 and 2). The geometrical calculation of the scale that determines the distance that the syringe plunger 446, 646, 846 moves may be easiest to determine along the widest part of the syringe that corresponds with the center C (FIG. 5) of the syringe 406, 606, 806, which is a known distance from the machine vision camera 436, 636, 836. Alternatively, the computer-constructed scale may be applied to the side of the syringe 406, 606, 806 facing the camera 436, 636, 836, if the radius of the syringe 406, 606, 806 is subtracted from the known distance to the center C (FIG. 5) of the syringe 406, 606, 806 in order to calculate the distance 437 from the machine vision camera 436, 636, 836 to the near side (e.g., 411A) of the syringe 406, 606, 806.

In some examples, the movement of the black rubber plunger seal 548, 748, 948 of the syringe 406, 606, 806 can be clearly identifiable by the machine vision camera 436, 636, 836 and a scale to determine the distance moved by the plunger 446, 646, 846 can either be "visualized" or constructed by the machine vision computer (e.g., processing circuitry). Multiplying the distance that the plunger seal 548, 748, 948 moves by the known or measured internal diameter d (FIG. 5) of the syringe 406, 606, 806 and thus cross-sectional area of the plunger seal 548, 748, 948, allows the processing circuitry 157, 257 or a computer in electrical communication with the processing circuitry 157, 257 to calculate an accurate injected volume. The measured injection volume and dosage may be displayed on the display 126, 226 of the module 101, 201 (FIGS. 1 and 2). Without interfering with or changing the anesthesiologists' normal or traditional medication injection routines, an unobtrusive machine vision camera 436, 636, 836 and computer (e.g., processing circuitry) can "observe" the medication injections and automatically record them in the EMR.

In some examples, the injected volume of medication may be determined by other sensors or methods. For example, the systems described herein can employ (e.g., substitute) other sensors such as a non-visual optical sensor 436A in place of or in addition to the machine vision camera 436, 636, 638 described in FIGS. 4-9. For example, a light source can shine on one or more light sensitive elements such as photodiodes, and the position of the plunger of the syringe can be roughly determined by the obstruction of the light beam by the plunger. Other fluid measurement methods can have a sensor including adding magnetic material to the syringe plunger and detecting movement of the plunger with a magnetic proximity sensor. Alternatively, fluid flow may be measured with fluid flow meters in the IV fluid stream. These examples are not meant to be an exhaustive list but rather to illustrate that there are alternative technologies to machine vision (e.g., sensors), for noncontact measurement (e.g., sensing) of fluid flow from a syringe that are anticipated in this disclosure.

In some examples, the injected volume of medication may be determined by other sensors or methods. For example, the systems described herein can employ (e.g., substitute) other sensors in place of or in addition to the machine vision cameras for either or both the medication and fluid flows. Other fluid flow sensors anticipated by this disclosure include but are not limited to: ultrasonic flow meters, propeller flow meters, magnetic flow meters, turbine flow meters, differential pressure flow meters, piston flow meters, helical flow meters, vortex flow meters, vane flow meters, paddle wheel flow meters, thermal flow meters, semicylindrical capacitive sensor flow meters and Coriolis flow meters.

Securing the injection port 515, 715, 915 within the injection portal 411, 611, 811 prevents the caregiver from touching the injection port 515, 715, 915. Normally caregivers wear gloves to protect themselves from infectious contaminates from the patient and operating room and their gloves are nearly always contaminated. Anything they touch will be contaminated. They typically pick up and hold the IV injection port 515, 715, 915 with one hand while inserting the Luer taper connector 513, 713, 913 of the syringe 406, 606, 806 into the injection port 515, 715, 915. In the process, the injection port 515, 715, 915 is frequently contaminated with pathogenic organisms from their gloves that can enter the patient's blood stream with the next injection, causing serious infections. It is therefore advantageous from the infection prevention point of view, if the Luer connection and injection can be accomplished while never touching the injection port 515, 715, 915.

Figure 11:
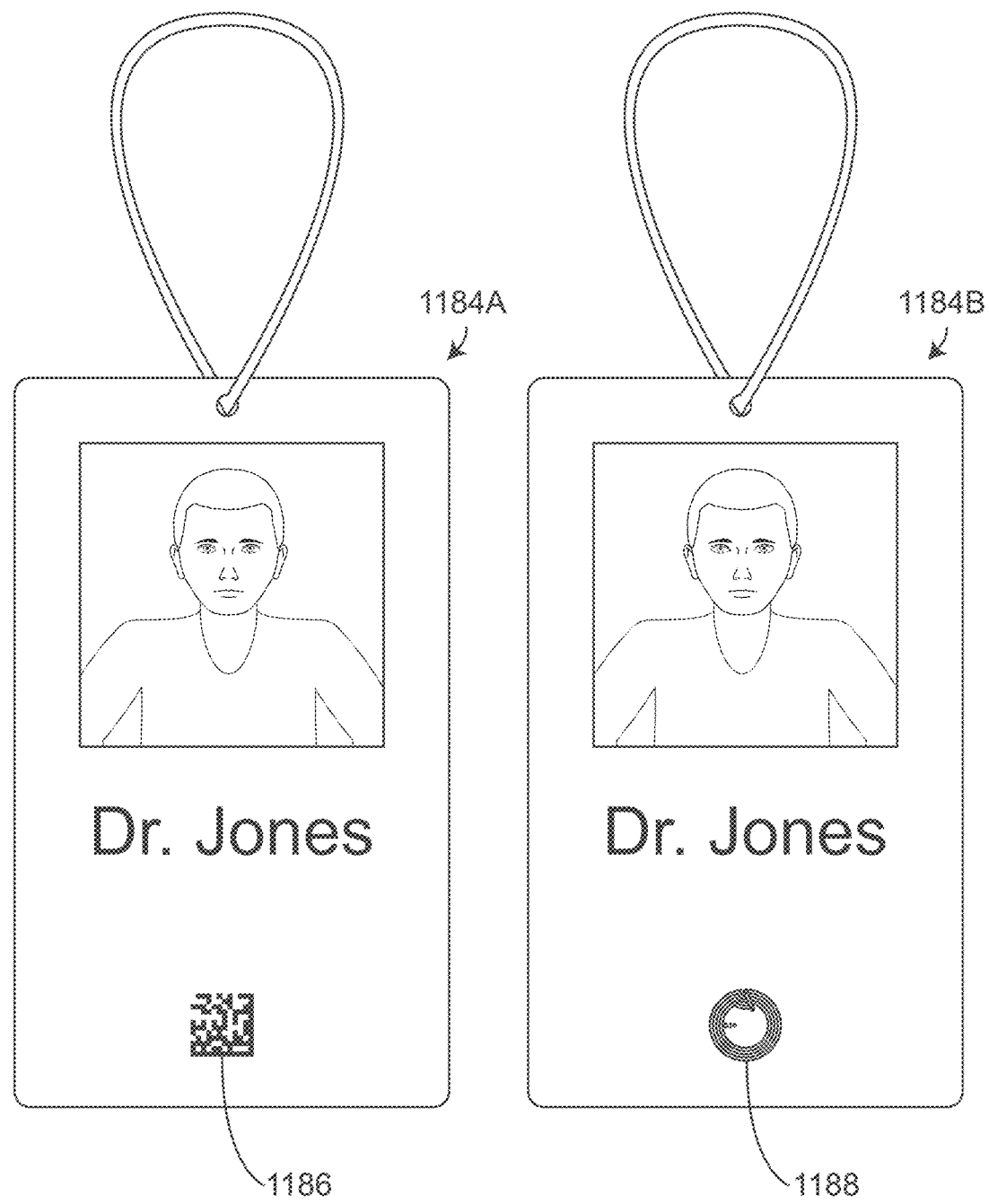
FIG. 11 illustrates a plan view of an example of healthcare provider ID badges that can be used with the system of FIGS. 1 and 2, in accordance with at least one example of this disclosure.

In some examples as shown in FIGS. 1 and 2, the automated data consolidation module 100, 200 may include an external reader, such as barcode reader 180, 280 on the module 101, 201 to read a barcode, QR code or the like for identification. This barcode reader 180, 280 may be used to identify the healthcare provider injecting a medication by reading a barcode or QR code 1186 on the user's ID badge for example (FIG. 11). In some examples as shown in FIGS. 1 and 2, the automated data consolidation module 100, 200 may include an external RFID reader 182, 282 on the module 101, 201. This RFID reader 182, 282 may be used to identify the healthcare provider injecting a medication by reading an RFID tag 1188 on the user's ID badge 1184B for example (FIG. 11). In some examples as shown in FIGS. 4, 6 and 8, the automated data consolidation module 400, 600, 800 may include an internal RFID reader 438, 638, 838 in the module 101, 201. This RFID reader 438, 638, 838 may also be used to identify the healthcare provider injecting a medication by reading an RFID tag on the user's ID badge for example.

It is an important part of the record to know who injected the medication and their identity can be easily verified and documented by the automated data consolidation module 400, 600, 800 using either barcode, QR code or RFID. Other identification technologies are also anticipated.

Figure 10:
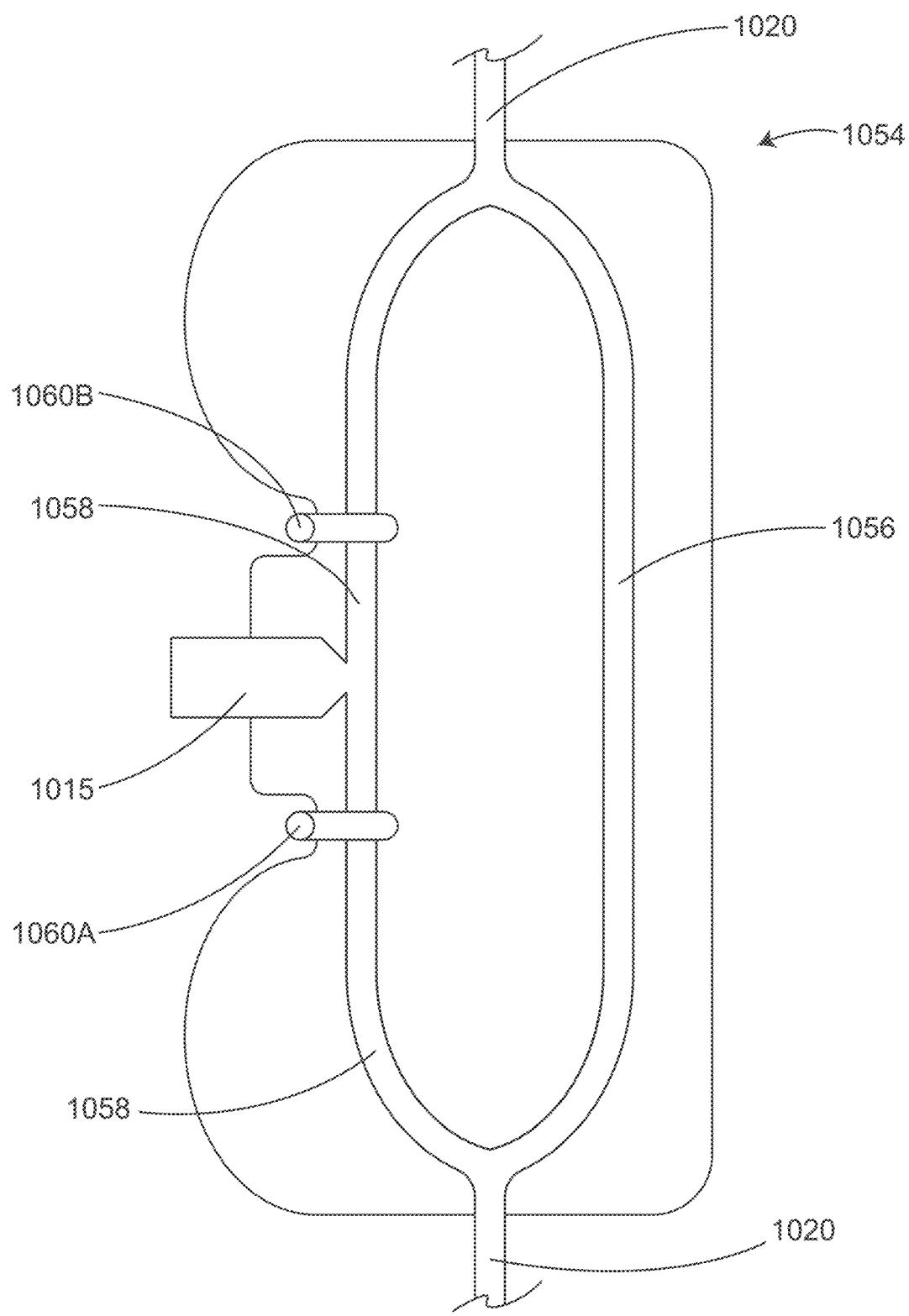
FIG. 10 illustrates an example injection port cassette that can be used with the system of FIGS. 1 and 2, as detailed in FIGS. 5, 7 and 9, in accordance with at least one example of this disclosure.

FIG. 10 illustrates an example injection port cassette 1054 that can be used with the automated data consolidation module 100, 200 of FIGS. 1 and 2, as detailed in FIGS. 5, 7 and 9. As shown in FIG. 10, the injection port 1015 may be mounted on an injection port cassette 1054 in order to make the attachment to the automated data consolidation module 100, 200, 400, 600, 800 easier and more secure. The injection port cassette 1054 may be a piece of molded polymer or plastic onto which the injection port 1015 and IV tubing 1020 may be attached. The injection port cassette 1054 may be shaped and sized to fit into a slot in the automated data consolidation module 100, 200, 400, 600, 800. When the injection port cassette 1054 is fit into a slot in the automated data consolidation module 100, 200, 400, 600, 800, the injection port 1015 can be positioned substantially in the center of the injection portal 411, 611, 811 for mating with the Luer tapers 513, 713, 913. The injection port cassette 1054 can also be configured to be removed intact from the automated data consolidation module 400, 600, 800 so that the patient can be transferred and the IV tubing 1020 can be moved with the patient and continue to operate normally.

In some examples, and as shown in FIG. 10, the injection port cassette 1054 can include an IV bypass channel 1056 in the IV tubing 1020. The IV bypass channel 1056 can allow the IV fluids to flow unencumbered by the medication injection apparatus. The injection port cassette 1054 can include a medication channel 1058 in the IV tubing 1020 and, the medication channel 1058 may include one or more stop-flow clamps 1060A,B. The one or more stop-flow clamps 1060A,B may be activated by the automated data consolidation module 100, 200, 400, 600, 800 if a medication error is identified. The one or more stop-flow clamps 1060A,B may be powered by one or more electromechanical solenoids that squeeze the IV tubing in the medication channel 1058 flat, obstructing the flow. Other electromechanical flow obstructers are anticipated.

In some situations, such as when administering a drug to a patient allergic to that drug, or administering potent cardiovascular drugs to a patient with normal vital signs, or administering a drug with a likely mistaken identity, the computer, such as processing circuitry 157, 257 (FIGS. 1 and 2) for the automated data consolidation module 100, 200, 400, 600, 800 of this disclosure can automatically activate the stop-flow clamps 1060A,B to compress the medication channel 1058 tubing upstream and/or downstream from the injection port 1015. Compressing the IV tubing both upstream and downstream from the injection port 1015 prevents the injection of any medication into the IV tubing 1020. An alert to the adverse condition of the injection may be displayed on display 126, 226 where the stop-flow condition can be over-ridden by the operator touching a manual override switch on the display 126, 226 or the module 101, 201, if the injection was not erroneous. While the stop-flow can occur in the medication channel 1058, the IV fluid flow can continue normally in the parallel bypass channel 1056.

The stop-flow clamps 1060A,B can allow the processing circuitry 157, 257 (e.g., processor, hardware processing circuitry) of the automated data consolidation module 100, 200, 400, 600, 800 to not only warn the operator of a pending medication error, but physically prevent the injection. Perhaps equally as important is that the stop-flow clamps 1060A,B can be quickly released by the operator touching a manual override switch in the event that the apparent error was in fact a planned event or otherwise desired by the operator.

In some examples, a part of the automated data consolidation module 100, 200, 400, 600, 800 can include the ability for the computer (e.g., machine) to know the patient's medical history, medication orders, vital signs, current medications, medication orders and other important information about that patient. In some examples, the medication in syringe 306 can be identified by RFID tag 308 (FIG. 3) and is detected by RFID interrogator 438, 638, 838 as the syringe 306 enters injection portal 411, 611, 811. The processing circuitry (e.g., 157, 257) of the automated data consolidation module 100, 200, 400, 600, 800 can cross-reference the proposed injection to the patient's medical history, medication orders, vital signs, current medications and other important information about that patient, providing a safety "overwatch" guarding against medication errors. In some examples, the processing circuitry (e.g., 157, 257) of the automated data consolidation module 100, 200, 400, 600, 800 may include algorithms and/or "artificial intelligence" that can provide alternative medication suggestions based on patient's medical history, medication orders, vital signs, current medications and other important information about that patient.

In some examples, the EMRs that were created by the automated data consolidation module 100, 200, 400, 600, 800 of this disclosure can provide accurate and temporally correlated information about the relationship between any injected medication and the resulting physiologic response. This is uniquely accurate dose-response data. In some examples, the EMRs that were created by the automated data consolidation module 100, 200, 400, 600, 800 for hundreds of thousands or even millions of patients, may be aggregated and analyzed as "big data." The "big data" from these EMRs may be used for a variety of purposes including but not limited to medical research, patient and hospital management and the development of "artificial intelligence" algorithms that can provide alternative medication suggestions. Ongoing "big data" from more and more EMRs can be used to continually improve and refine the "artificial intelligence" algorithms, much like the "artificial intelligence" algorithm development process being used to develop self-driving vehicles. These "artificial intelligence" algorithms can be used to provide automated ("self-driving" or "partially self-driving") anesthesia during surgery or automated medication delivery.

FIG. 11 illustrates a plan view of an example of healthcare provider ID badges 1184A and 1184B that can be used with the system of FIGS. 1 and 2, in accordance with at least one example. In some examples, the "chain of custody" may begin by electronically identifying the healthcare provider as the drugs are checked out from the pharmacy or Pixis medication dispenser. In some examples and as shown in FIG. 11, each provider can have a personalized RFID tag 1186, attached to their hospital ID badge 1184A. In some examples each provider can have a personalized barcode 1188, attached to their hospital ID badge 1184B for example. When the drugs are checked out, the personalized RFID tag 1186 may be read by an RFID interrogator or the personalized barcode 1188 read by a barcode reader in the pharmacy and the ID of the provider checking the drugs out may be noted in the hospital's computer and/or the processing circuitry 157, 257 (FIGS. 1 and 2) for the automated data consolidation module 100, 200, 400, 600, 800 (FIGS. 1, 2, 4, 6 and 8). The specific RFID 308 or barcode 307 (FIG. 3) identification of the injectable drug may also be recorded before the drug leaves the pharmacy and that information may be transmitted to the processing circuitry 157, 257 of the automated data consolidation module 100, 200, 400, 600, 800 of this disclosure. In some examples, instead of an RFID tag 1186 and RFID reader, other provider identification information and sensors for identifying the provider can be used, such provider identification information may include: a barcode, a QR code with the sensor being able to read such codes. In other examples, the sensor can include a retinal scanner, fingerprint reader or a facial recognition scanner that identifies the provider by personably identifiable information (e.g., provider identification information) may be used.

In some examples, when the provider arrives at the patient's bedside, the provider may be identified by their ID badge 1184 A,B. In some examples, an ID badge 1184A that has an RFID tag 1186 may be read by RFID reader 182, 282 (FIGS. 1 and 2) that can be located on the automated data consolidation module 100, 200, 400, 600, 800 or by RFID reader 438, 638, 838 (FIGS. 4, 6 and 8) located inside the automated data consolidation module 100, 200, 400, 600, 800 (FIGS. 1, 2, 4, 6 and 8). In some examples, an ID badge 1184B that has a barcode 1188 may be read by barcode reader 180, 280 that can be located on the automated data consolidation module 100, 200, 400, 600, 800. In some examples, a retinal scanner may be located on or near module 101, 201 in order to positively identify the provider by their retinal vasculature. Other scanners including but not limited to facial recognition scanning are also anticipated in order to positively identify the provider doing the injection in order to automatically document this information to an EMR or other record.

In some examples, the provider's photograph may be taken by camera 190, 290 (FIGS. 1 and 2) for further identification before allowing the injection of scheduled drugs. In some examples, the camera 190, 290 may be triggered, such as by processor 157, 257 (FIGS. 1 and 2), when a syringe e.g., 306B filled with a scheduled drug such as a narcotic is identified as it enters the injection portal 411, 611, 811 and the RFID interrogator 438, 638, 838 interrogates the RFID tag 308 (FIG. 3) or the machine vision camera 436, 636, 836 reads the barcode 307 (FIG. 3) on the syringe 306A. Non-scheduled medications may not need the added security of a photograph.

In some examples as shown in FIGS. 1 and 2, the automated data consolidation module 100, 200 of this disclosure may include a remote monitor with display 187, 287. The remote monitor may include a wired or wireless connection to the automated data consolidation module 100, 200 and may display some or all of the information shown on the electronic record display 126, 226, or other information generated by the automated data consolidation module 100. For example, the processing circuitry 157, 257 can be in electrical communication with the remote display 187, 287 and the processing circuitry 157, 257 can send instructions to the remote display 187, 287 to display the generated information.

The remote monitor may be in the next room or miles away. The remote monitor may allow remote supervision of healthcare delivery. For example, anesthesiologists frequently supervise up to four surgical anesthetics at once, each being delivered by a nurse anesthetist. In this case, the anesthesiologist carrying a wireless remote monitor 187, 287 can have real-time data on each case under their supervision. Similarly, a nurse anesthetist working in a rural hospital may be supervised by an anesthesiologist who is 50 miles away.

In some examples, the remote monitor with display 187, 287 can create a record for billing. For example, when an anesthesiologist is supervising multiple anesthetics at once, the payers may dispute the involvement in each case and refuse to pay. The remote monitor with display 187, 287 may include an RFID reader that documents the close proximity of an RFID tag on the anesthesiologist's ID badge. Any other type of proximity sensor may be used in place of the RFID tag, including but not limited to GPS location sensing. Documenting that the anesthesiologist was carrying the remote monitor with display 187, 287 throughout the time of the surgery is very good evidence that the anesthesiologist was actively participating in the care of the patient.

In some examples, the remote monitor with display 187, 287 allows long-distance medical consultation. For example, an expert at the Mayo Clinic could consult with a physician halfway around the world in Dubai, responding to real-time patient data displayed on the remote monitor with display 187, 287.

Figure 13:
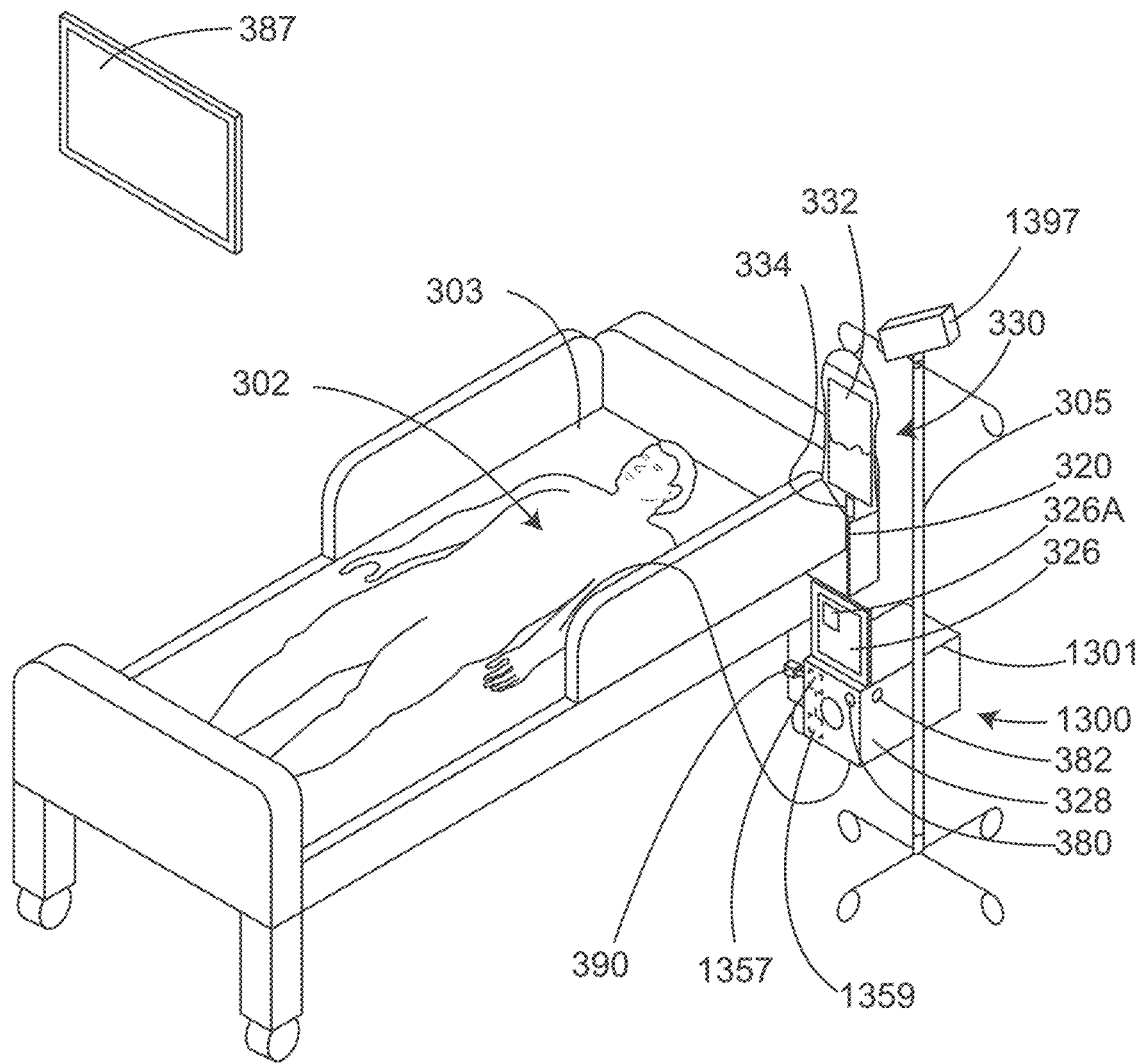
FIG. 13 illustrates an isometric view of another example module including a system for generating an automated electronic anesthetic record located proximate to a patient, in accordance with at least one example of this disclosure.
Figure 14:
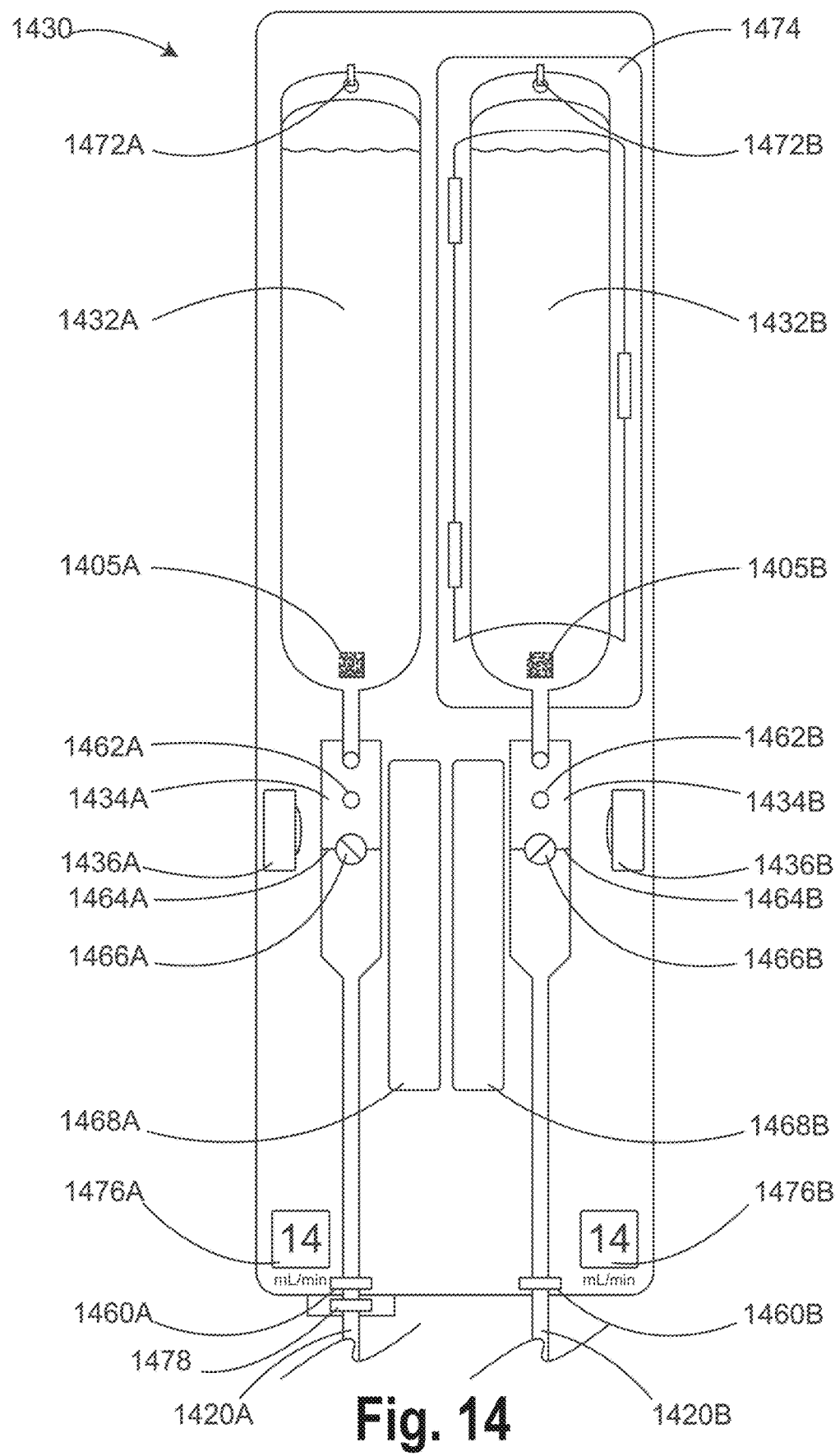
FIG. 14 illustrates a side view of an example IV fluid identification and measurement system that can be used with the systems of FIGS. 1 and 2, and injection port cassette of FIG. 10, in accordance with at least one example of this disclosure.

FIG. 14 illustrates a side view of an example IV fluid identification and measurement system 1430 that can be used with the systems of FIGS. 1-9, and the injection port cassette of FIG. 10. Some aspects of FIGS. 1-14 are described together, however, the examples are merely illustrative and the features can be used in any suitable combination. In some examples, the automated data consolidation module 100, 200 of this disclosure includes a system for automatically measuring and recording the administration of IV fluids. To accomplish this, as shown in FIGS. 1, 2 and 14, the automated data consolidation module 100, 200 can include an IV fluid identification and measurement system 130, 230, 1430. In some examples, the IV fluid identification and measurement system 130, 230, 1430 can be mounted onto module 101.

Alternately, the IV fluid identification and measurement system 130, 230, 1430 may be mounted to an IV pole 105 or racking system independent from the module 101. The system for automatically measuring and recording the administration of IV fluids is not limited to use in anesthesia or in the operating room, but has applicability for use throughout the hospital and other health care settings, including but not limited to the ICU, ER, wards, rehabilitation centers and long term care settings. In some examples, aspects of the IV fluid identification measurement system 130, 230, 1430 can be provided alone or together with other features of the automated data consolidation module 100, 200 including the medication identification and measurement system 128, 228.

In some examples, the IV fluid identification and measurement system 130, 230, 1430 may be configured to accommodate one or more bags of IV fluid 132, 232A,B and 1432A,B. Each bag of IV fluid can include a drip chamber 134, 234A,B and 1434A,B and IV tubing 120, 220A,B and 1420A,B. IV flow rates may be controlled with the traditional manually operated roller clamp that variably pinches the IV tubing 120, 220A,B and 1420A,B to control or even stop the flow of IV fluids. In some examples, IV flow rates may be controlled with the automatically operated electromechanical flow rate clamps 1478 that variably pinch the IV tubing 1420A to control or even stop the flow of IV fluids. The automatically operated electromechanical flow rate clamps 1478 may be controlled by the processing circuitry 157, 257, such as an electronic anesthetic record computer in module 101 or by any other suitable processor including hardware processing circuitry that is in electrical communication with the IV fluid identification and measurement system 130, 230, 1430 and/or is located within the IV fluid identification and measurement system 130, 230, 1430.

In some examples, the IV fluid identification and measurement system 130, 230, 1430 is configured to automatically measure and record the administration of IV medications and fluids. The system 130, 230 can include one or more of a barcode reader and an RFID interrogator (such as 1436A,B) for accurately and automatically identifying a fluid for IV administration. Because of the close proximity to the adjacent bags, barcode identification may be preferable in order to prevent an RFID interrogator from reading the RFID tag on a neighboring bag. In some examples, as shown in FIG. 14, one or more barcode labels 1405A,B may be applied to the IV bags 1432A,B in a location where they can be read by a sensor such as a barcode reader or machine vision camera 1436A,B, or another machine vision camera located in a suitable position to read the barcode. In some examples, a dedicated barcode reader or a machine vision camera may be positioned adjacent the barcode label 1405A,B location, specifically for reading the barcode label 1405A,B.

In some examples, the drip chamber 234A,B and 1434A,B of the IV set can be positioned adjacent the one or more machine vision cameras 1436A,B. In some examples, a standard background 1468A,B may be positioned on the opposite side of the drip chamber 1434A,B from the machine vision cameras 1436A,B. The standard background 1468A,B may be a plain background or may be an advantageous color, pattern, color design or illumination that highlights each of the falling drops, for easier identification by the processing circuitry 157, 257 (e.g., 1502, FIG. 15). The machine vision software including instructions can be stored on one or more machine-readable mediums (such as 1522 in FIG. 15) that when implemented on hardware processing circuitry (including but not limited to processing circuitry 157, 257) or in electrical communication with the system, can perform the functions described herein. An example of such electrical connection is shown by the connection of processor 1502 with mass storage 1516 in FIG. 15.

In some examples, the processing circuitry 157, 257, 1502 can be configured to look for (e.g., sense, monitor, detect) a fluid meniscus 1464A,B in the drip chamber 1434A,B. In this case "seeing" a fluid meniscus 1464A,B indicates that there is fluid in the drip chamber 1434A,B and therefore the IV bag 1432A,B is not empty, and air is not inadvertently entering the IV tubing 1420A, 1420B.

In some examples, if the IV fluid identification and measurement system 130, 230, 1430 fails to "see" a fluid meniscus 1464A,B meaning that the drip chamber 1434A,B is empty and thus the IV bag 1432A, B is empty, stop-flow clamps 1460A,B can be automatically activated. For example, processing circuitry 157, 257 can send an instruction to activate the stop-flow clamps 1460A,B to compress the IV tubing 1420A,B in order to prevent air from entering the IV tubing 1420A,B. In some examples, the empty IV bag 1432A,B condition detected by the processing circuitry 157, 257 can cause an alert to be displayed to the caregiver on the anesthetic record display 226, such as by sending an instruction to the display.

The combination of the machine vision camera 1436A,B in electrical communication with processing circuitry (e.g., 157, 257, FIGS. 1 and 2) that executes instructions stored on a machine readable medium can count the number of drops of fluid per unit of time in a drip chamber 1434A,B to calculate or to estimate the flow rate of an IV. The size of the drip chamber 1434A,B inlet orifice determines the volume of liquid in each drop. The inlet orifices of standard drip chambers are sized to create drops sizes that result in 10, 12, 15, 20, 45 and 60 drops per ml. Given a particular drop volume (size), 10 drops per ml for example, the system 130, 230, 1430 (e.g., via sensors, processing circuitry and machine readable medium) can count the number of drops falling in a known period of time and use that data to calculate or to estimate the flow rate. If these estimates were attempted by a human, they may be less accurate at higher flow rates (higher drop counts) because the drops are so fast, it can be difficult to count the drops. Eventually, at even higher flow rates the individual drops become a solid stream of fluid and the flow rate cannot be visually estimated.

In some examples, the IV fluid identification and measurement system 130, 230, 1430 is configured to look for falling drops of fluid 1462A,B within the drip chamber 1434A,B. When drops 1462A,B have been identified, the machine vision system (e.g., machine vision camera 1436A or 1436B operably coupled to processing circuitry 157, 257) may first measure the diameter of the drop 1462A,B to determine which of the standard drop sizes or volumes it is counting. Most hospitals standardize on several infusion set sizes, 10, 20 and 60 drops per cc for example. Therefore, when these limited choices of infusion set brands and sizes have been programed into the computer, the machine vision system only needs to differentiate between these choices, which is much easier than accurately measuring the diameter of the drops. Unlike the human eye, the machine vision can accurately count the falling drops even at high flow rates to calculate an IV fluid flow rate.

In some examples, the machine vision system, including the machine vision cameras 1436A,B and instructions 1524 (e.g., software) stored on a machine readable medium 1522 and implemented by hardware processing circuitry 157, 257 does not "see" falling drops 1462A,B. In this situation, either the fluid is flowing in a steady stream that is not identifiable or the fluid has stopped flowing. In some examples, these two opposite conditions can be differentiated by inserting a floating object 1466A,B (hereinafter, "float") into the drip chambers 1434A,B. In some examples, the float 1466A,B may be a ball-shaped float 1466A,B. In some examples, the float may be patterned or multi-colored to more easily identify movement or spinning of the float. In some examples, if the machine vision system cannot identify falling drops 1462A,B, it then looks to the float 1466A,B for additional information. If the float 1466A,B is not moving or spinning, the fluid flow has stopped. If the float 1466A,B is moving or spinning and drops cannot be identified, the fluid is flowing in a steady stream and the flow rate cannot be measured by machine vision. In this situation, the system can determine fluid flow using an alternate method.

In some examples, the IV fluid identification and measurement system 130, 230, 1430 may be configured to accommodate one or more bags of IV fluid 132, 232A,B, 1432A,B and each of these IV bags may be hanging from an electronic IV scale 1472A,B (e.g., a weight, a physical characteristic sensor). The electronic IV scale 1472A can measure the combined weight of the IV bag and fluid 1432A, the drip chamber 1434A and the IV tubing 1420A. The electronic IV scale 1472B can measure the weight or combined weight of one or more of the IV bag and fluid 1432B, the drip chamber 1434B, the IV tubing 1420B and a pressure infuser 1474. In both of these examples, the electronic IV scale 1472A,B can accurately measure the change in combined weight that occurs due to the drainage of the IV fluid from the IV bag 1432A,B. The change in weight per unit time can be converted to flow rates by processing circuitry 157, 257 in electrical communication with the electronic IV scale 1472A, 1472B, for example, by the processing circuitry 157, 257, 1502 and displayed on the electronic record display 126, 226.

In some examples, the calculated flow rates for each IV bag 1432A,B may also be displayed on one or more digital flow-rate displays 1476A,B mounted on the IV fluid identification and measurement system 1430. The digital flow-rate displays 1476A,B may be small LED or LCD displays that conveniently tell the operator the flow rate while they are manually adjusting the flow rate near the IV bags 1432A,B and drip chambers 1434A,B. The digital flow-rate displays 1476A,B are particularly convenient when the IV fluid identification and measurement system 130, 1430 is a free standing entity mounted on an IV pole 105 for example while being used on the ward or ICU.

In some examples, when the falling drops 1462A,B cannot be detected and yet the floats 1466A,B are moving or spinning, the fluid is determined to be flowing in a steady stream and the flow rate cannot be measured by machine vision. In this case the electronic record computer may automatically query the change in weight per unit time as measured by the electronic IV scale 1472A,B to determine the IV flow rate. At high flow rates, the change in weight per unit time as measured by the electronic IV scale 1472A, B will most likely be more accurate than counting drops, in determining the IV flow rate.

The IV flow rate as determined by the change in weight per unit time can also be compared to the IV flow rates determined by counting drops to verify the accuracy of each method. Without interfering with or changing the healthcare providers normal or traditional IV routines, an unobtrusive machine vision camera and computer can "observe" the IV flow rates and automatically record them in the EMR.

The module or automated EMR system 101, 201 of this disclosure may capture anesthetic event data but it must be noted that the same technologies described herein for capturing anesthetic event data can be used throughout the hospital or outpatient health care system to capture and record medication administration, IV fluid administration, vital signs and patient monitor inputs, provider events and other data. Non-operating room heath care locations are included within the scope of this disclosure. While this disclosure focuses on the totality of functions offered by module 101, 201, each of the individual functions can be offered independently of module 101, 201.

The use of the term Electronic Anesthetic Record (EAR) as defined herein can include any memory such as an electronic surgical record (ESR), or an electronic medical record (EMR), or an electronic health record (EHR), and is not limited to anesthetic or surgical applications. Aspects of the modules 101,201 described herein can also be employed in recovery, hospital room and long-term care settings.

In an example, the module 201 of FIG. 2, can include a housing 299 having a lower section 299A and a tower-like upper section 299B, wherein the lower section 299A can be configured to house unrelated waste heat-producing electronic and electromechanical surgical equipment, and wherein the tower-like upper section 299B can be located on top of the lower section 299A. The module 201 can also include a cowling 299C external or internal to the housing 299 that substantially confines waste heat generated by the unrelated waste heat-producing electronic and electromechanical surgical equipment. In addition, the module 201 can include a system for monitoring the administration of one or more IV medications and fluids 228, 230. As shown in the combination of FIGS. 2, 4, 5 and 14, the system 228, 230 can include any of: a barcode 436 reader or an RFID 438 interrogator configured to identify the one or more IV medications or fluids; a machine vision digital camera 436 to capture an image of one or more of a syringe 406 or a drip chamber 1434A,B; processing circuitry 257 operably coupled to the barcode reader 436 or the RFID interrogator 438 (or the machine vision digital camera 436) to receive the identity of the one or more IV medications or fluids, the processing circuitry 257 operably coupled to the machine vision digital camera 436 to receive the captured image and determine a volume of medication administered from the syringe or fluid administered from an IV bag based on the image; and a display 226 operably coupled to the processing circuitry 257, the display 226 configured to receive instructions from the processing circuitry 257 to output the identity and determined volume of medication administered from the syringe or fluid administered from an IV bag.

As described herein, "dose/response" can be a useful medical process. Dose-response includes giving something to the patient (a medicine for example) or doing something to the patient (mechanical ventilation or surgery for example)—the "dose", and then observing the patient's "response."

Healthcare data in general is manually entered, not automated. Healthcare data in general is also not granular (e.g., beat-by-beat, second-by-second, continuous) but rather very intermittent (e.g., every 15 minutes, every 4 hours, every day etc.). In general, most data in the EMR are simply data that was on the old paper record, manually entered into the EMR.

Manual data entry of dose events, whether they are reporting medication injections, fluid infusions or changes in the ventilator settings or any other "dose events" are laborious, distracting and universally disliked by healthcare providers. Perhaps more important is that the dose events are not accurately recorded. First, there are innocent errors in recording. Second, there are omissions that may be innocent or for lack of time or due to provider sloppiness. Finally, there is no temporal correlation between a dose event and a related response event because the dose event is most likely manually recorded minutes to hours after the dose event occurred (if it is recorded at all).

At this date, the only data that is automatic and timely recorded is the "response" data provided by the physiologic monitors. Even the monitor response data is usually not recorded beat-by-beat but rather intermittently recorded every 5 minutes or 30 minutes or 4 hours for example—just as it was historically recorded on the paper record. The remainder of the response data must be manually entered into the record and thus suffers from the same limitations as noted above for the manually entered dose events. As a result, with current EMRs the dose and response data cannot be temporally correlated with any accuracy, vastly reducing the analytical and predictive value of the electronic database and record. The systems described herein provide a technical solution to a technical problem. Furthermore, the benefits achieved by the technical solutions of this disclosure exceed what can be accomplished by manual processes.

In some examples, the automated data consolidation module 100,200 of this disclosure includes systems and methods for constructing granular (beat-by-beat, second-by-second) anesthetic, surgical and patient records that include both "dose" events—the things that are given or done to the patient (inputs from medication injection and fluid monitors, various support equipment and machine vision "observations" for example) and "response" events (inputs from electronic physiologic monitors, various measurement devices and machine vision "observations" for example). In some examples, the automated data consolidation module 100,200 of this disclosure automatically enters both dose and response events into the electronic record. In some examples, the dose and response events of this disclosure are continually recorded, creating a very granular record. Electronic memory has gotten so inexpensive that vast amounts of data can be practically recorded for analysis at a later time. In some examples, the dose and response event data of this disclosure that do not change very fast or frequently, may be continually recorded by the processing circuitry 157,257 but intermittently recorded in the EMR to reduce the size of the record.

In some examples, the automated data consolidation module 100,200 of this disclosure automatically enters both dose and response events into the electronic record and temporally correlates the dose and response events when they are recorded. Temporally correlating the dose and response data can be accomplished by recording dose and response data in parallel, adding integrated or external time stamps to the dose and response data or any other suitable method of temporally matching the data sets.

In an example, the module 201 of FIG. 2, can include a housing 299 having a lower section 299A and a tower-like upper section 299B, wherein the lower section 299A can be configured to house unrelated waste heat-producing electronic and electromechanical surgical equipment, and wherein the tower-like upper section 299B can be located on top of the lower section 299A. The module 201 can also include a cowling 299C external or internal to the housing 299 that substantially confines waste heat generated by the unrelated waste heat-producing electronic and electromechanical medical equipment. In some examples, the electronic and electromechanical medical equipment may be mounted on the module 201,101. In some examples, the electronic and electromechanical medical equipment may be in electrical communication with the module 201,101. In some examples, the electronic and electromechanical medical equipment may be wireless communication with the module 201,101.

In some examples, most of the electronic and electromechanical medical equipment that are in, on or connected to the module are either participants in dose events (something given to or done to the patient) or participants in response events (measuring or observing the patient's response). The physical location of the electronic and electromechanical medical equipment in or on the automated data consolidation module 100,200 of this disclosure, makes collecting data from the various equipment very efficient.

Unfortunately, most medical equipment available today does not produce a digital output signal that reports its operating settings and measurements in a recordable format. In some examples, the automated data consolidation module 100,200 allows rules to be applied to the various medical equipment that is housed within the module, mounted on the module, or is in electrical communication with or in wireless communication with the module. For example, the hospital or owner of the automated data consolidation module 100,200 could require that that all equipment in or on the module produce digital data reflecting the equipment's operating parameters and sensor inputs. Equipment manufacturers would have a business interest in adding digital outputs to their equipment if they want to sell their equipment to that hospital.

At this date there are few data standards for medical equipment and each manufacturer uses any data format that they choose. In some examples, the hospital or the owner of the "big data" database or the owner of the automated data consolidation module 100,200 could require that that all equipment in or on the module produce data in prescribed data standards and protocols so that translation of the data is not necessary. In some examples, the data standards would document the expectations for one or more of: format, definition, structuring, tagging, transmission, manipulation, use and management of the data. In some examples, the data standard defines entity names, data element names, descriptions, definitions, and formatting rules. Translating data from one data standard to another introduces the possibility of error. Therefore, producing data for input to the processing circuitry 157,257 in the prescribed standards and formats minimizes the opportunity for error by avoiding data translation. However, in some examples, the processing circuitry 157,257 of the automated data consolidation module 100,200 includes software for translating data when necessary.

In some examples, the hospital or the owner of the "big data" database or the owner of the automated data consolidation module 100,200 could require that all equipment in or on the module produce data to a prescribed data model that includes all relavent input record fields for that specific type of equipment. When data is used in "big data" databases, it is very common that there are missing data. The automated data consolidation module 100,200 of this disclosure can minimize missing data by using prescribed data models for each type of equipment and requiring that the data fields be filled. In some examples, the data standard or data model also prescribe the format of the data in each data field. Labeling the fields with consistent labels helps when AI analysis is done on the "big data."

In some examples, the hospital or the owner of the "big data" database or the owner of the automated data consolidation module 100,200 could require that that all equipment in or on the module produce data instantly. In some examples, instant data production is desirable so that the processing circuitry 157,257 can apply a time stamp or other time designation to the data so that the data can be temporally correlated with other data. Instant data production also allows stream processing to be performed on the data for real-time feedback. Automating data input is far superior to manual data input for many reasons. One of the important reasons is that automated input can accept and record high volume, instantaneous data production allowing temporal correlations between dose event data and response event data.

In some examples, consistent data standards, consistent data formatting, consistent data fields, consistent data labeling and time stamping, produces data for a "big data" database that is most usable for AI and ML analysis and research.

In some examples, consistent data standards, consistent data formatting, consistent data fields also produce data that is more protectable from the cyber security point of view. Having inputted structured and semi-structured data with consistent data standards, consistent data formatting, consistent data fields helps the processing circuitry 157,257 recognize inputted data that could be viral or malicious. In some examples, the processing circuitry 157,257 and software of the automated data consolidation module 100,200 can provide front line access control and firewall protection, preventing corrupt data from entering the system and being transferred to either the EMR or the "big data" database. In some examples, the processing circuitry 157,257 and software include one or more of access control software, firewall software, antivirus software, anti-malware, anti-spyware, anti-tamper software, anti-subversion software and other cyber security software.

If the thousands of monitors and other pieces of medical equipment in a hospital inputted their data directly to the EMR, it would be very challenging to provide cyber security on all of those inputs simultaneously. In some examples, since the automated data consolidation module 100,200 is receiving data inputs from only 2-30 pieces of medical equipment and sensors, cyber security is much more manageable. Therefore, it may be advantageous to use the processing circuitry 157,257 and software of the automated data consolidation module 100,200 to provide cyber security on the inputted data. When the inputted data is known to be secure, it can be freely transferred to the EMR or "big data" database without fear of corrupting the system.

In some examples, the hospital or the owner of the "big data" database or the owner of the automated data consolidation module 100,200 could require that that all equipment in or on the module produce data continuously. One of the "V's" of "big data" is volume—the more data the better. Therefore, in some examples, data and measurements that are changing may be recorded continuously to produce the most data "volume" for that data set. In some examples, the processing circuitry 157,257 and software can do data "filtering" in the presence of large size data to discard information that is not useful for healthcare monitoring based on defined criteria. This may include for example, intermittently recording data that changes slowly such as the patient's temperature, rather than continuously recording. In some examples, when the data is not changing or changing very slowly, for example the settings on a piece of equipment or the patient's temperature, the processing circuitry 157,257 may record the data into the EHR or "big data" database, intermittently for efficiency, without losing any "volume."

In some examples, the processing circuitry 157,257 and software can do data "cleaning" such as normalization, noise reduction and missing data management. "Sensor fusion" is a technique that may be utilized to simultaneously analyze data from multiple sensors, in order to detect and discard erroneous data from a single sensor. In some examples, the processing circuitry 157,257 and software can be used in many other ways to cleanse, organize and prepare the input data. Data "filtering" and data "cleaning" prepare the data to enhance the reliability of data mining techniques. Processing raw data without preparation routines may require extra computational resources that are not affordable in a "big data" context.

Figure 25:
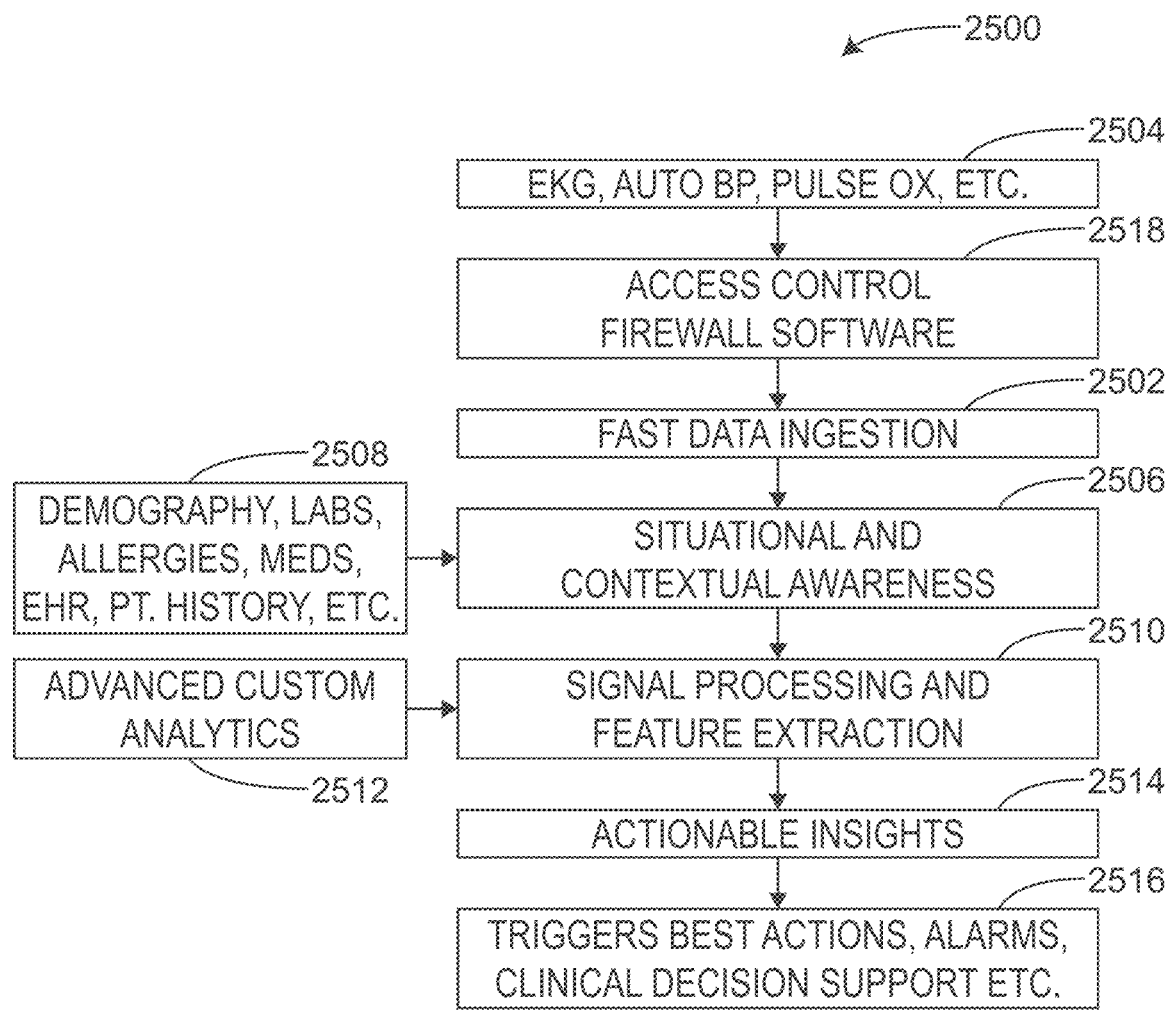
FIG. 25 is a flow chart illustrating a technique 2500 for assessing physiologic events, in accordance with at least one example of this disclosure.

In some examples, the processing circuitry 157,257 and software execute "stream processing" for applications requiring real-time feedback. In some examples, streaming data analytics in healthcare can be defined as a systematic use of continuous waveform and related medical record information developed through applied analytical disciplines, to drive decision making for the patient care. In some examples, as shown in FIG. 25, streaming healthcare data 2500 may start with fast data ingestion 2502 which may include continuous waveforms such as EKG or pulse oximetry or other non-waveform data such as blood pressure 2504. The next step in the process is situational and contextual awareness 2506, where the processing circuitry 157, 257 and software correlate and enrich the data set with data from the EHR, patient history, labs, allergies and medications and other data 2508. The next step in the process is signal processing and feature extraction 2510, where advanced analytics 2512 consume relevant data to produce insights. The final step in the process is producing actionable insight 2514, which can include clinical decision support and alarms 2516. In some examples, it is advantageous to regulate the access of incoming data with access control and firewall software 2518.

In some examples, when the objective is to deliver data to a "big data" database, the data must be pooled. Data in the "raw" state needs to be processed or transformed. In a service-oriented architectural approach, the data may stay raw and services may be used to call, retrieve and process the data. In the data warehousing approach, data from various sources is aggregated and made ready for processing, although the data is not available in real-time. The steps of extract, transform, and load (ETL) can be used to cleans and ready data from diverse sources. In some examples, it is most efficient for the processing circuitry 157,257 and software of the automated data consolidation module 100, 200 of this disclosure, to process and transform the raw data before sending it to the "big data" database.

Figure 26:
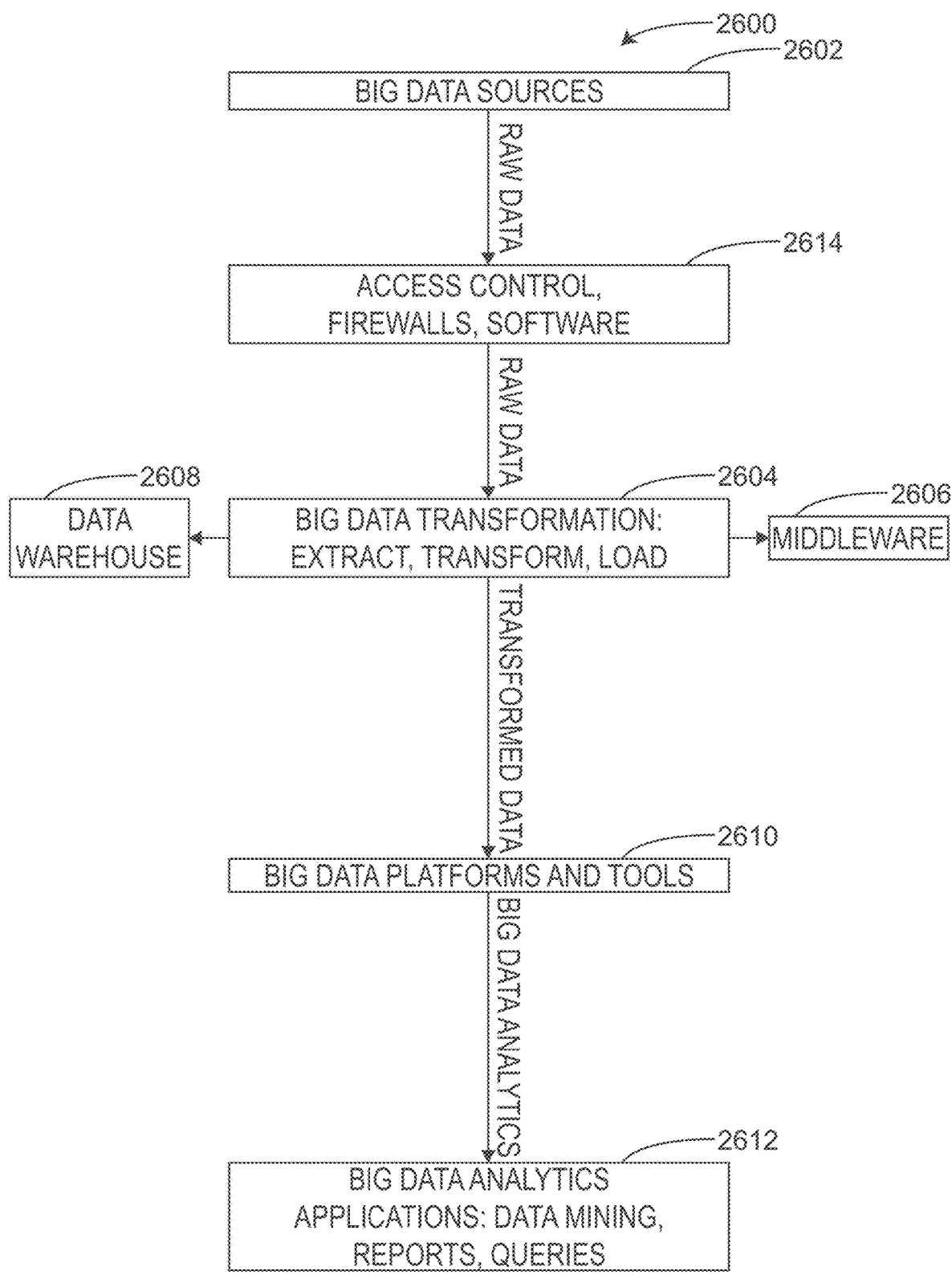
FIG. 26 is a flow chart illustrating a technique 2600 for creating big data, in accordance with at least one example of this disclosure.

In some examples, an applied conceptual architecture of big data analytics 2600 is shown in FIG. 26. Data from multiple sources 2602 can be inputted into the processing circuitry 157,257 and software of the automated data consolidation module 100,200. Big Data sources 2602 and data types include but are not limited to: Machine to machine data-readings from remote sensors, meters and other vital signs devices; big transaction data-health care claims and other billing records; biometric data-x-ray and other medical images, blood pressure, pulse and pulse-oximetry readings, and other similar types of data; human-generated data-unstructured and semi-structured data such as EMRs and physician notes. In some examples, it is advantageous to regulate the access of incoming data with access control and firewall software 2614.

In some examples, the processing circuitry 157,257 and software of the automated data consolidation module 100, 200 take the data and perform the steps of extract, transform, and load (ETL) 2604 to cleans and ready the data from diverse Big Data sources 2602. Once the data is processed or transformed, several options are available for proceeding with big data. A service-oriented architectural approach combined with web services (middleware) is one possibility 2606. The data stays raw and services are used to call, retrieve and process the data. Another approach is data warehousing 2608 wherein data from various sources is aggregated and made ready for processing. With data warehousing 2608 the data is not available in real-time.

Data transformation 2604 via the steps of extract, transform, and load (ETL), cleanses and readies the data from diverse sources 2602. Depending on whether the data is structured or unstructured, several data formats can be inputted to a big data analytics platform 2610. Big data is then organized into big data analytics applications 2612 such as queries, reports, OLAP and data mining, so that it can be useful.

In some examples, with "big data" database data, the processing circuitry 157,257 and software may execute "batch processing," analyzing and processing the data over a specified period of time. Batch processing aims to process a high volume of data by collecting and storing batches to be analyzed in order to generate results. In some examples, the processing circuitry 157,257 and software can serve as a "node" in batch computing, where big data is split into small pieces that are distributed to multiple nodes in order to obtain intermediate results. Once data processing by nodes is terminated, outcomes will be aggregated in order to generate the final results. In some examples, stream processing and batch processing may be both used, either in parallel or sequentially.

In some examples, the automatically entered, temporally correlated dose and response events in the patient's electronic medical record (EMR) may be analyzed by artificial intelligence (AI) and/or machine learning (ML) software in the processing circuitry 157,257 of the module for immediate advisory, alerts and feedback to the clinician. The patient's own data can be analyzed by AI algorithms that were derived from general medical knowledge and research or may be analyzed by AI algorithms that were derived from AI analysis of the pooled database of many patients, such as machine learning (ML) or a combination of the two.

In some examples, the automatically entered, temporally correlated dose and response events in the patient's electronic record may be pooled with the records of other patients in a database that can be analyzed with artificial intelligence and machine learning software stored on a memory and executed by processing circuitry. This analysis can occur at the time of temporal correlation or at a later time. This type of analysis is sometimes known as "big data." The pooled data (e.g. aggregated data, compiled data, such as collective data of a group of patients, collective data for a specific patient over different periods of time, doses, responses, medications, providers) may be stored on proprietary servers or may be stored in "the cloud." In any event, the "big data" database of this disclosure is complete and granular (compared to current healthcare databases) because it was automatically entered and at least some of the data is continually recorded. The "big data" database of this disclosure includes both dose events and response events (compared to current healthcare databases that are weighted toward response events) and the dose and response events are temporally correlated (compared to current healthcare databases). Temporal correlation can include time matching different sets of data streams.

"Big data" has been characterized by "four Vs": Volume, Velocity, Variety and Veracity. In some examples, the automated data consolidation module 100,200 of this disclosure addresses each of these characteristics in order to optimize the acquired data for "big data" use and analysis.

Volume—The more data you have the better it is. The automated data consolidation module 100,200 of this disclosure maximizes data volume by collecting data not only from the physiologic monitors but also all of the OR equipment and other dose events including machine vision video observations. Further, the automated data consolidation module 100,200 can provide either continuous recordings or intermittent recordings depending on the speed of change in the data and the usefulness of continuous data streams for any given data set or field.

Velocity—The data is accumulated in real-time and at a rapid pace. The automated data consolidation module 100,200 of this disclosure maximizes data velocity by automatically recording everything which removes manual data entry that slows the data acquisition process down. The ability to perform real-time analytics against such high-volume data in motion could revolutionize healthcare.

Variety—How different is the data. The automated data consolidation module 100,200 of this disclosure maximizes data variety by recording most if not all structured and semi-structured data sources in the OR or other care locations, including but not limited to: physiologic monitors, equipment, medication injections, dose events, response events, fluids and video with artificial intelligence (AI) and/or machine learning (ML) analysis of the patient and delivered care. In some examples, the automated data consolidation module 100,200 may also accept unstructured textual data entered by a keyboard, natural language voice recognition, from the EMR/EHR or other suitable source.

Veracity—How accurate is the data, the truthfulness of the data. The automated data consolidation module 100,200 of this disclosure maximizes data veracity by automatically recording the data without requiring human input. In some examples, the automated data consolidation module 100,200 of this disclosure includes Sensor Fusion, a data analytic system that monitors input data in order to reject clearly mistaken inputs such as might occur if an EKG lead comes lose for example—improving the veracity of the database. Sensor Fusion analyzes the input data from multiple sensors simultaneously in order to detect and reject inputs that are clearly erroneous. In some examples, Sensor Fusion may include a threshold-controlled artifact-removal module and/or a Kalman filter using statistical analysis to compare the input data streams.

In some examples, the automated data input feature of the automated data consolidation module 100,200 is particularly important because the increased variety of data input and high velocity of data input hinder the ability to cleanse data before analyzing it and making decisions, magnifying the issue of data "trust." The mere fact that the input is automatic decreases the opportunity for human error.

In some examples as shown in FIGS. 1 and 2, module 101,201 of the automated data consolidation module 100,200 may consolidate a wide variety of equipment used for anesthesia and surgery. Some of this equipment, including but not limited to: the physiologic monitors, the urine output monitor and the blood loss monitor and video observation of the patient with AI and/or ML analysis to produce response event data that can be automatically recorded by the automated data consolidation module 100,200.

In some examples as shown in FIGS. 1 and 2, module 101,201 of the automated data consolidation module 100,200 may consolidate a wide variety of equipment that produce dose event data, including but not limited to: medication identification and measurement system 128,228 and the IV fluid identification and measurement system 130,230, gas flow meters (not shown), the mechanical ventilator (not shown), the pneumoperitoneum insufflator (not shown), the electrosurgical generator (not shown) and video observation of the patient and provider with AI and/or ML analysis to produce dose event data that can be automatically recorded by the automated data consolidation module 110,200 (e.g., dose event data can be received by processing circuitry 157, 257 and stored on one or more storage devices).

The automated data consolidation module 100,200 not only physically consolidates various electrical and electro-mechanical equipment but also consolidates the data outputs of the various equipment for easy electrical communication with the processing circuitry 157, 257. The consolidation of equipment in and on the module 101,201 of the automated data consolidation module 100,200 solves another practical obstacle currently preventing an automated dose/response record. Currently, much of the equipment mentioned above does not produce digital data that documents the equipment's operation because the various equipment manufacturers have chosen not to provide output data. The practical solution is that the provider of the automated data consolidation module 100,200 can require that any equipment that is to be located in or on the module 101,201, must include data outputs and the provider can also prescribe the digital standard and format so that the data can be organized efficiently and completely in a "big data" database. These benefits are not provided in any conventional system.

In some examples, it is anticipated that the automated data consolidation module 100,200 can also accept input data from other medical equipment and data sources by either wired or wireless connections. As with the equipment housed within or on the automated data consolidation module 100,200, it is preferable if the input data follows the digital standard and format applied to the other equipment. However, in some examples the processing circuitry 157, 257 can translate input data that is not in the desired digital standard or format.

Machine vision cameras and software are very good at measuring distances, movements, sizes, looking for defects, fluid levels, precise colors and many other quality measurements of manufactured products. Machine vision cameras and software can also be "taught" through AI and ML to analyze complex and rapidly evolving scenes such as those in front of a car driving down the road. Machine vision cameras and software don't get bored or distracted.

Figure 12:
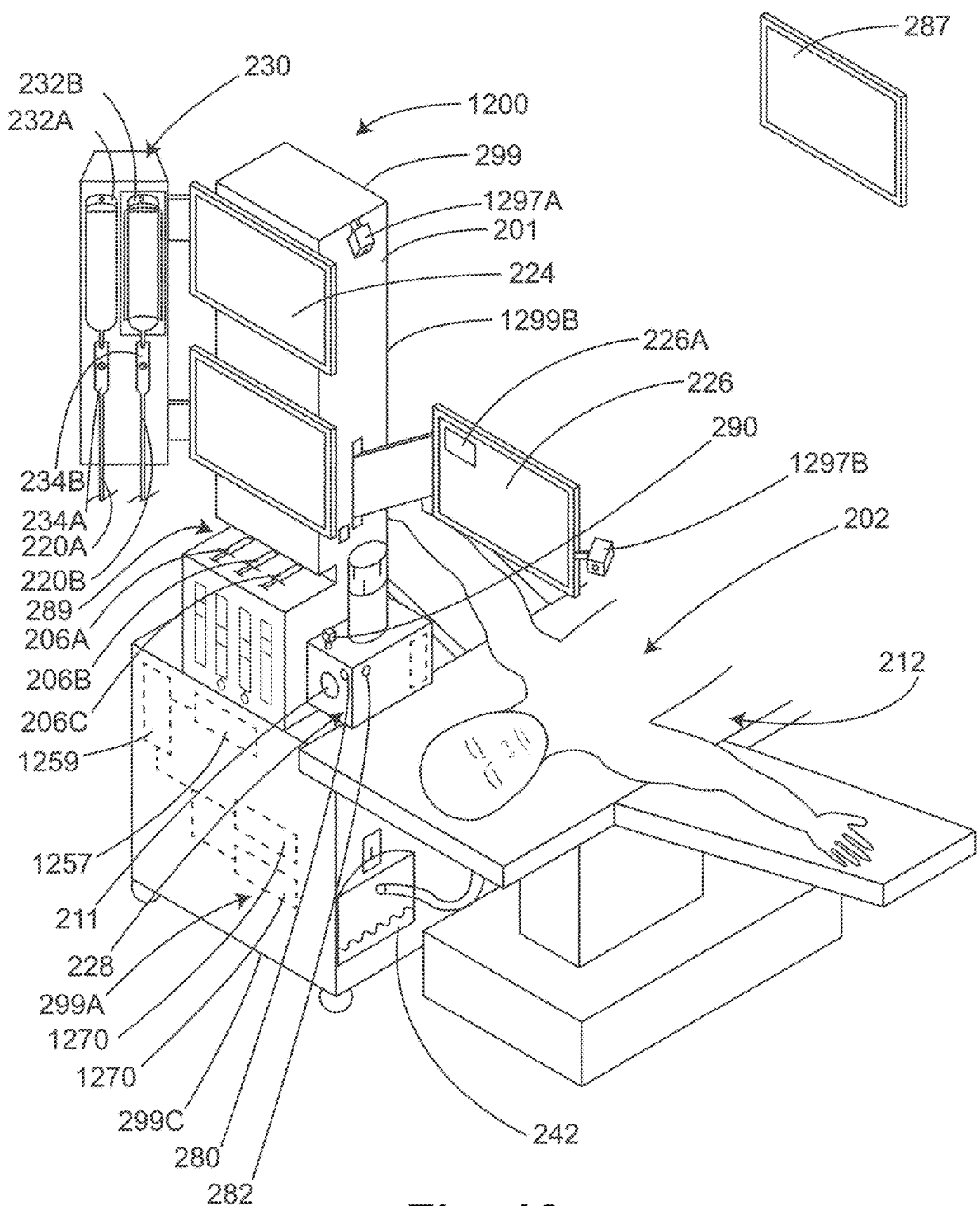
FIG. 12 illustrates an isometric view of another example module including a system for generating an automated electronic anesthetic record located proximate to a patient, in accordance with at least one example of this disclosure.

FIG. 12 illustrates an isometric view of another example module 1201 including an automated data consolidation module 1200 for generating an automated electronic anesthetic record located proximate to a patient.

In some examples as shown in FIG. 12, the automated data consolidation module 1200 of this disclosure includes systems and methods for using machine vision cameras 1299A,B and software to "observe" the patient. If the patient is in surgery, the patient's head may be the focus of the observation. In some examples, during surgery the machine vision cameras 1299A,B and software may be "looking" for dose events including but not limited to mask ventilation, endotracheal intubation or airway suctioning. In other words, the machine vision cameras 1299A,B can generate and send dose event information to be received and analyzed by processing circuitry 157, 257.

In some examples, during surgery the machine vision cameras 1299A,B and software may be "looking" for (e.g., monitoring, sensing, detecting) response events including but not limited to: movement, grimacing, tearing or coughing or changes in skin color or sweating. In other words, the machine vision cameras 1299A,B can generate and send response event information to be received and analyzed by processing circuitry 157, 257. Movement, grimacing, tearing and coughing are all signs of "light" anesthesia and that the patient may be in pain. Subtle changes in skin color from pinkish to blueish or grayish may indicate inadequate oxygenation or low perfusion. Subtle changes in skin color from pinkish to reddish may indicate hyperthermia or an allergic reaction. Sweating may indicate inadequate perfusion or hyperthermia. In any event, observing the patient is regarded by the American Society of Anesthesiologists as the most basic of all monitors. Machine vision cameras 1299A,B and software do not get bored and can be programed to recognize subtle changes that may be missed by the human observer. Both movements and skin color changes may be subtle. The baseline color may be very difficult for the observer to remember, whereas the machine vision cameras 1299A,B and software can precisely "remember" the baseline color and recognize even subtle changes over time. In some examples, pain may be detected by facial expression analysis, such as by processing circuitry 1257 receiving response event information from the machine vision cameras 1299A, B, analyzing such response event information, and recording or displaying the information, or alerting a clinician or other personnel via a user interface, such as the display 1226 or the remote display 1287, shown in FIG. 12.

In some examples, vital signs such as heart rate, respiration rate, blood oxygen saturation and temperature can be measured remotely via camera-based methods. Vital signs can be extracted from the optical detection of blood-induced skin color variations-remote photoplethysmography (rPPG). In some examples, this technique works best using visible light and Red Green Blue (RBG) cameras. However, it has also been shown to work using near-infrared light (NIR) and NIR cameras. Just like pulse oximetry, a well-known technology for detecting pulse and blood oxygen saturation, rPPG relies on the varying absorption of different wavelengths of light caused by blood volume changes and the oxygen saturation of the blood in the small blood vessels beneath the skin. Unlike pulse oximetry that needs to be in contact with the skin, rPPG enables contactless monitoring of human cardiac activities by detecting the pulse-induced subtle color changes on the human skin surface using a regular RBG camera.

In some examples, this disclosure anticipates automating the remote photoplethysmography using techniques such as, but not limited to, region of interest (RoI) detection and full video pulse extraction (FVP). In some examples, this disclosure also anticipates using a combination of visible light and near-infrared light wavelengths to detect different parameters. In some examples, additional measurements are anticipated using the rPPG technology including but not limited to measuring blood glucose and hemoglobin levels.

FIG. 13 illustrates an isometric view of yet another example module 1301 including an automated data consolidation module 1300 for generating an automated electronic record located proximate to a patient.

In some examples as shown in FIG. 13, if the patient is on the ward, in the nursing home or other long-term care facility or at home, the whole patient may be the focus of the observation. In some examples, if the patient is on the ward, in the nursing home or other long-term care facility, or at home, the machine vision cameras 1399 and software may be "looking" for (e.g., sensing, monitoring, detecting) dose events including but not limited to repositioning the patient or suctioning the airway, feeding and eating, or assisting the patient out of bed or any other nursing procedure.

In some examples, if the patient is on the ward, in the nursing home or other long-term care facility, or at home, the machine vision cameras 1399 and software may be "looking" (e.g., sensing, monitoring, detecting) for response events including but not limited to restlessness or getting out of bed without assistance, coughing or changes in the breathing pattern or changes in skin color. Recent research has shown that machine vision cameras 1399 and software with AI can recognize moods with reasonable accuracy. The patient's mood could be an important response event that should be recorded.

Figure 24:
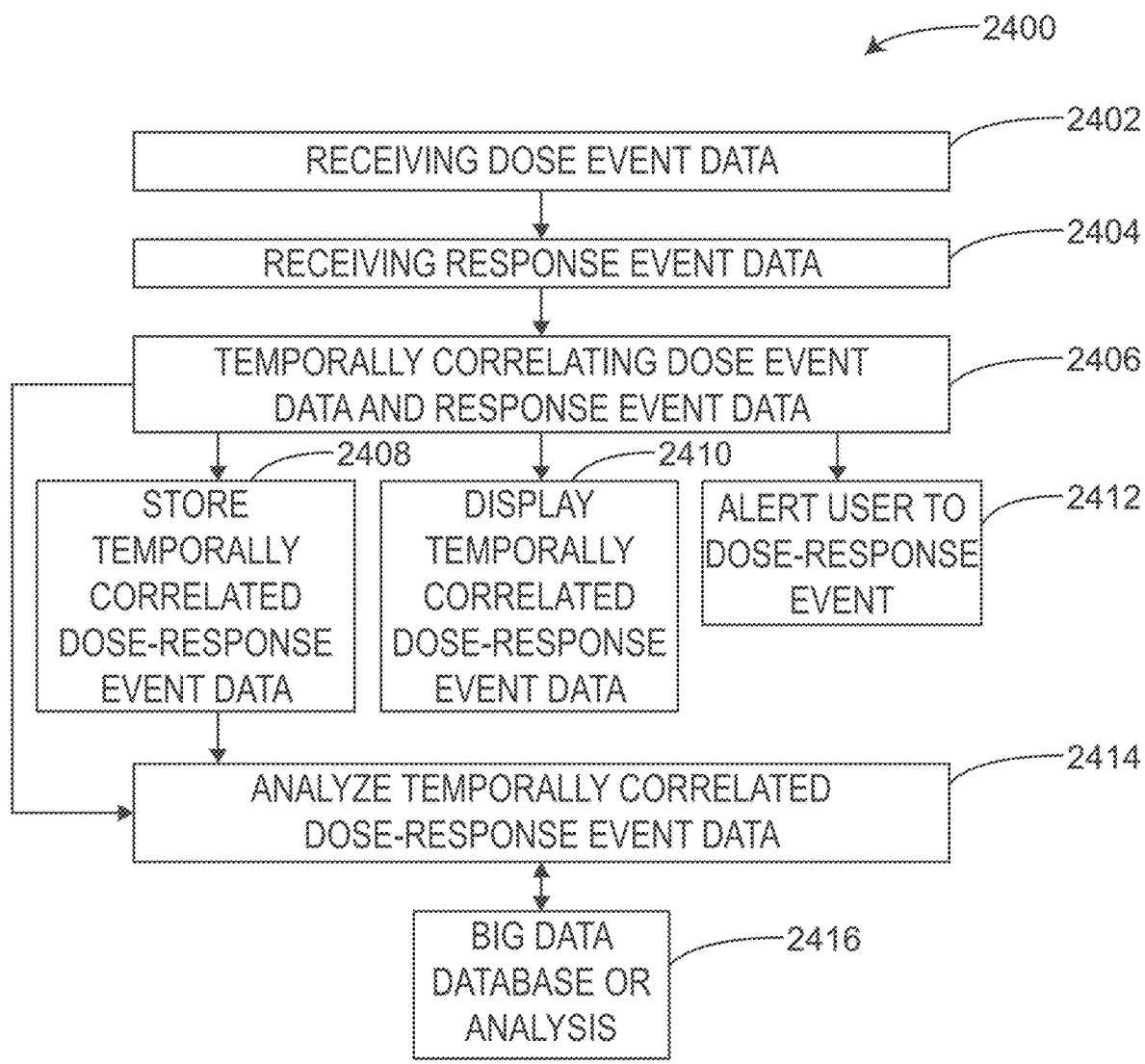
FIG. 24 is a flow chart illustrating a technique 2400 for assessing physiologic events, in accordance with at least one example of this disclosure.

As shown in technique 2400 of FIG. 24, various operations can be performed by the dose-response systems 100, 200, 1200, 1300 and subsystems disclosed herein. While the technique 2400 can be performed by the dose-response systems 100, 200, 1200, 1300, the technique 2400 can also be performed by other systems, and the systems 100, 200, 1200, 1300 can perform other techniques. In an example, a dose-response system can perform technique 2400 using processing circuitry and one or more storage devices including a memory. The memory can have instructions stored thereon, which when executed by the processing circuitry cause the processing circuitry to perform the operations. For example, operation 2402 can include receiving dose information (or dose event) from one or more sensors. Operation 2404 can include receiving response information (or response event) from one or more sensors. The dose information can include data corresponding to a dose provided to the patient, and the response information can include data corresponding to a response of the patient. Operation 2406 can include temporally correlating the dose information and the response information. Operation 2408 can include saving the temporally correlated dose-response information to at least one of the one or more storage devices such as storage device 1516 of FIG. 15. Temporally correlating dose-response information can include continuously temporally correlating the dose-response information, such as in a processor-based timer, in a beat-by-beat, second-by-second type manner, as opposed to the extended intervals and less accurate methods of traditional medical practice. In some examples, temporally correlating the dose-response information includes temporally correlating the dose-response information, such as in a range between every 0.1 seconds to 5 minutes. In some examples, it may be preferable to temporally correlate in a range between every 0.1 seconds to 1 minute. It may be more preferable to temporally correlate in a range between every 1 second to 1 minute, however, any suitable temporal correlation may be used to facilitate accurate, safe and meaningful correlation where a direct, time-based relationship between the dose and the response is captured.

In some examples, operation 2410 can include displaying information corresponding to the dose-response data. In operation 2412, if the processing circuitry detects a concerning response, the processing circuitry can alert a user to the response. Operation 2414 can include analyzing the temporally correlated data. In some examples, operation 2414 can include aggregating the temporally correlated dose-response information with temporally correlated dose-response information collected from other patients. In some examples, operation 2414 can include aggregating the temporally correlated dose-response information with temporally correlated dose-response information collected from the same patient over a different period of time. Comparing data from the same patient may allow a provider to detect when a patient develops a tolerance to a drug, such as a pain killer. In an example, if the rate of grimacing by the patient increases or they start to grimace sooner (e.g., response) after being given a pain medication (dose), as the pain medication is given over different days, weeks and months. Operation 2414 can also facilitate machine learning.

In technique 2400, the dose information can include data/events generated by one or more of: an RFID interrogator, a barcode reader, a QR reader, a machine vision digital camera, any combination thereof, or any other suitable sensor. The response information can include data/events generated by a machine digital camera or any other suitable sensor. The response information can include an image of one or more movements, secretions or skin color changes, and the processing circuitry can be configured to identify changes in the response information. In some examples the processing circuitry can use machine learning to identify changes in the response information. In some examples, the response information includes physiologic data generated by a physiologic monitor. For example, the physiologic data can include at least one of: electrocardiogram, pulse oximetry, blood pressure, temperature, end-tidal $CO_2$, expired gases, respiratory rate, hemoglobin, hematocrit, cardiac output, central venous pressure, pulmonary artery pressure, brain activity monitor, sedation monitor, urine output, blood loss, blood electrolytes, blood glucose, blood coagulability, train-of-four relaxation monitor data, IV extravasation monitor data and body weight, and any combination thereof or other suitable physiologic data.

Implementation of any of the techniques described herein may be done in various ways. For example, these techniques may be implemented in hardware, software, or a combination thereof. For a hardware implementation, the processing units may be implemented within on or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Furthermore, embodiments may be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks may be stored in a machine-readable medium such as a storage medium. A code segment or machine-executable instruction may represent a procedure, a function, a subprogram, a program, a routine, a subroutine, a module, a software package, a script, a class, or any combination of instructions, data structures, and/or program statements. A code segment may be coupled to another code segment or a hardware circuit by passing and/or receiving information, data, arguments, parameters, and/or memory contents. Information, arguments, parameters, data, etc. may be passed, forwarded, or transmitted via any suitable means including memory sharing, message passing, token passing, network transmission, etc.

For a firmware and/or software implementation, the techniques may be implemented with modules (e.g., procedures, functions, and so on) that perform the functions described herein. Any machine-readable medium tangibly embodying instructions may be used in implementing the techniques described herein. For example, software codes may be stored in a memory. Memory may be implemented within the processor or external to the processor. As used herein the term "memory" refers to any type of long term, short term, volatile, nonvolatile, or other storage medium and is not to be limited to any particular type of memory or number of memories, or type of media upon which memory is stored.

There are two common modes for ML: supervised ML and unsupervised ML. Supervised ML uses prior knowledge (e.g., examples that correlate inputs to outputs or outcomes) to learn the relationships between the inputs and the outputs. The goal of supervised ML is to learn a function that, given some training data, best approximates the relationship between the training inputs and outputs so that the ML model can implement the same relationships when given inputs to generate the corresponding outputs. Unsupervised ML is the training of an ML algorithm using information that is neither classified nor labeled, and allowing the algorithm to act on that information without guidance. Unsupervised ML is useful in exploratory analysis because it can automatically identify structure in data. Either of supervised ML or unsupervised ML can be used to train the systems described herein to correlate information from one or more sensors, such as a machine vision digital camera as having a particular meaning. For example, either of supervised or unsupervised ML can be used to train the systems to correlate facial expressions with response events. The system can be trained to "read" a particular patient, or a group of patients that may or may not include the particular patient being monitored.

Common tasks for supervised ML are classification problems and regression problems. Classification problems, also referred to as categorization problems, aim at classifying items into one of several category values (for example, is this object an apple or an orange?). Regression algorithms aim at quantifying some items (for example, by providing a score to the value of some input). Some examples of commonly used supervised-ML algorithms are Logistic Regression (LR), Naive-Bayes, Random Forest (RF), neural networks (NN), deep neural networks (DNN), matrix factorization, and Support Vector Machines (SVM).

Some common tasks for unsupervised ML include clustering, representation learning, and density estimation. Some examples of commonly used unsupervised-ML algorithms are K-means clustering, principal component analysis, and autoencoders.

Figure 15:
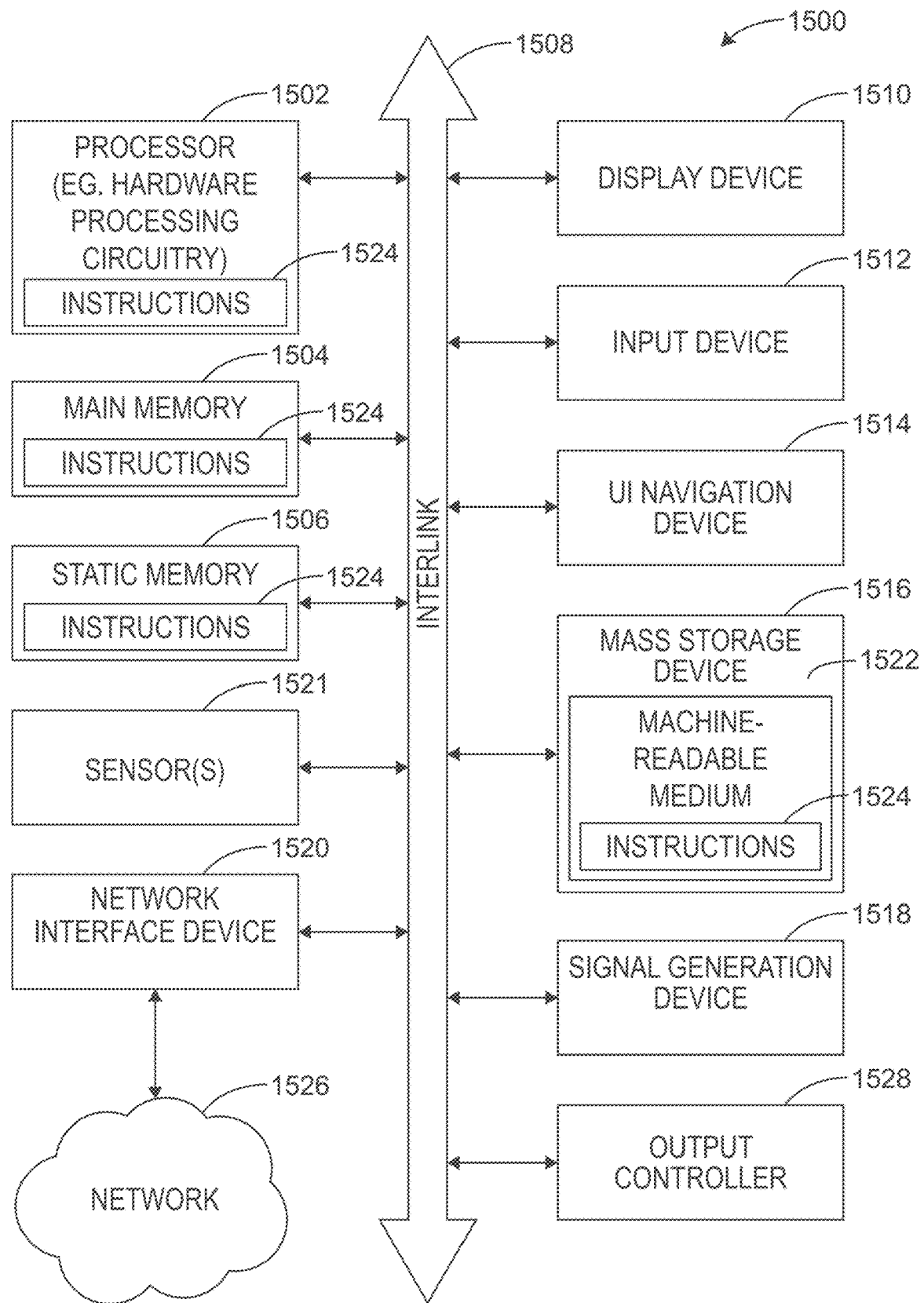
FIG. 15 illustrates generally an example of a block diagram of a machine (e.g., of module 101, 201) upon which any one or more of the techniques (e.g., methodologies) discussed herein may perform in accordance with at least one example of this disclosure.

FIG. 15 illustrates an example electronic and/or electromechanical system 1500 of a medical system in accordance with some examples described herein. The system 1500 will be described with respect to the automated data consolidation module 100, 200, but can include any of the features described herein to perform any of the methods or techniques described herein, for example, by using the processor 1502. The processor can include processing circuitry 157 or 257 of FIGS. 1 and 2. In some examples, the processing circuitry 1502 can include but is not limited to, electronic circuits, a control module processing circuitry and/or a processor. The processing circuitry may be in communication with one or more memory and one or more storage devices. A single processor can coordinate and control multiple, or even all the aspects of the system 1500 (e.g., of modules 101, 201), or multiple processors can control all the aspects of the system 1500. In some examples the storage device 1516 or memory 1504, 1506, 1516 can include at least a portion of the patient's anesthetic record saved thereon. The system 1500 can also include any of the circuitry and electronic and/or electromechanical components described herein, including but not limited to, any of the sensor(s) described herein (e.g., sensors 1521), such as but not limited to, RFID barcode or QR codes sensors, machine vision cameras, retinal scanners, facial recognition scanners, fingerprint readers, actuators and position sensors described herein. The system 1500 may also include or interface with accessories or other features such as any of: a remote display or wireless tablet (e.g., 287, FIG. 2), as well as any of the other systems described herein.

The processing circuitry 1502 can receive information from the various sensors described herein, make various determinations based on the information from the sensors, output the information or determinations from the information for output on the display or wireless tablet, output instructions to provide an alert or an alarm, power various components, actuate actuators such as clamps and flow managing devices, etc., or alert another system or user, as described herein. For the sake of brevity, select systems and combinations are described in further detail above and in the example sets provided in the Notes and Various Examples section below. Other embodiments are possible and within the scope of this disclosure.

Further, FIG. 15 illustrates generally an example of a block diagram of a machine (e.g., of module 101, 201) upon which any one or more of the techniques (e.g., methodologies) discussed herein may be performed in accordance with some embodiments. In alternative embodiments, the machine 1500 may operate as a standalone device or may be connected (e.g., networked) to other machines. In a networked deployment, the machine 1500 may operate in the capacity of a server machine, a client machine, or both in server-client network environments. The machine 1500, or portions thereof may include a personal computer (PC), a tablet PC, a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate on, logic or a number of components, modules, or like mechanisms. Such mechanisms are tangible entities (e.g., hardware) capable of performing specified operations when operating. In an example, the hardware may be specifically configured to carry out a specific operation (e.g., hardwired). In an example, the hardware may include configurable execution units (e.g., transistors, circuits, etc.) and a computer readable medium containing instructions, where the instructions configure the execution units to carry out a specific operation when in operation. The configuring may occur under the direction of the execution units or a loading mechanism. Accordingly, the execution units are communicatively coupled to the computer readable medium when the device is operating. For example, under operation, the execution units may be configured by a first set of instructions to implement a first set of features at one point in time and reconfigured by a second set of instructions to implement a second set of features.

Machine (e.g., computer system) 1500 may include a hardware processor 1502 (e.g., processing circuitry 157, 257, a central processing unit (CPU), a graphics processing unit (GPU), a hardware processor core, or any combination thereof), a main memory 1504 and a static memory 1506, some or all of which may communicate with each other via an interlink (e.g., bus) 1508. The machine 1500 may further include a display unit 1510, an alphanumeric input device 1512 (e.g., a keyboard), and a user interface (UI) navigation device 1514 (e.g., a mouse). In an example, the display device 1510, an input device such as an alphanumeric input device 1512 and UI navigation device 1514 may be a touch screen display. The display unit 1510 may include goggles, glasses, or other AR or VR display components. For example, the display unit may be worn on a head of a user and may provide a heads-up-display to the user. The alphanumeric input device 1512 may include a virtual keyboard (e.g., a keyboard displayed virtually in a VR or AR setting.

The machine 1500 may additionally include a storage device (e.g., drive unit) 1516, a signal generation device 1518 (e.g., a speaker), a network interface device 1520, and one or more sensors 1521, such as a global positioning system (GPS) sensor, compass, accelerometer, or other sensor. The machine 1500 may include an output controller 1528, such as a serial (e.g., universal serial bus (USB), parallel, or other wired or wireless (e.g., infrared (IR), near field communication (NFC), etc.) connection to communicate or control one or more peripheral devices or actuators of the system. Peripheral devices can include but are not limited to any displays, controllers or memories in electrical communication with the system, and actuators can include but are not limited to: one or more stop-flow clamps 1060A,B (FIG. 10) and one or more flow rate clamps 1478 (FIG. 14) of the system.

The storage device 1516 may include a machine readable medium 1522 that is non-transitory on which is stored one or more sets of data structures or instructions 1524 (e.g., software) embodying or utilized by any one or more of the techniques or functions described herein. The instructions 1524 may also reside, completely or at least partially, within the main memory 1504, within static memory 1506, or within the hardware processor 1502 during execution thereof by the machine 1500. In an example, one or any combination of the hardware processor 1502, the main memory 1504, the static memory 1506, or the storage device 1516 may constitute machine readable media that may be non-transitory.

While the machine readable medium 1522 is illustrated as a single medium, the term "machine readable medium" may include a single medium or multiple media (e.g., a centralized or distributed database, or associated caches and servers) configured to store the one or more instructions 1524.

The term "machine readable medium" may include any medium that is capable of storing, encoding, or carrying instructions for execution by the machine 1500 and that cause the machine 1500 to perform any one or more of the techniques of the present disclosure, or that is capable of storing, encoding or carrying data structures used by or associated with such instructions. Non-limiting machine-readable medium examples may include solid-state memories, and optical and magnetic media. Specific examples of machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 1524 may further be transmitted or received over a communications network 1526 using a transmission medium via the network interface device 1520 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, peer-to-peer (P2P) networks, among others. In an example, the network interface device 1520 may include one or more physical jacks (e.g., Ethernet, coaxial, or phone jacks) or one or more antennas to connect to the communications network 1526. In an example, the network interface device 1520 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 1500, and includes digital or analog communications signals or other intangible medium to facilitate communication of such software.

Method examples described herein may be machine or computer-implemented at least in part. Some examples may include a computer-readable medium or machine-readable medium encoded with instructions operable to configure an electronic device to perform methods as described in the examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

Some of the benefits of the automated data consolidation module 100, 200 of FIGS. 1 and 2 and the subsystems described throughout this disclosure, and including the machine 1500 (FIG. 15), can include features to help with monitoring medication, fluid and anesthesia delivery, as well as documenting medication, fluid and anesthesia delivery, as well as other functions. In general, doctors and nurses are not interested in replacing themselves and their jobs with automated drug delivery or automated anesthesia systems. However, there is great interest in automated record keeping. Virtually all healthcare providers would prefer the "old" paper record and a pen to the "new" computer records. Filling out the electronic medical record (EMR) using a computer keyboard, mouse and various menus is widely viewed as a slow, cumbersome and distracting process. The challenge with automated record keeping is automating the data input that documents the numerous activities, anesthesia related events, fluid, gas and medication administration, ventilator settings, pressure off-loading effectiveness, as well as outputs such as blood loss and urine output, that constitute an anesthetic experience.

A challenge in implementing the automated data consolidation module 100, 200 with an automated electronic anesthetic record (EAR) or electronic medical record (EMR) is to force as little change in the caregiver's routine as possible onto the clinicians using this system. Medical personnel tend to be creatures of habit and tradition and they generally do not like change. For example, IV medications are traditionally administered from a syringe and the dose is determined by the caregiver observing the plunger moving relative to a scale printed on the syringe. Maintaining this general technique of drug administration may have the highest probability of acceptance by healthcare users who are typically slow to embrace changes in their routine.

Further, with regard to benefits of the modules, systems and machines described herein, the automated data consolidation module 200 of module 201 can generate an automated electronic medical record (EMR) with the module 201 locatable proximate to the patient 202. The module 201 can be a module for housing unrelated electronic and electromechanical surgical equipment. The module 201 need not necessarily be configured to house unrelated electronic and electromechanical surgical equipment in all examples, and other modules can include the system for generating an automated EMR.

The module 201 can be an automated EMR system that can include one or more systems (e.g., 200, 228, 230) configured to measure (e.g., monitor) and record one or more of functions involved in a surgical anesthetic environment, and can include life support functions. The one or more systems 228, 230 can measure and record data automatically. However, in some examples, a user may initiate any of the systems described herein to measure and/or record data. These various measurements may be electronically recorded (such as on mass storage 1516 (FIG. 15) and displayed on the electronic anesthetic record display 226 (e.g., display device 1510, FIG. 15). Inputs to the automated EMR system may be managed by the anesthetic record input component 224 (e.g., input device 1512; FIG. 15). The anesthetic record input component 224 (e.g., input device 1512; FIG. 15) can include a touch-screen display 226 that organizes all of the inputs to the EMR into easily accessed and utilized information. In some examples, and as shown in FIG. 2, the identification and measurement system 228 of this disclosure may be located proximate the patient 202. The control displays for the identification and measurement system 228 may include a dedicated display proximate the identification and measurement system 228 or may be shared space on the anesthetic record input component 224 or display 226. In these locations, the information and controls of the identification and measurement system 228 can be viewed by the anesthesiologist or other user, in a single field of vision with the patient and surgical field.

Example methods of employing the systems, modules and machines disclosed herein are described throughout this disclosure and in the methods of FIGS. 16-21 which are illustrative in nature. Other methods described herein may also be performed by the systems, modules and machines described herein, and the systems modules and machines described herein may be used to perform other methods.

Figure 16:
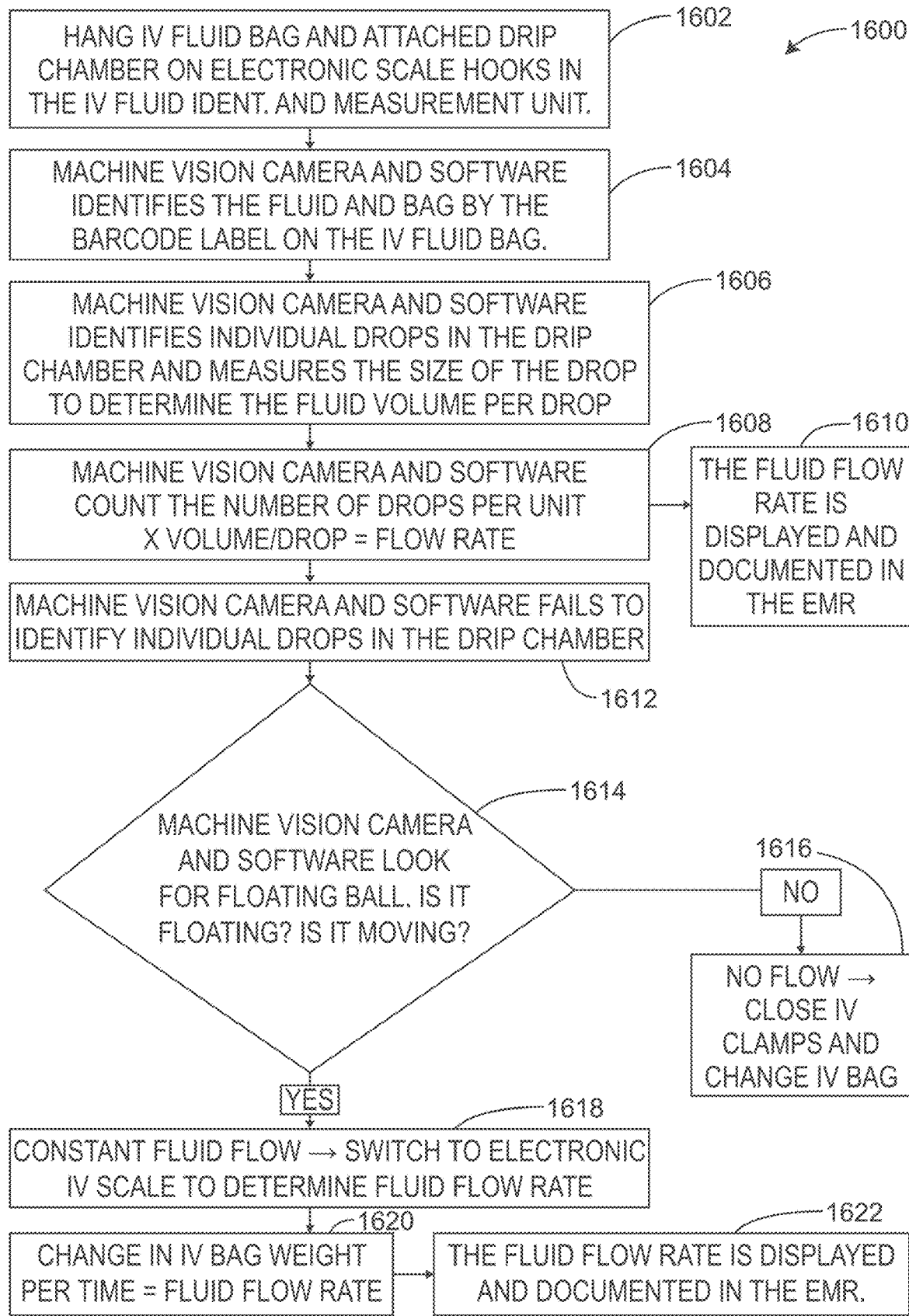
FIG. 16 is a flow chart illustrating a technique of IV fluid identification and measurement, in accordance with at least one example of this disclosure.
Figure 17:
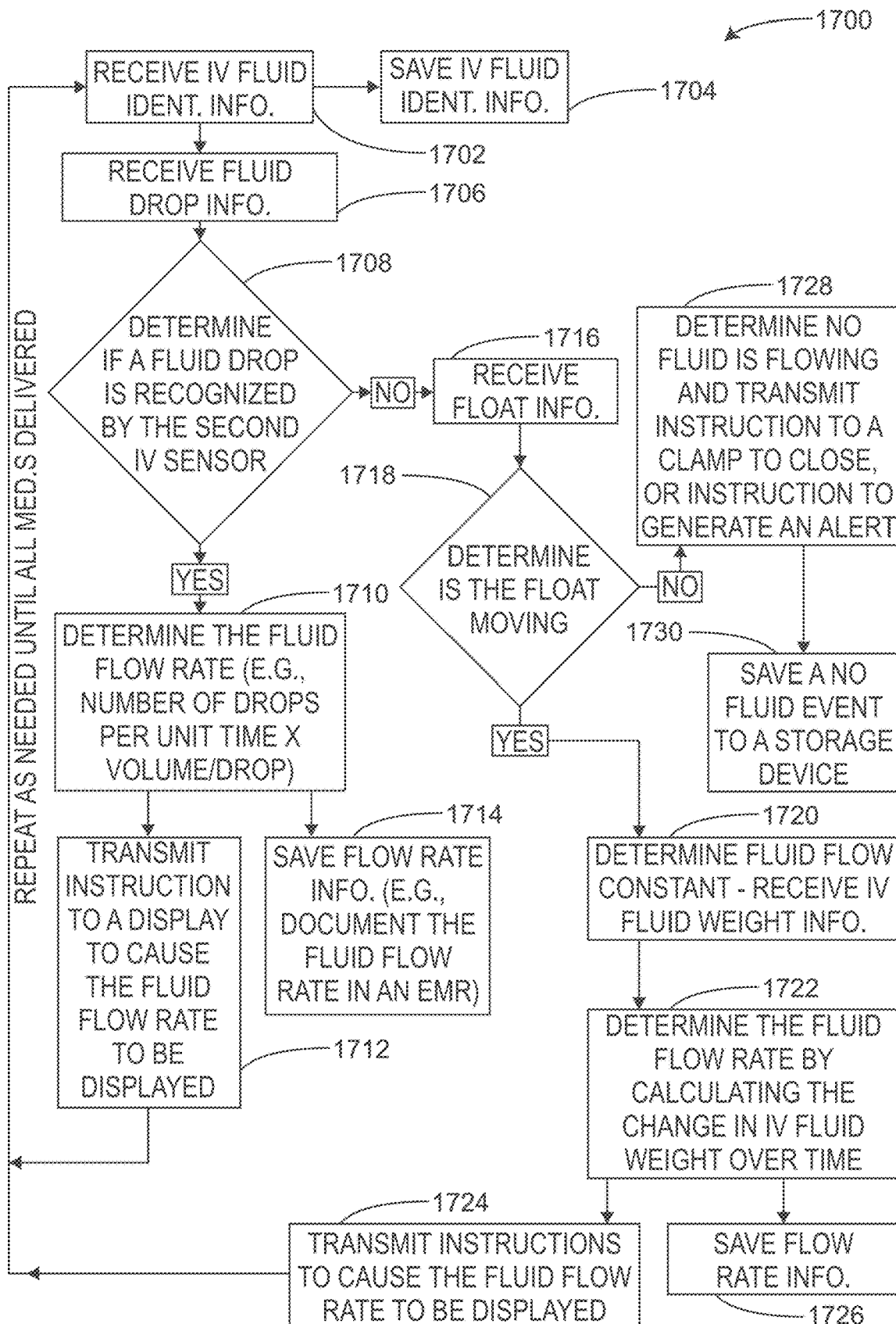
FIG. 17 is a second flow chart illustrating the technique of IV fluid identification and measurement, in accordance with at least one example of this disclosure.
Figure 18:
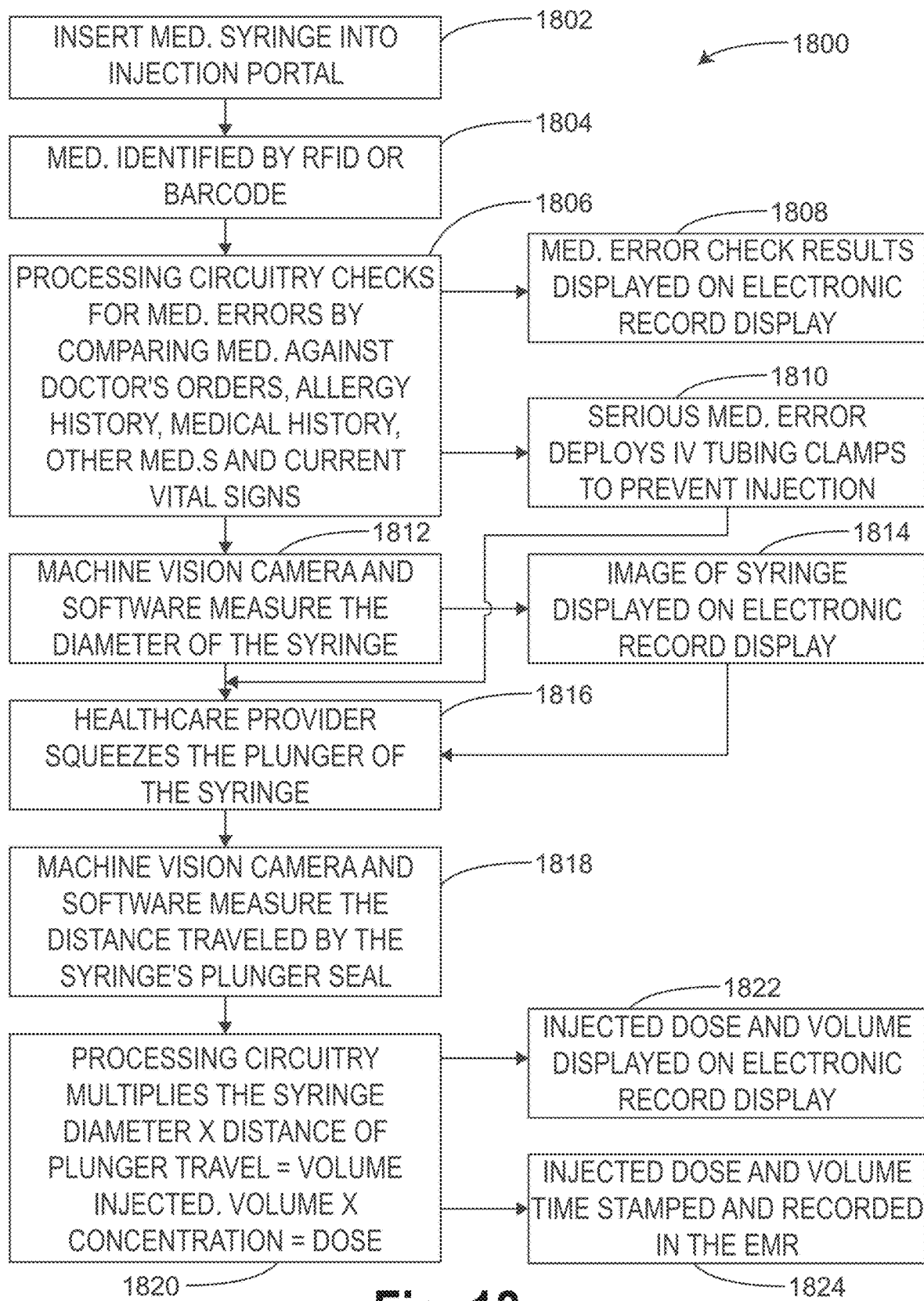
FIG. 18 is a flow chart illustrating a technique of medication identification and measurement, in accordance with at least one example of this disclosure.

FIGS. 16-18 show flow charts illustrating techniques for identification, measurement, monitoring, security and safety related to medications and/or IV fluids. The methods may be used with the systems, sub-systems and modules of FIGS. 1-15 (e.g., 101, 201, 1500), but may also be used with other systems. Likewise, the systems, subsystems of modules of FIGS. 1-15 may also be used with other methods. The techniques 1600, 1700, 1800, 1900, 2000, 2100, 2300 can be performed by at least one non-transitory machine-readable medium (e.g., computer readable) including instructions for operation of the systems described herein. Some steps of techniques may be performed by a provider. The systems can include processing circuitry (e.g., 157, 257, 1500, including one or more processors, processing circuitry hardware) for executing the instructions. The instructions, when executed by the processing circuitry can cause the processing circuitry to perform operations described in FIGS. 16-21 and 23, and as described in the examples throughout this disclosure.

FIG. 16 is a flow chart illustrating an example technique 1600 of IV fluid identification and measurement. To start the technique, in operation 1602 a provider hangs an IV fluid bag and attached drip chamber on electronic scale hooks in an IV fluid identification and measurement unit (e.g., FIG. 14). In operation 1604, a machine vision camera and software can identify the fluid and bag by the barcode label on the IV fluid bag. In operation 1606, the machine vision camera and software can identify the individual drops in the drip chamber and measure the size of the drop to determine the fluid volume per drop and count the number of drops per unit time. In operation 1608 the machine vision camera and software can calculate the flow rate by multiplying the number of drops per unit time by the volume/drop. In operation 1610, the fluid flow rate is displayed and document in the EMR.

In operation 1612, if the machine vision camera and software fails to identify individual drops in the drip chamber, in operation 1614 the machine vision camera and software can look for a floating ball (e.g., float) that is located in the drip chamber to determine if the ball is floating and if the ball is moving. In operation 1616, when the ball is not floating and/or moving, IV clamps are closed and the provider can change the empty IV bag if necessary. In operation 1618, if the machine vision camera and software can determine that the ball is floating and moving, the system determines that the fluid flow is so fast that the fluid flow is constant or continuous such that individual drops cannot be measured. In operation 1618, because individual drops cannot be determined, the system switches to measuring the fluid flow rate using an electronic IV scale (FIG. 14) to determine the fluid flow rate. In operation 1620, the fluid flow rate can be determined by monitoring the change in IV bag weight per time. In operation 1622, the fluid flow rate can be displayed and documented in the EMR.

FIG. 17 is a second flow chart illustrating a technique 1700 including aspects of the technique 1600 of IV fluid identification and measurement from the perspective of processing circuitry (e.g., 257, FIG. 2; 1502, FIG. 15). The technique 1700 may include an operation 1702 to receive IV fluid identification information from a first IV sensor (e.g., one or more sensors), such as an RFID or barcode reader to identify the fluid or other characteristics of an IV fluid bag as described herein. Operation 1704 can include saving the IV identification information to a storage device (e.g., one or more storage devices, memory, EMR). Operation 1706 can include to receive fluid drop information from a second IV sensor, such as a machine vision camera that detects, senses and measures an individual drop in a drip chamber to determine a fluid volume per drop and measure the number of drops per unit of time. While the illustrative example of FIG. 17 includes the first IV sensor and the second IV sensor, in some examples the first IV sensor and the second IV sensor can be the same sensor or same one or more sensors. Operation 1708 can include to determine if a fluid drop was recognized by the second IV sensor. If in operation 1708 it is determined that a fluid drop was recognized, operation 1710 can include determining a fluid flow rate, such as by calculating the flow rate by multiplying the number of drops per unit time by the volume per drop. In some examples, the volume per drop is measured, while in other examples, the volume per drop may be input by a user, or can be a value retrieved from a memory. Operation 1712 can include transmitting instructions to a display to cause a fluid flow rate to be displayed. Operation 1714 can include saving flow rate information to the storage device to document the fluid flow rate in the EMR. Any time a change is input or detected in the system, updated flow rate information can be displayed and saved.

If in operation 1708 it is determined that a fluid drop was not recognized, operation 1616 can include receiving float information from the second IV sensor or another IV sensor. The float information can include information about a float in the drip chamber including is the float still (e.g., not moving), moving, or is movement of the float slowing down. Operation 1718 can include determining if the float is moving. If the float is moving, Operation 1720 can include determining the fluid flow is constant. In such a scenario, the fluid is flowing but the fluid is flowing so quickly that individual drops of fluid cannot be distinguished because the fluid is flowing as a steady stream. Operation 1720 can further include determining the fluid flow rate by receiving IV bag physical characteristic information from a physical characteristic sensor, such as a weight sensor. The physical characteristic information can include weight information from the weight sensor (e.g., scale). Operation 1722 can include determining the fluid flow rate by calculating the change in IV bag weight over a period of time. In other examples, instead of weight information, the physical characteristic information can include a position of the IV bag that changes as a result of a change in weight, without the physical characteristic data corresponding directly to a weight measurement. Other physical characteristics and other physical characteristic sensors configured to monitor IV fluid delivery may be provided such that an automated, or at least partially automated EMR system is enabled.

If in operation 1718 it is determined that the float is not moving, operation 1728 can include determining that no fluid is flowing from the IV bag and transmitting one or more of: an instruction an actuator such as a clamp, to cause the actuator to inhibit fluid flow to the patient (e.g., close the clamp onto IV tubing to prevent flow); and transmit and instruction to an indicator (e.g., display, audible, tactile indicator) to cause an alert to be generated. Operation 1730 can include saving a no fluid event to the storage device.

FIG. 18 is a flow chart illustrating an example technique 1800 of medication identification and measurement. In operation 1802 a provider inserts a medication syringe into an injection portal (e.g., 411, FIG. 4). In operation 1804 the medication can be identified by a sensor such as by at least one of the RFID, barcode or QR sensors described herein. In operation 1806 processing circuitry checks for medication errors by comparing the medication against one or more of: a doctor's orders, allergy history, medical history, other medications and current vital signs. In operation 1808, the results of the medication error check can be displayed on an electronic record display. The results can indicate no error, the presence of an error, specific details about the error, or present a link to access information including additional details about the error. In operation 1810, if a serious medication error is recognized, the error deploys (e.g., causes actuation of) IV tubing clamps (e.g., 1060A, 1060B of FIG. 10) to prevent injection of the medication.

If in operation 1812, such as when no errors are determined, the machine vision camera and software can measure the diameter of the syringe. In operation 1814, an image of, or representation of the image of the syringe, is displayed on the electronic record display. In operation 1816 the provider squeezes the plunger of the syringe. In operation 1818, the machine vision camera and software measure the distance traveled by the syringe's plunger seal (e.g., 548, FIG. 5). In operation 1820 the processing circuitry calculates the volume injected by multiplying the syringe diameter times the distance of plunger travel. The processing circuitry can also calculate the dose by multiplying the volume injected by the concentration of the medication. In operation 1822 the injected dose and volume are displayed on the electronic record display. In operation 1824 the injected dose and volume are time stamped and recorded in the electronic medical record.

Figure 19:
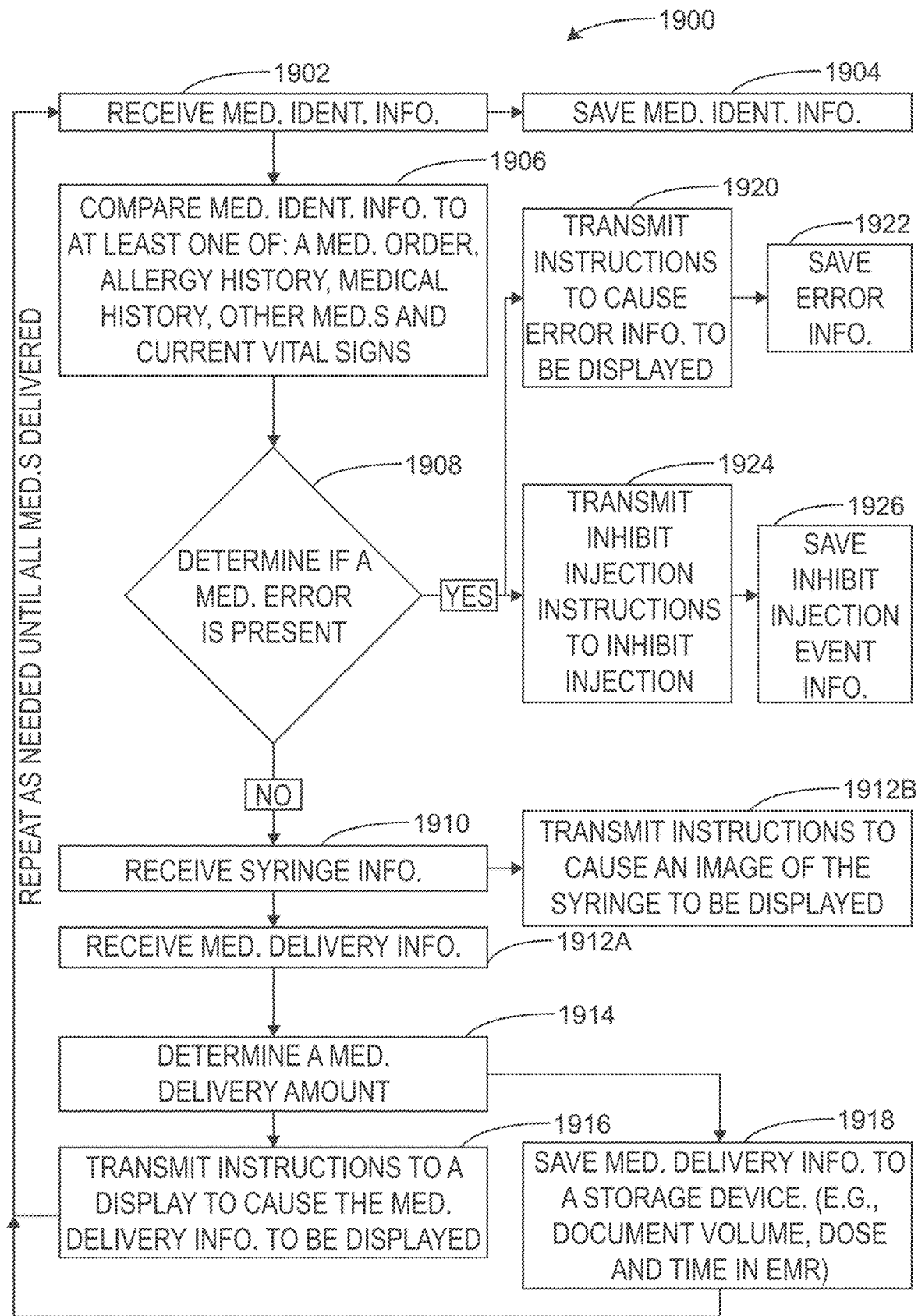
FIG. 19 is a second flow chart illustrating a technique of medication identification and measurement, in accordance with at least one example of this disclosure.

FIG. 19 is a second flow chart illustrating a technique 1900 including aspects of the technique 1800 of medication identification and measurement from the perspective of processing circuitry (e.g., 157, FIG. 1; 257, FIG. 2; 1502, FIG. 15).

Technique 1900 can include an operation 1902 to receive medication identification information such as medication type, concentration, brand, lot number or amount, from a first medication sensor (e.g., RFID, barcode or QR reader). Operation 1904 can include saving medication identification information to a storage device (e.g., one or more storage devices, memory). Operation 1906 can include comparing medication identification information to at least one of a medication order, allergy history, medical history, other medications ordered for the patient, and vital signs (e.g., previously obtained vital signs or current vital signs of the patient via continuous monitoring). Operation 1908 can include determining if a medication error is present. Operation 1910 can include receiving syringe information from a second medication sensor (e.g., a sensor configured to measure diameter, such as a machine vision camera). Operation 1912A can include receiving medication delivery information from the second medication sensor or another medication sensor. In some examples, the medication delivery information can include a distance of a syringe plunger travel.

Operation 1912B can include transmitting instructions to a display to cause an image of the syringe (e.g., actual image or representation of the syringe) to be displayed. A representation of the syringe can include an image communicating information about the syringe that is not an image of the actual syringe or can be a modified image of the syringe, such as to highlight or point out aspects of the syringe or medication within the syringe Using the medication delivery information obtained in operation 1912A, operation 1914 can include determining a medication delivery amount. Operation 1916 can include transmitting instructions to a display (e.g., display 226, FIG. 2) to cause the medication delivery information or medication delivery amount to be displayed.

If in operation 1908 it is determined that a medication error is present, operation 1920 can include transmitting instructions including error information to the display or another display to cause the error information to be displayed. In some examples, any of the instructions described herein that are sent to the display can be sent to one or more displays. Such displays can be located locally or remotely (e.g., in a different part of a room, in a separate room, in another building, in another state, in another country), to alert multiple providers. For example, a provider such as a nurse anesthetist located adjacent to the patient can be alerted to and provided with the information via display 226. In addition, a second provider, such as an anesthesiologist supporting the nurse anesthetist, and who may be supporting other nurse anesthetists working in different rooms, can also be alerted on a display of a mobile device, which may prompt them to check in with and potentially assist the nurse anesthetist. This concept can be applied outside the operating room to manage medication delivered by providers working in different rooms of a hospital or other care center, while a second provider such as a nurse manager, nurse practitioner, pharmacist or doctor oversees the work of the first provider. In operation 1922 the error information can be saved to one or more storage devices (e.g., 259, FIG. 2; 1516, FIG. 15).

Also in response to determining that a medication error has occurred in operation 1908, operation 1924 can include transmitting instructions to an actuator such as an IV tubing clamp to inhibit (e.g., prevent, reduce, limit) injection. In some examples, the actuator can reduce or limit the amount of the injection to a specified amount rather than completely inhibiting or preventing administration of the medication. Operation 1926 can include saving an inhibit injection event information to a storage device, such as any of the one or more storage devices (e.g., 259, FIG. 2; 1516, FIG. 15). The inhibit injection event information can include information such as the time of the event and the action taken to inhibit injection and how much the injection was inhibited (e.g., partially inhibited, completely inhibited, or amount of medication inhibited from injection).

If in operation 1908 it is determined that a medication error has not occurred, operation 1910 can include receiving syringe information including a syringe diameter from a sensor such as a machine vision camera. In some examples, the sensor can be the first medication sensor or can be a second medication sensor. Operation 1912A can include receiving medication delivery information from a sensor such as from the first medication sensor, the second medication sensor or another sensor. The medication delivery information can include a distance of plunger travel relative to a syringe body. Operation 1912B can include transmitting instructions to one or more displays such as, display 226, FIG. 2, to cause an image of the syringe or representation of the syringe to be displayed.

Operation 1914 can include determining a medication delivery amount, such as a volume or dose injected. For example, the volume injected can be calculated by multiplying the syringe diameter by the distance of plunger travel. The dose injected can be calculated by multiplying the volume injected by the concentration of the medication.

Operation 1916 can include transmitting instructions to the one or more displays to cause the medication delivery information to be displayed. Operation 1918 can include saving medication delivery information to the storage device (e.g., EMR). In some examples, the medication delivery information can include, but is not limited to, volume, dose, time of the injection, or time period of the injection.

Figure 20:
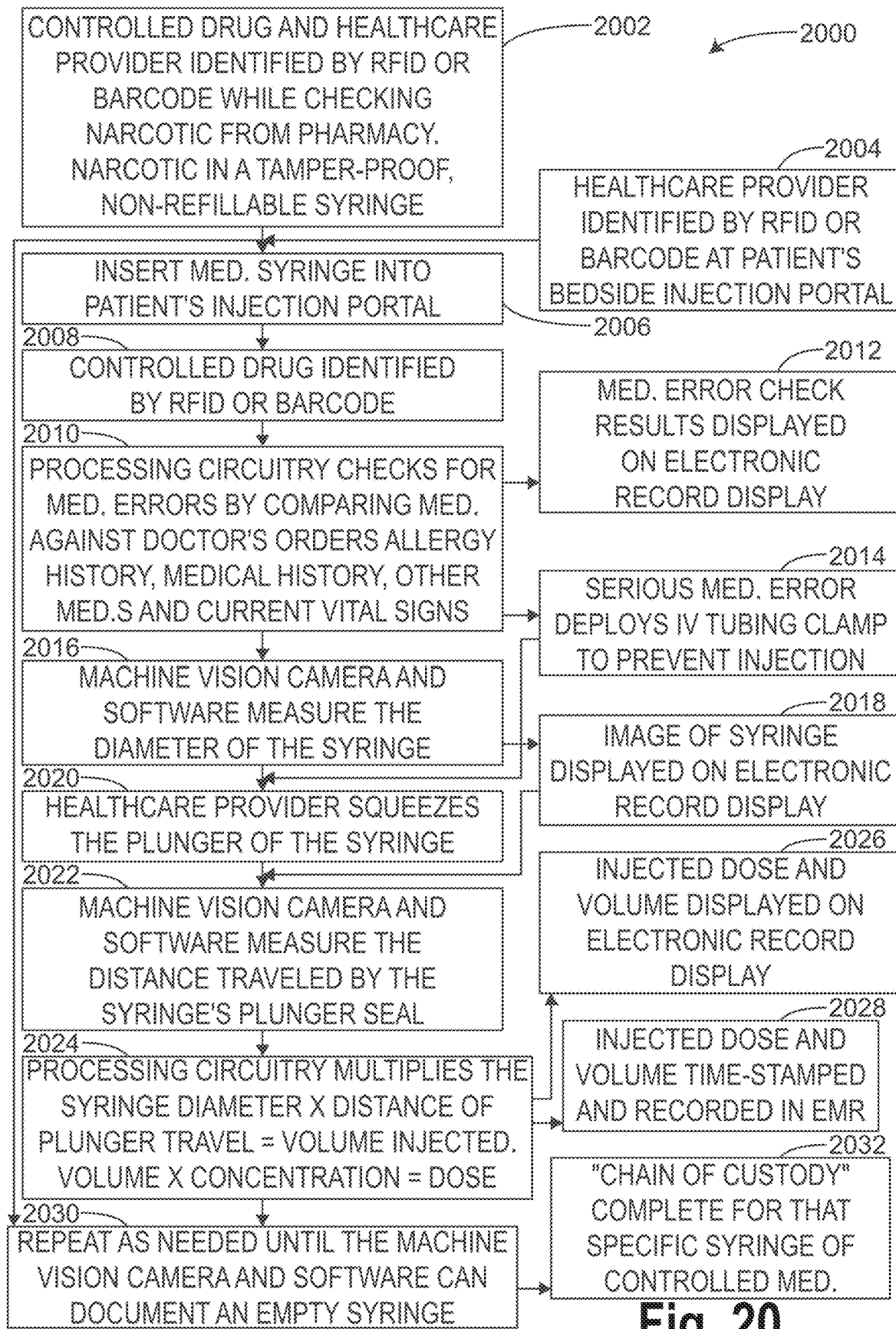
FIG. 20 is a flow chart illustrating a second technique of IV fluid identification and measurement including safety and security aspects, in accordance with at least one example of this disclosure.

FIG. 20 is a flow chart illustrating an example of a second technique of IV fluid identification and measurement including safety and security measures. Aspects of technique 2000 can be similar or the same as techniques 1800 and 1900, however, technique 2000 is particularly well-suited to the challenges of maintaining safety and security with controlled drugs such as narcotics. Technique 2000 can include operation 2002 of identifying a medication (e.g., a controlled drug) and identifying a health care provider, such as by RFID, barcode or QR code reader, retinal scanner, facial recognition, or fingerprint. Operation 2002 can occur at the time a provider checks out a drug from a pharmacy or a medication dispensing machine. The medication can include a narcotic in a tamper-proof, non-refillable syringe.

Operation 2004 can include identifying a provider such as by RFID, barcode or QR code reader, retinal scanner, facial recognition, or fingerprint at a patient's bedside, such as at an injection portal (e.g., 411, FIG. 4). The provider can be the same or a different provider as the provider in operation 2002. In operation 2006, the provider inserts the medication syringe into the patient's injection portal. In operation 2008, the controlled drug is identified, such as by an RFID, barcode or QR code reader associated with the injection portal. Operation 2010 can include processing circuitry checking for medication errors by comparing the medication against doctor's orders, allergy history, medical history, other medications and vital signs. Operation 2012 can include displaying medication error check results on a display, such as display 226, FIG. 2. If the medication error is of a serious nature, the error can cause IV tubing clamps to prevent injection. Operation 2016 can include machine vision camera and software measuring the diameter of the syringe. Operation 2018 can include an image, or an image representing the syringe being displayed on a display, such as display 226, FIG. 2. Operation 2020 can include a provider squeezing the plunger of the syringe. Operation 2022 can include the machine vision camera and software measuring the distance traveled by the syringe's plunger seal (e.g., 548, FIG. 5). Operation 2024 can include processing circuitry determining the volume of medication injected by multiplying the syringe diameter by the distance of plunger travel or determining the dose of medication injected by multiplying the volume of medication injected by the concentration of the medication. Operation 2026 can include displaying the injected volume or dose on a display, such as display 226, FIG. 2.

Operation 2028 can include saving the injected volume or dose along with a timestamp to the EMR. Operation 2030 includes repeating the operations of technique 2000 as necessary until the machine vision camera and software documents an empty syringe. Operation 2032 includes completing the "chain of custody" for a specific syringe of controlled medication. The operations of technique 2000 can be repeated as necessary for other syringes, thereby completing the "chain of custody" for each syringe.

Figure 21:
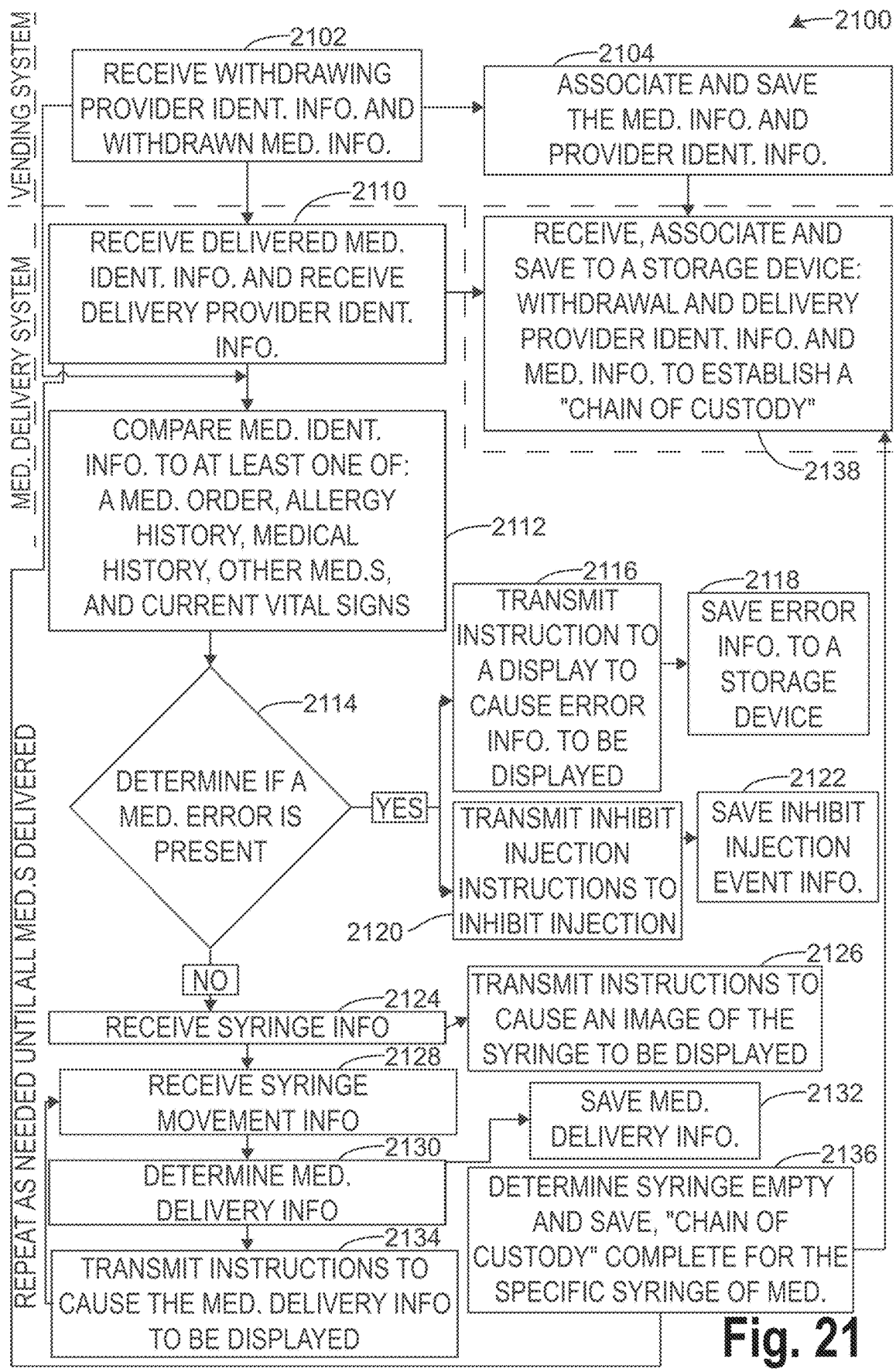
FIG. 21 is a second flow chart illustrating a second technique of IV fluid identification and measurement including safety and security aspects, in accordance with at least one example of this disclosure.
Figure 22:
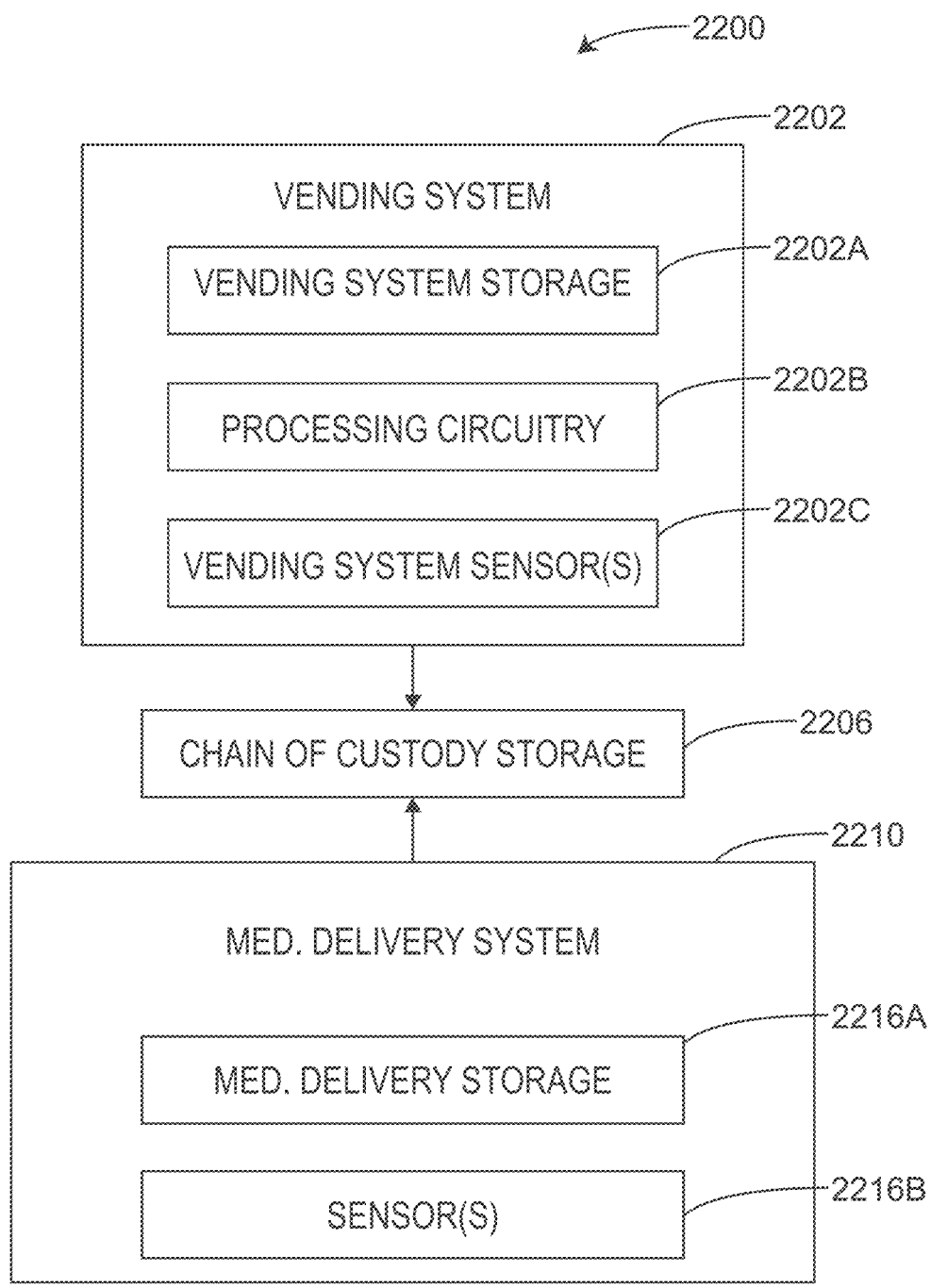
FIG. 22 illustrates generally an example of a block diagram of vending system and a medication delivery system of FIGS. 1-21 upon which any one or more of the techniques (e.g., methodologies) discussed herein may perform in accordance with at least one example of this disclosure.

FIG. 21 is a second flow chart illustrating a technique 2100 including aspects of the technique 2000 of IV fluid identification and measurement including safety and security measures from the perspective of processing circuitry, such as, but not limited to, processing circuitry 157, FIG. 1; 257, FIG. 2; 1502, FIG. 15. The technique may involve processing circuitry 2202B, such as may be part of a medication vending system as shown in FIG. 22. FIG. 22 illustrates generally an example of a block diagram of vending system and a medication delivery system of FIGS. 1-21 and 23 upon which any one or more of the techniques (e.g., methodologies) discussed herein may perform in accordance with some embodiments. FIGS. 21 and 22 are described together.

In some examples, operations 2102 and 2104 can be part of a vending system (2202, FIG. 22) for managing medication withdrawal from a pharmacy or other vending system. Operations 2110-2136 can be part of a medication delivery system (e.g., can be used with the bedside patient systems and modules shown and describe in FIGS. 1-15; medication delivery system 2210, FIG. 22). Operation 2138 can tie information, including data generated by the vending system 2202 and the medication delivery system 2210 together to facilitate tracking a "chain of custody" for a specific syringe of controlled medication from the pharmacy until the medication is completely injected into the patient. Chain of custody information can be stored to one or more of: the vending system storage 2202A, the medication delivery storage 2216, and chain of custody storage device (e.g., 2206, FIG. 22) and the EMR. Any of the storage described herein can include one or more storage devices or memory as described herein and can include other storage devices in electrical communication with the vending system or the medication delivery system.

Operation 2102 of the vending system can include receiving withdrawing provider identification information from a medication dispensing sensor 2202C, such as a first RFID or barcode reader that reads a badge of a provider and reads the medication identification information from a syringe or other medication container, or any other type of suitable sensor described herein. Operation 2104 can include associating and saving the medication identification information and the withdrawing provider identification information to a vending system storage device (e.g., 2202A, FIG. 22).

Operation 2110 can include receiving medication identification information from a first identification sensor (e.g., RFID, QR, barcode reader, or machine vision camera reads information about a medication) and receiving delivery provider identification information from the first identification sensor or another identification sensor (e.g., a second identification sensor, another RFID, QR or barcode reader, machine vision camera, retinal scanner, facial recognition sensor or fingerprint reader). In some examples, patient identification information can also be obtained from one of the first identification sensor, second identification sensor or another identification sensor, such as by scanning patient identification information on a hospital wristband. In some examples receiving the medication identification, the provider identification information or the patient identification can cause the processing circuitry to send an instruction to a display to prompt the user for the other of the medication identification information, the provider identification information or the patient identification information.

Operation 2112 can include comparing the received identification information to one or more of: a medication order, allergy history, medical history, other medications and current vital signs. Operation 2114 can include determining if a medication error is present. If it is determined that a medication error is present, operation 2116 can include transmitting instructions including error information to a display to cause the error information to be displayed. Operation 2118 can include saving the error information to one or more storage devices. Further, if in operation 2114 it is determined that a medication error has occurred, operation 2120 can include transmitting inhibit injection instructions to an actuator such as, but not limited to, an IV tubing clamp (e.g., 1060A, 1060B; FIG. 10) to inhibit injection. Operation 2122 can include saving an inhibit injection event information to one or more storage devices.

Operation 2124 can include receiving syringe information from a second medication sensor (e.g., syringe diameter including syringe inner diameter, outer diameter, or wall thickness from a machine vision camera). Operation 2124 can include receiving syringe size information from a data storage device, the syringe size information provided by the syringe manufacturer that supplies the specific syringes used by the specific healthcare facility. Operation 2126 can include transmitting instructions to a display to cause an image of the syringe or a representation of the syringe to be displayed. Operation 2128 can include receiving syringe movement information from the second medication sensor or another sensor. Syringe movement information can include, for example, a distance of travel of the syringe plunger relative to the syringe barrel.

Operation 2130 can include determining medication delivery information based on the syringe movement information. Medication delivery information can include, for example, a volume or dose of medication delivered to the patient (e.g., ejected from the syringe). In some examples, the volume of medication delivered (e.g., ejected from the syringe) can be calculated by multiplying the syringe inner diameter by the distance of plunger travel. Likewise, the dose of medication delivered can be calculated by multiplying the calculated volume by a concentration of the medication. Operation 2132 can include saving medication delivery information to one or more storage devices. In other words, operation 2132 can include documenting volume, dose and time in an EMR, in some cases automatically without intervention from a provider.

Operation 2134 can include transmitting instructions to one or more displays described herein to cause the medication delivery information to be displayed. Operation 2136 can include determining that a syringe is empty and saving "chain of custody" complete for the specific syringe of medication (e.g., controlled drug) to one or more storage devices.

To complete and document the chain of custody, thereby ensuring the medication was delivered to the patient, operation 2138 can include one or more of receiving, associating and saving to one or more chain of custody storage devices (e.g., 2206, FIG. 22), information from both the pharmacy vending system 2202 (FIG. 22) and the bedside medication delivery system 2210 (FIG. 22) (e.g., 1516; FIG. 15). In some examples the one or more chain of custody storage devices is not necessarily separate from the vending system storage 2202A or the medication delivery storage 2216, but rather can reside with one or the other systems, a different system, multiple systems or can be included as a single storage device.

Figure 23:
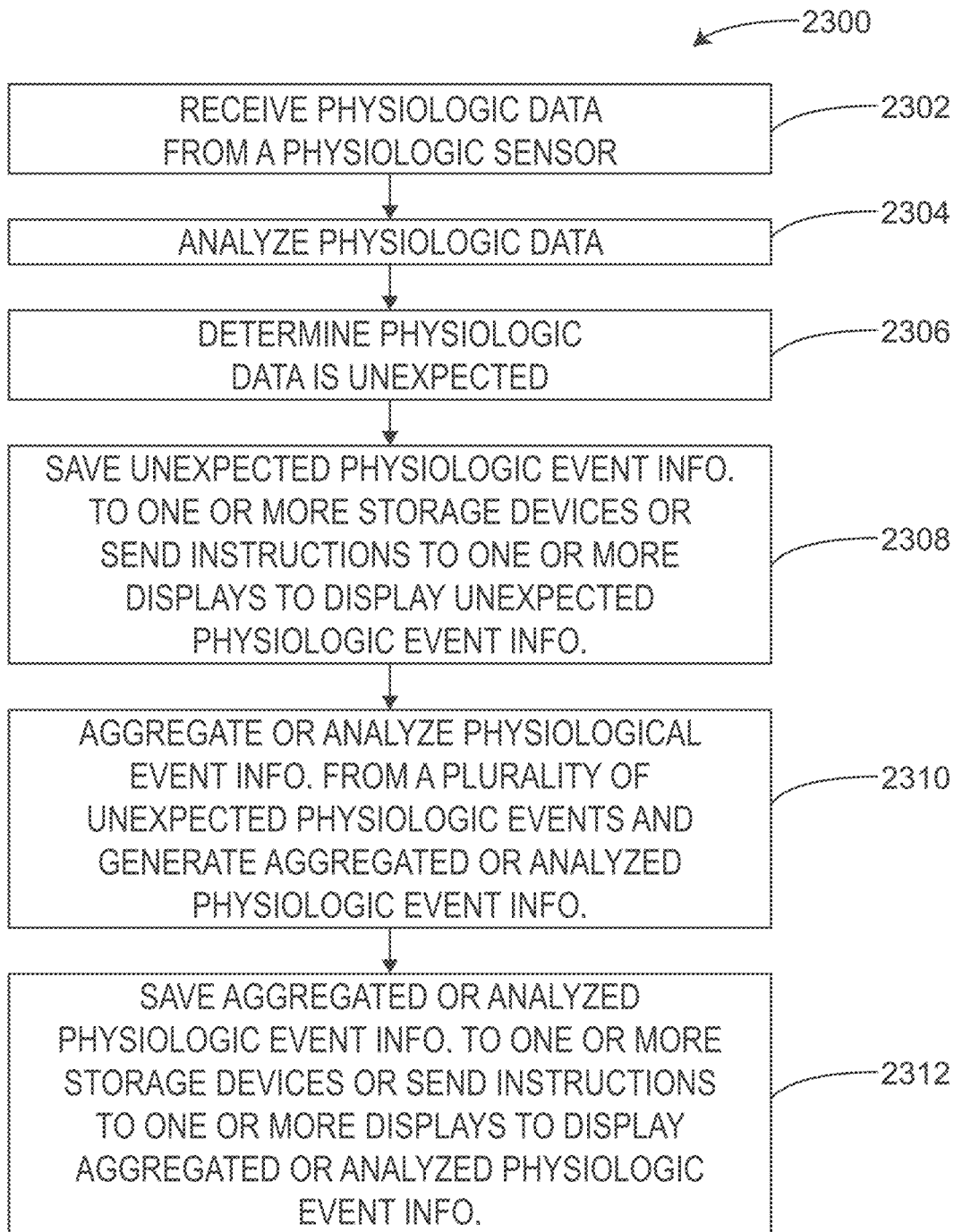
FIG. 23 is a flow chart illustrating a technique 2300 for assessing physiologic events, in accordance with at least one example of this disclosure.

FIG. 23 illustrates and example technique 2300 for assessing physiological events. In some examples, the EMRs created by the automated data consolidation module 100, 200, 400, 600, 800 can provide the most accurate and temporally correlated information about the relationship between any injected medication and the resulting physiologic response. In some examples, this is uniquely accurate dose-response data can be used as a final check of the chain of custody for controlled medications or any medication. The processing circuitry 157, 257 may include or be in electrical communication with artificial intelligence (AI) and/or machine learning that can compare the measured physiologic response in the several minutes after a medication is injected, to the expected physiologic response for that dose of that medication. For example, if the injected medication was a narcotic, it would be expected that the heart rate and blood pressure of the patient would decrease quickly after the injection.

In some examples, if the expected physiologic response does not occur, the AI software of the automated data consolidation module 100, 200, 400, 600, 800 may electronically "flag" that injection as suspicious. For example, if there is no physiologic response after injecting what was supposed to be a narcotic, it is possible that the drug had been stolen and replaced by saline. On the other hand, no response may simply mean that the patient is addicted to and tolerant of narcotics and that too is worth noting. An unpredicted response does not prove anything but multiple unpredicted responses in multiple patients can be suspicious. Therefore, aggregating or analyzing data over time for a particular patient or provider can alert management to issues. If any individual provider traverses a threshold number of flags (e.g., too many "flags") for unexpected physiologic responses (including no response), the automated data consolidation module 100, 200, 400, 600, 800 can generate an alert to notify management and an investigation of that provider may be warranted. Knowing that AI is "watching" the patients' response to a healthcare providers' injected medications, can be a significant deterrent to tempted drug thieves.

Technique 2300 can include determining if one or more unexpected physiological events has occurred, analyzing saving, aggregating and displaying such information, in any order. The method can be performed by processing circuitry 157, 257, 1502, including other processing circuitry, memories and databases in electrical communication with processing circuitry 157, 257, 1502 to one or more of: receive physiologic data, analyze physiologic data, determine physiologic data is unexpected, create and send instructions to cause an alert to the provider or another user, or save a physiological event information to a storage device 1516 which may include a database. The physiological event information can include, but not limited to data generated by the various sensors and equipment described herein, including one more of: physiological information, patient information, provider information, medication information, time information, location information, facility information, equipment information, aggregated physiological event information and analyzed physiologic event information.

Operation 2302 can include receiving physiologic data from a physiologic sensor, Operation 2304 can include analyzing the physiologic data. Operation 2304 can include comparing the physiologic data to expected physiologic responses. Based on the outcome of the analysis in operation 2304, in operation 2306, the processing circuitry can determine if the physiologic data is unexpected, and if so, operation 2308 can include saving unexpected physiologic event information to one or more storage devices, or can include sending instructions to one or more displays to display unexpected physiologic event information.

Operation 2310 can include aggregating or analyzing physiologic event information from a plurality of unexpected physiological events and generating aggregated or analyzed physiologic event information. In some examples, aggregating can include aggregating a number of physiological events by counting the number of physiological events for a given provider, patient, group of patients, medical facility, type of medication, or any other suitable assessment. Operation 2312 can include saving aggregated or analyzed physiologic event information to one or more storage devices or sending instructions to one or more displays to display aggregated or analyzed physiologic event information. In some examples, the physiologic event information can include any type of physiologic event that occurs, including expected or desirable physiologic events The operations of technique 2300 can help provide safer care for patients, including providing narcotic medications when helpful, while keeping a close eye on drug abuse by providers or patients. Taken at a high level, technique 2300 can help medical facilities evaluate which medications are most often abused by patients or stolen by providers, and to mitigate risk for insurers.

Errors can easily occur during the administration of oral medications. Administering oral medications and monitoring the administration of oral medications has always been challenging. Many pills look alike and are easy to confuse with similar pills. Even dissimilar pills are easily confused. Pills are easily miscounted. Finally, the patient may not take the pill and swallow it. Automating the documentation of oral medication administration may have several advantages including: reducing medication errors, alerting the caregiver to a medication error or allergy, verifying the pill count and verifying that the patient actually takes and swallows the pills.

In some examples, the pills may be delivered from the pharmacy to the ward, to long-term care, to home care or any other care location, in a bottle labeled with an RFID tag or barcode label. The RFID tag or barcode label may identify one or more of the patient, the medication, dosage, manufacturer, expiration date and other useful information.

In some examples, the monitoring of the administration of oral medications may be accomplished by a combination of RFID, barcode, video and machine vision combined with machine learning (ML) technologies. For example, a bottle of pills may be identified by a RFID tag or barcode label that can be read by a RFID or barcode reader that is in electrical communication with the processing circuitry and software of the module. In some examples, the processing circuitry and software of the module automatically checks the identified pill bottle against the doctor's orders to verify that they match.

Figure 27:
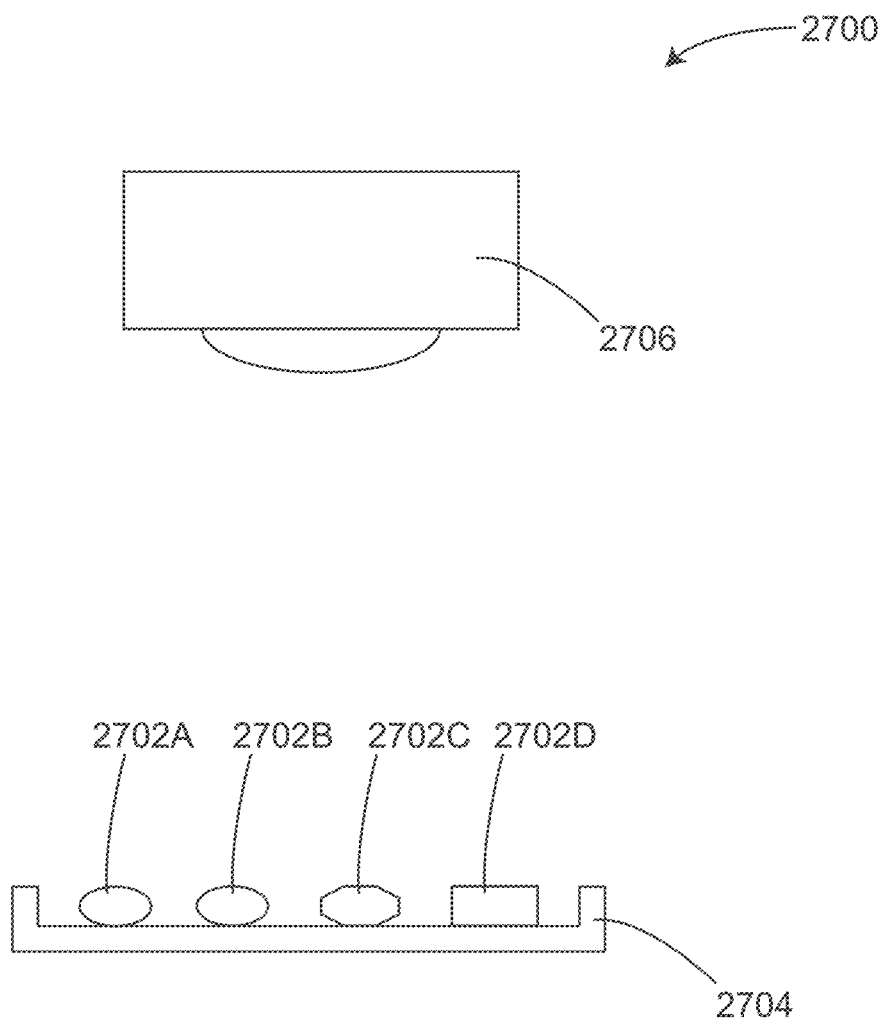
FIG. 27 illustrates a cross-sectional view of an example of machine vision counting of pills, in accordance with at least one example of this disclosure.

In some examples as shown in FIG. 27, the caregiver or a mechanical dispenser pours the prescribed number of pills 2702A-D from the bottle into a container or onto a small tray 2704 of a pill monitoring system 2700. In some examples, the pills 2702A-D are then "viewed" by a digital camera 2706 such as a video camera or machine vision camera and the image is sent to the processing circuitry and software of the module where it is compared with known images of the specific pills stored in an image library, using ML. The identity and quantity of the pills 2702A-D may be compared to the doctor's orders and the identity of the pills 2702A-D may be compared to the bottle of pills that was identified by a RFID tag or barcode label. In some examples, if RFID or barcodes are not used to identify the pill bottle, it may be advantageous for the machine vision image of the pill 2702A-D itself to be compared to known images of the pills prescribed by the doctor stored in an image library. In some examples, machine vision may be used to measure the size of the pill 2702A-D in order or help differentiate similar colored or shaped pills. In any event, verification of the number and identity of the pills to be given to the patient at that time, can be made and automatically recorded in the electronic record.

In some examples, the caregiver or patient manually indicates to the processing circuitry and software of the module, that the pills 2702A-D were taken by the patient. In some examples, the processing circuitry and software can then record the pills 2702A-D taken as a "dose event" including a time-stamp that allows temporal correlation with the patient's response to the medication.

In some examples, a video camera provides images of the patient taking the pills 2702A-D to the processing circuitry and software of the module. The processing circuitry and software may use ML to compare the video images to known images of patients taking pills stored in an image library, in order to automatically confirm that the pills were taken by the patient. In some examples, the processing circuitry and software then record the pills 2702A-D taken as a "dose event" including a time-stamp that allows temporal correlation with the patient's response to the medication.

In some examples, the video camera images may be used to document that the patient took their pills 2702A-D even in the absence of a healthcare provider being present, such as a patient at home. A surprisingly high percentage of patients are unreliable in taking their medications. This medication documentation system not only documents that the medications were taken but may also be programed to provide positive feedback to the patient to reinforce the good behavior. Alternatively, if the medications are not being taken as ordered by the healthcare provider, the medication documentation system may notify the healthcare provider so that they can intervene sooner.

Figure 28:
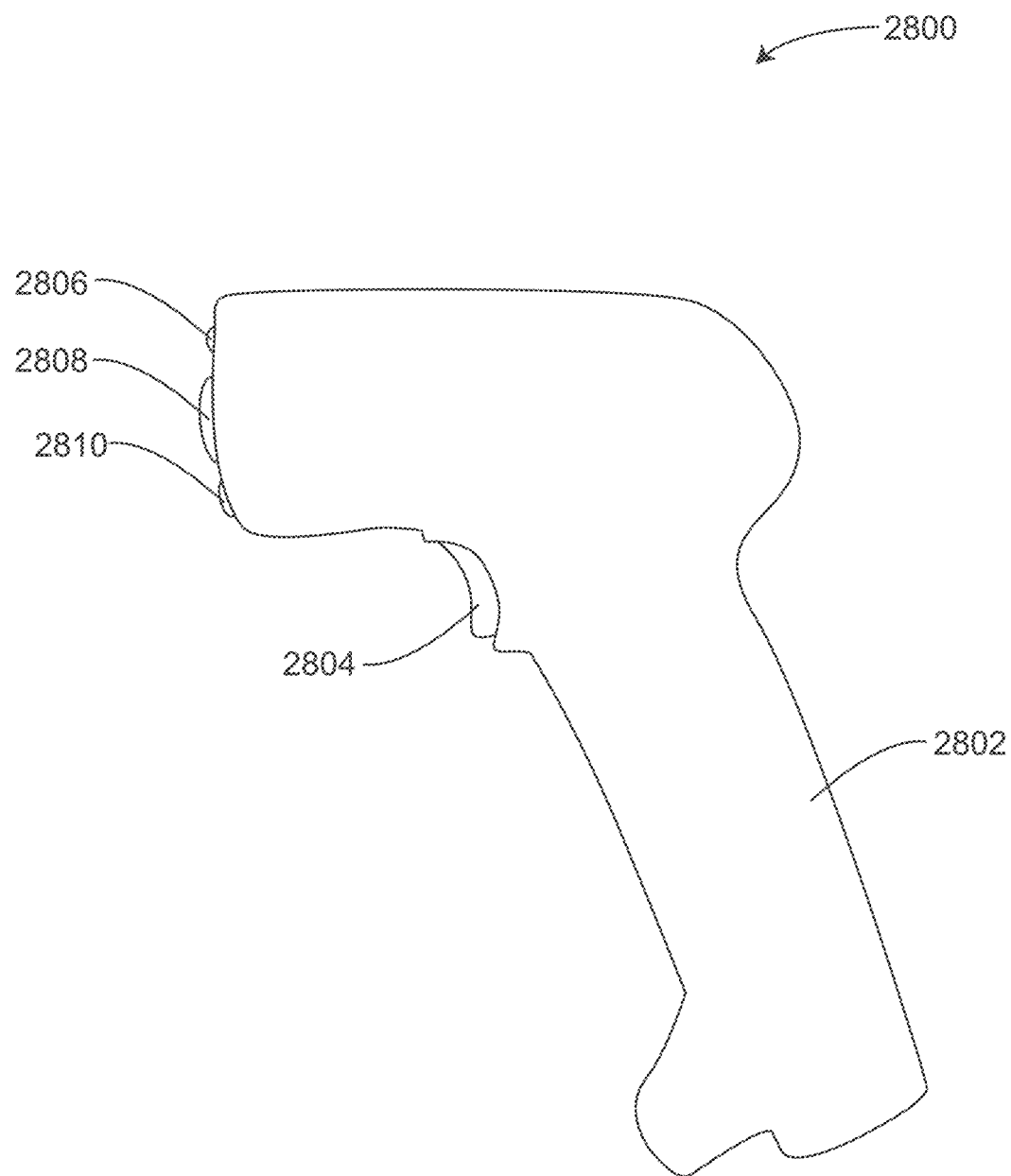
FIG. 28 illustrates a side view of an example of a portable digital camera, in accordance with at least one example of this disclosure.

In some examples, the module of this disclosure includes a system for documenting healthcare events and medical equipment operating settings, using machine vision or video with machine learning (ML) or artificial intelligence (AI) analysis. In some examples as shown in FIG. 28, a portable digital camera 2800 may be used to document the event or equipment settings. Digital cameras 2800 in this disclosure include but are not limited to: RGB digital cameras, black and white digital cameras, infrared digital cameras, video digital cameras and machine vision digital cameras. In some examples, the portable digital camera 2800 may be a handheld digital camera and may be conveniently mounted on a pistol-like handle 2802 and include a pistol-like trigger 2804 for activating the camera 2800. The pistol-grip handle may include a disposable cover to prevent contamination of the handle by the user's contaminated hands. In some examples, the digital camera 2800 produces digital images that may be sent to the processing circuitry in the module, where machine learning (ML) or artificial intelligence (AI) software can compare the images with known images stored in an image library. In some examples, the digital camera 2800 produces digital images that may be sent to the processing circuitry in the module, where machine vision software may measure the size of an object, the location of an object or the distance an object moves. In some examples, the digital camera 2800 produces digital images that may be sent to the processing circuitry in the module, where machine vision software may measure subtle changes in color, for example changes in skin color seen during changes in perfusion, oxygenation or remote plethysmography.

In some examples, the handheld digital camera may include a laser pointer 2806 that helps the user accurately aim the camera to standardize the scene and to most effectively capture an image of the item or device. The laser pointer 2806 may also be used to identify the subject item or device in a scene of multiple items or devices, to the processing circuitry and ML software. In some examples, a label with a printed target may be the designated target to aim the laser pointer 2806 at, standardize the scene so that the resulting digital photograph or image is oriented similarly to the comparative images in the ML image library. In one example, the preferred camera orientation may be straight at the target and approximately 2 feet away from the item or device. Other icons or shapes are anticipated for the target labels.

Figure 29:
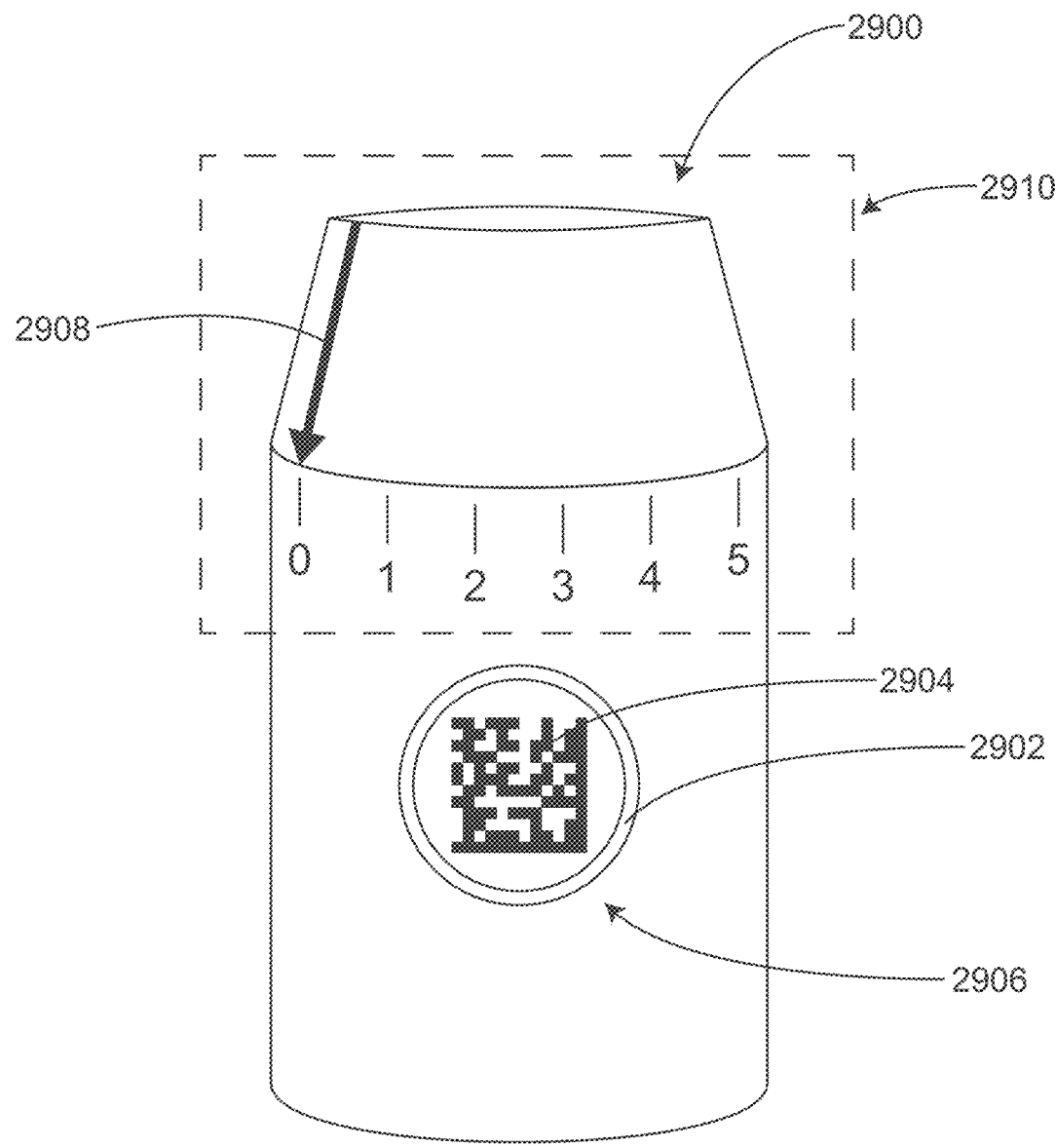
FIG. 29 illustrates a front view of an item or device to be recorded, in accordance with at least one example of this disclosure.

In some examples as shown in FIGS. 29 and 30, the item or device 2900 being photographed may be an anesthetic vaporizer and may have a label such as a target 2902 attached so that the laser pointer 2806 can be aimed at a specific location. Aiming the laser 2806 at a specific location on the item or device 2900 helps to standardize the scene so that images of the item or device 2900 are always taken from the same orientation—the straight-on view of the subject item or device for example. This eliminates the need for the image library to include images of the sideview, the back view, the top view or oblique angles, which would vastly complicate the ML identification of the item or device 2900. Consistently photographing the subject item or device 2900 from a consistent reference point such as straight on to the target 2902, standardizes the scene allowing the image library to be much smaller, eliminating the need for side view and top view images.

In some examples, if more than one item or device are in the photographed image, the laser pointer 2806 aimed at target 2902 standardizes the scene by identifying for the processing circuitry, the item or device that is to be documented.

In some examples, the laser pointer 2806 may be a diode laser or any other kind of laser. In some examples, the laser pointer may be a diode light or any other kind of light. In some examples, the laser pointer may be one color (red for example) while aiming the camera lens 2808 and switch to another color (green for example) when the digital photograph has been successfully taken. The laser pointer 2806 not only improves the quality of the captured image but makes the job of capturing the image more fun for the clinician. For example, in some examples, the indication of a successfully captured image may be a projected image such as the image of a paintball splattering against the target 2902 on the item or device 2900. Other projected images including but not limited to: arrows, darts, splattering cream pies, splattering eggs, splattering tomatoes or even bullet holes, are anticipated for making the capture of data more fun. Aiming the laser 2806 at a specific target 2902 on the item or device 2900 also helps to steady the camera 2800 before shooting the picture.

In some examples, the projected image of a splattering paintball for example may be from a portable liquid crystal display (LCD) projector 2810 that may use a light emitting diode (LED) as a light source, mounted in the pistol-like handheld digital camera holder 2800. Other types of projectors or even clusters of lasers are anticipated as alternative ways to project an image onto the item or device. In some examples, when the image of the item or device is successfully recorded by the digital camera, the LCD projector 2810 may instantly project a short video sequence of a paintball (or other object) splattering against the target 2902 on the item or device 2900 to give positive feedback to the clinician of a successful image acquisition.

In some examples, the system may also keep score of the number of "hits," the percentage of "hits," or the accuracy of the "hits," in order to make a game of data recording. Having fun recording healthcare data is the exact opposite of clinician's current attitude toward data recording. Manual data recording as it is currently done in healthcare is described as "hated work" and has been shown to cause "burnout," even leading to early retirement for some clinicians. In some examples, the point and shoot nature of the portable digital camera 2800 of this disclosure with instant positive feedback for a "hit," is designed to make data entry fun for clinicians.

In some examples as shown in FIG. 29, the item or device 2900 to be documented may include a label 2906 with a QR code 2904 attached to the item or device 2900. In this disclosure we refer to a QR code 2904, however it should be understood that other coding technologies including but not limited to: barcodes, symbols, icons or alpha numeric identification, are anticipated as acceptable replacements for QR codes 2904. In some examples, the label 2906 with a QR code 2904 may be the target or may be part of the target 2902 and is attached to the item or device 2900 in the scene to be photographed with the portable digital camera 2800. In some examples, the QR code 2904 may be inside the target 2902 previously disclosed and may be applied to a substantially central location on the item or device 2900 in order to standardize the scene. In some examples, the target 2902 with the QR code 2904 label 2906 may be applied to an area of the item or device 2900 that aims the camera 2800 so that the area of interest 2910 of the item or device 2900, such as a dial 2908 or indicator light for example, is captured in the image. In some examples, the area of interest 2910 for each item or device in the image library may be preidentified by the processing circuitry so that the ML software know where in the image to look for the key information.

In some examples, it may be preferable to print the target 2902 and QR code 2904 onto a non-reflective material so that the laser beam is not reflected back at the user or other staff. In some examples, the laser pointer 2806 may automatically turn off just before the digital image is taken so that the laser 2806 does not distract from reading the QR code 2904.

In some examples, the QR code 2904 can be read by the handheld digital camera 2800 and processing circuitry to identify the type of item, device or equipment, the manufacturer and model of the item, device or equipment as well as other information that may be useful. For example, as shown in FIG. 29, the QR code 2904 may indicate that the device is an Isoflurane anesthetic vaporizer made by Drager, Model XXX. By identifying the specific device with a QR code 2904, the ML software does not need to look through the entire image library to first identify the type of the item or device, then to identify the make and model of the item or device and then finally identify the desired information from the item or device.

Figure 30A:
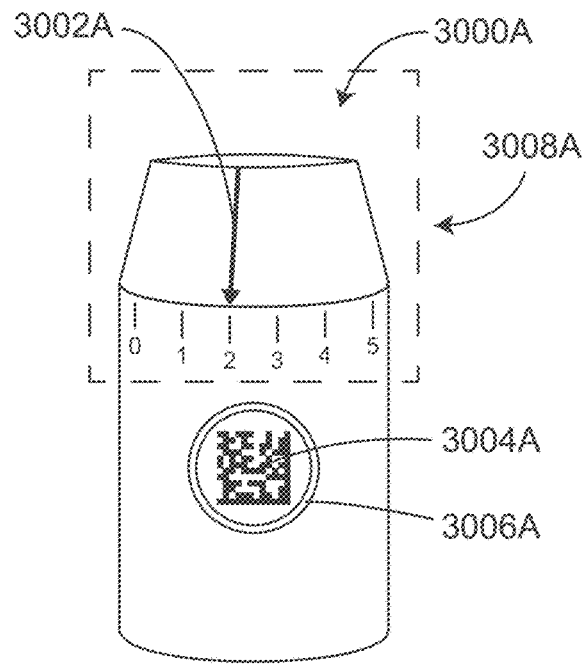
FIGS. 30A-D illustrates front views of items or devices to be recorded, in accordance with at least one example of this disclosure.
Figure 30B:
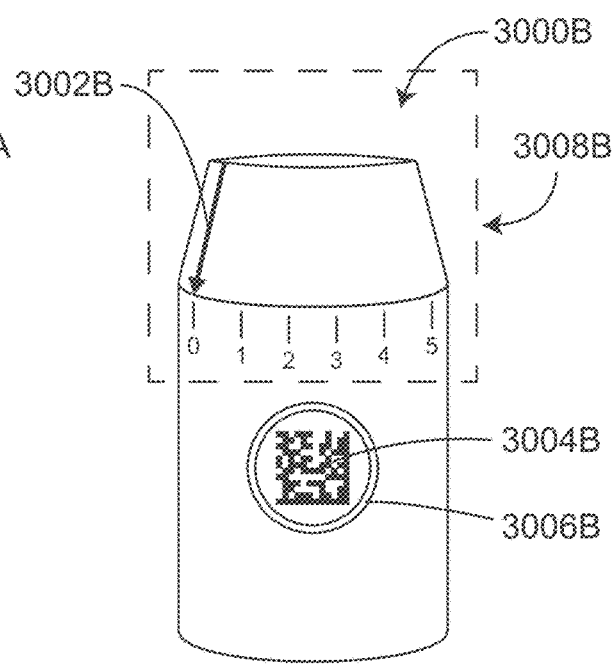
Figure 30C:
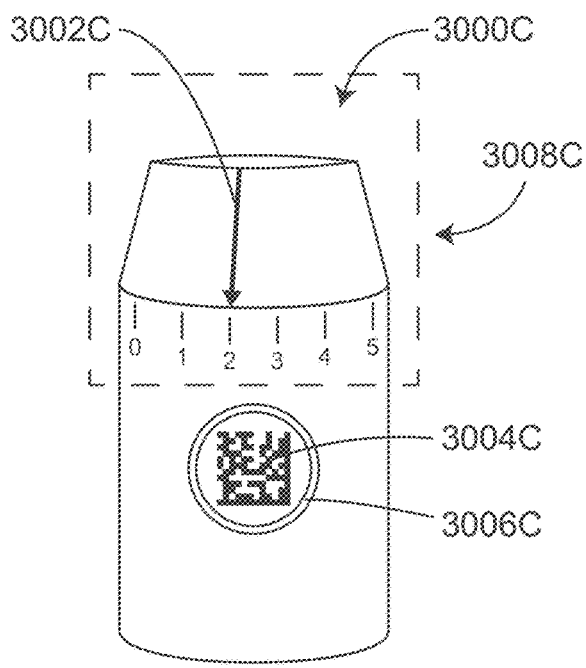
Figure 30D:
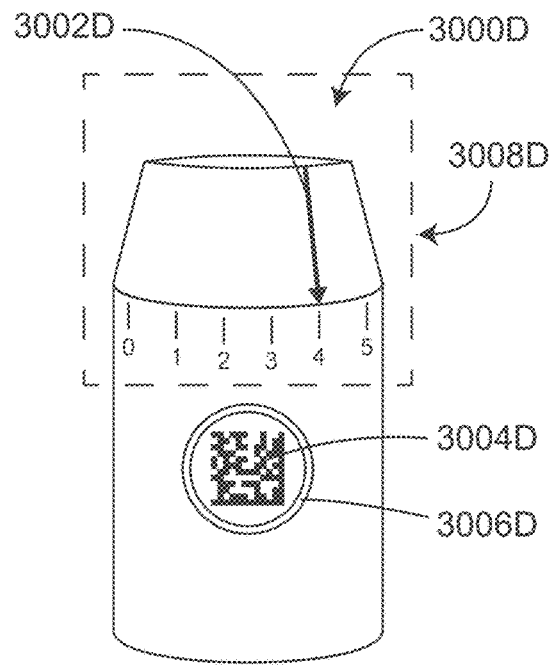

In some examples as shown in FIGS. 30A-D, the image of an anesthetic vaporizer 3000A taken by handheld digital camera 2800 is compared to images of similar anesthetic vaporizers 3000B-D stored in the image library. The QR code 3004A allows the software to instantly narrow the search to images of that specific device with different dial settings 3002B-D in order to determine the concentration of the Isoflurane coming from the vaporizer. In some examples, the scene may be further standardized by preprograming into the processing circuitry memory the part of the image containing the important information or area of interest for that specific item or device. In some examples, the processing circuitry may draw an imaginary box around the area of interest 3008A-D in the scene. In this example, the dial 3002 is the important portion of the scene and the machine learning comparison of images with images in the image library can focus on the part of the image in the box 3008A-D, the area of interest. In this example, the dial setting 3002A in the subject image as shown in FIG. 30A, matches best with the dial setting 3002C in the image in FIG. 30C and the ML software has been "taught" that the image in FIG. 30C corresponds with 2% isoflurane. When the image is successfully matched, "2% Isoflurane" is then automatically time-stamped by the processing circuitry and saved to the anesthetic record, the electronic medical record or other database as a dose event.

In some examples, with the make and model of the vaporizer 3000A identified by the QR code 3004A, the ML software only needs to review ~10 images while looking through anesthetic vaporizer images 3000B-D in the image library, in order to find a match that indicates that the dial is set at 2%. Tens of thousands of images would be necessary if the device 3000A was not identified by a QR code 3004A and the orientation of the device in the scene not prescribed by the laser pointer 2806 and target 3006A. The QR code 3004A read by the handheld digital camera 2800 identifying the specific device 3000A vastly narrows the ML image search, making the search for a match both faster and more reliable.

Figure 31:
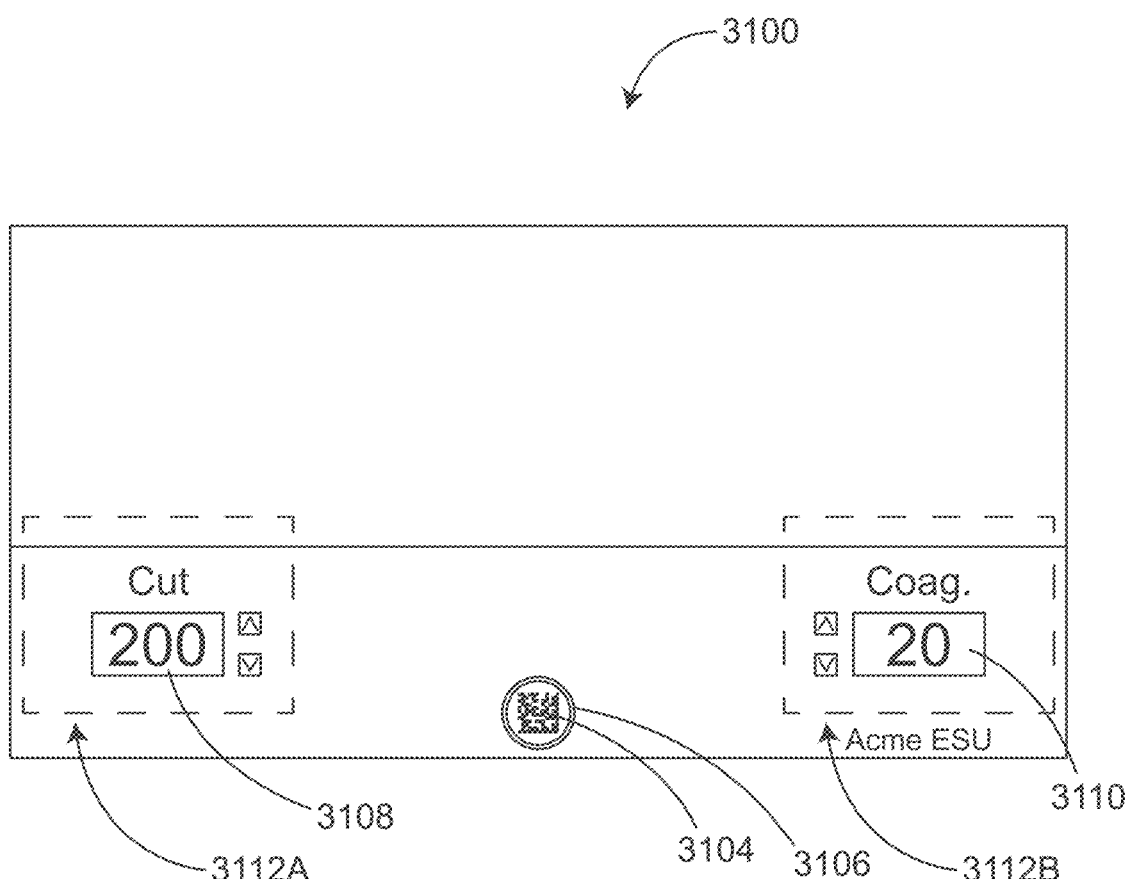
FIG. 31 illustrates a front view of an item or device to be recorded, in accordance with at least one example of this disclosure.

In some examples, the handheld digital camera 2800 with machine vision can be used to document the operating parameters of a piece of electronic or electromechanical equipment that does not produce a data output of its operating parameters. For example, the handheld digital camera 2800 with machine vision may be used to capture an image of the control panel of an electrosurgical unit (ESU) 3100 as shown in FIG. 31. In this example, a QR code 3104 may be used both as an aiming target 3106 and to identify the make and model of the specific piece of medical equipment. In some examples, the processing circuitry may draw an imaginary box around the areas of interest 3112AB in the scene. In this example, the germane information is the wattage of current in the cut 3108 and coagulation 3110 modes of operation, indicated by illuminated numbers on the control panel. The machine learning comparison of images with images in the image library can focus on the part of the image in the areas of interest 3112A,B boxes. In this example, the ML software needs to match these numbers 3108, 3110 with numbers in its image library to determine the power settings and then those values may be time-stamped by the processing circuitry and saved to the anesthetic record, the electronic medical record or other database as a dose event.

In some examples, "standardizing the scene" using a light pointer and coding system results in one or more of the following benefits: 1.) Steadies the camera. 2.) Identifies which item or device is the subject when more than one item or device may be in the image. 3.) Makes the front view orientation of the camera relative to the subject item or device reproducible, eliminating the need for side view, back view, top view or oblique view images of the item or device in the image library. 4.) Specifically identifies the type of item or device, make and model so that only images of that make and model are used for comparison and matching, vastly narrowing the search. 5.) Allows preprogramming of the processing circuitry to know where in the image the important information is located so that the machine learning function can focus on that area—the area of interest. In some examples, "standardizing the scene" as disclosed herein results in ML image matching that is much more reliable and faster.

Since the control of the ESU is typically done by the OR nurse, it may be advantageous to have two or more portable digital cameras 2800 with machine vision in the operating room. One camera may be used primarily by the anesthesia provider and the other camera by the OR nurse. The cameras may be in wired or wireless electronic communication with the processing circuitry and software of the automated data entry system.

In some examples, the handheld digital camera 2800 with machine vision can be used to document other aspects of the patient's care. For example, if it is desirable to document the placement of an IV in the patient's left hand, the handheld digital camera 2800 may be aimed at the IV in the patient's hand and an image acquired. In this example, the ML software first must identify that it is an IV and then identify a left hand. Since IV hubs are color coded corresponding with the size of the IV catheter, the ML software can also identify the size of the IV catheter.

In some examples, a short procedure note may be desirable or required. Since the processing circuitry and software of the system for documenting healthcare events is specifically designed to aid the healthcare provider, it needs to know who the provider is to optimize the assistance. Therefore, in some examples the provider may start their interaction with the system by identifying themselves with the RFID or QR code or barcode on their ID badge. Since healthcare providers tend to be "creatures of habit," they almost always use the exact same description of a given procedure when documenting that procedure, every time they do that procedure. If provider's preferred description of any given procedure has been "taught" to the processing circuitry and software and stored in the memory of the system, the system for documenting healthcare events of this disclosure can automatically enter that custom description of the procedure into the record and further automatically customize the description with "left hand" and "18 gauge" in this example.

In some examples, the handheld digital camera with machine vision can be used to document other aspects of the patient's care. For example, if it is desirable to document intubation of the trachea with an endotracheal tube, the handheld digital camera 2800 may be aimed at the patients face with a tube protruding from the mouth and an image acquired. In this example, the ML software first must identify that it is an endotracheal tube. In some examples, the size of the tube may be obtained from a QR code or barcode on the waste sterile wrap that may be placed in the field of the image. Alternately, the tube size and depth may be assumed based on the known preferences of the given clinician. For example, a given clinician may routinely intubate adult males with 8 mm endotracheal tubes taped at 21 cm at the teeth. The processing circuitry and software know that the patient is an adult male and automatically fills in the procedure note for the clinician. If there is an unlikely exception to the routine, the clinician can go into the record and manually correct the record for the exception.

Since healthcare providers tend to be "creatures of habit," they almost always use the exact same description of a given procedure when documenting that procedure, or other healthcare notes. In some examples, common procedure notes or common healthcare notes may be prerecorded by a clinician and the prerecorded note may be labeled with a QR code or barcode. In some examples, a list of these prerecorded notes may be consolidated on one or more cards or sheets of paper along with their corresponding QR code or barcode. In some examples, the handheld digital camera 2800 with machine vision can be used to scan the appropriate QR code or barcode which automatically causes the processing circuitry to record the chosen procedure note or healthcare note into the anesthetic record or EHR, saving the clinician considerable time.

In some examples, the handheld digital camera 2800 with machine vision can be used to document subtle color changes in the patient's skin. In this example, consistent illumination of the skin may be important and the handheld digital camera 2800 may include one or more illuminating lights shining at the scene to be photographed. The lights may be white, colored or of specific wavelengths, in order to highlight the desired observable parameter. For example, if remote plethysmography is the objective, illumination in the infrared and near-infrared spectrum may be desirable.

Figure 32:
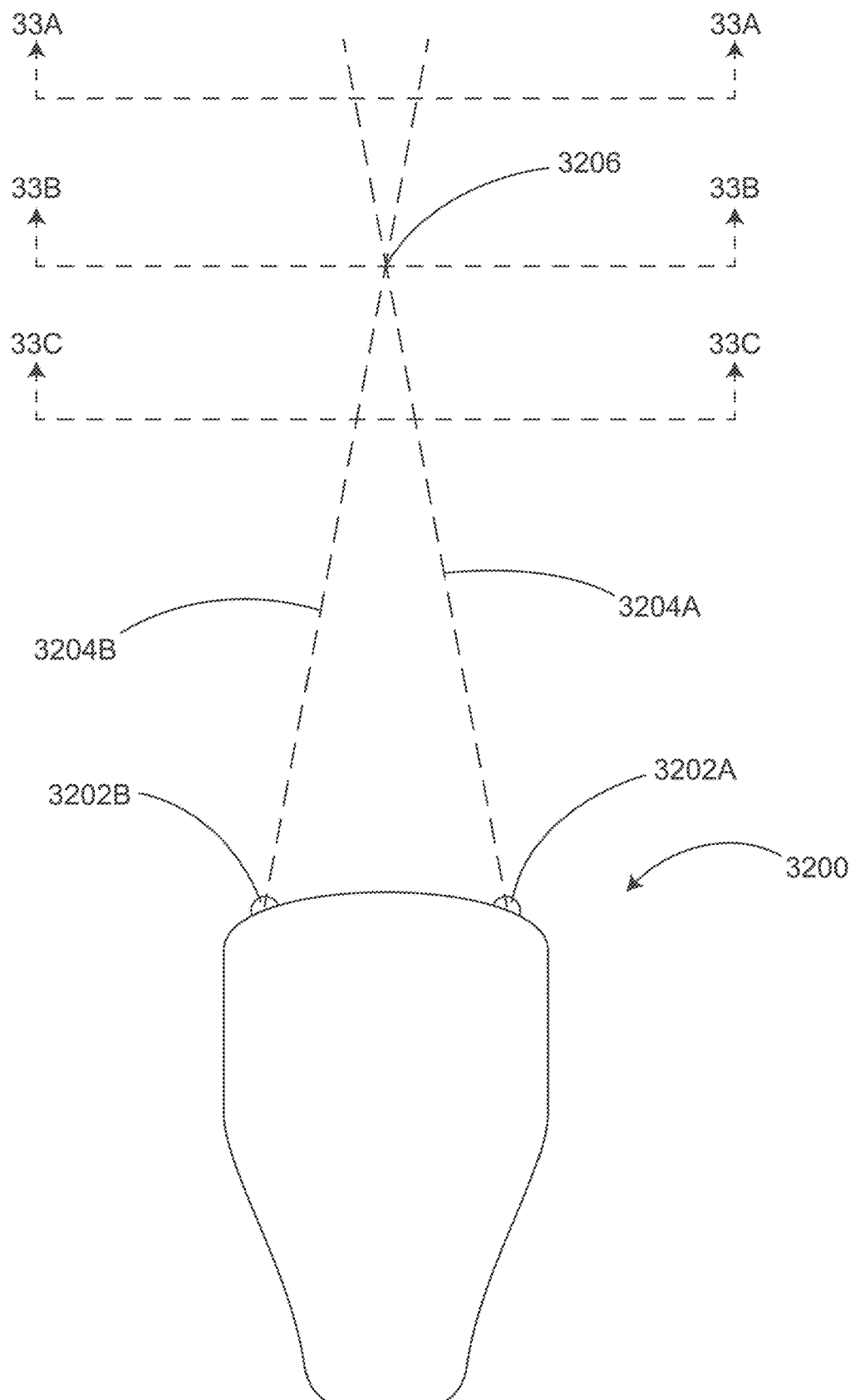
FIG. 32 illustrates a top view of an example of a portable digital camera, in accordance with at least one example of this disclosure.
Figure 33A:
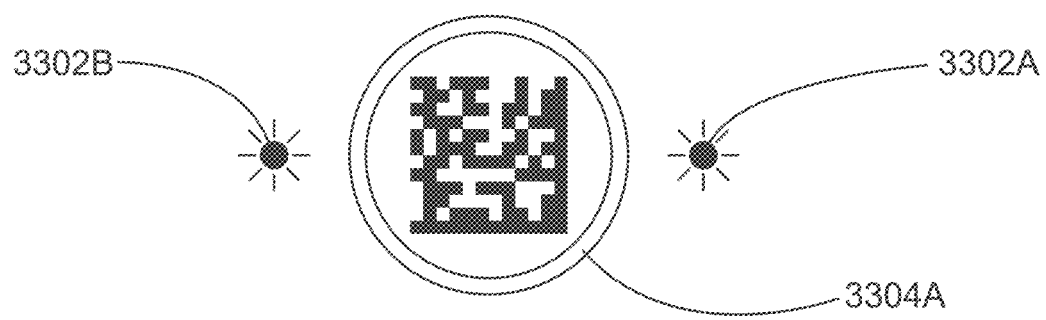
FIGS. 33A-C illustrates targets and QR codes that can be applied to the items or devices to be recorded, in accordance with at least one example of this disclosure.
Figure 33B:
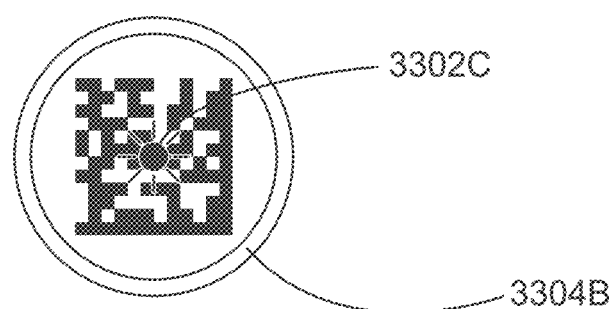
Figure 33C:
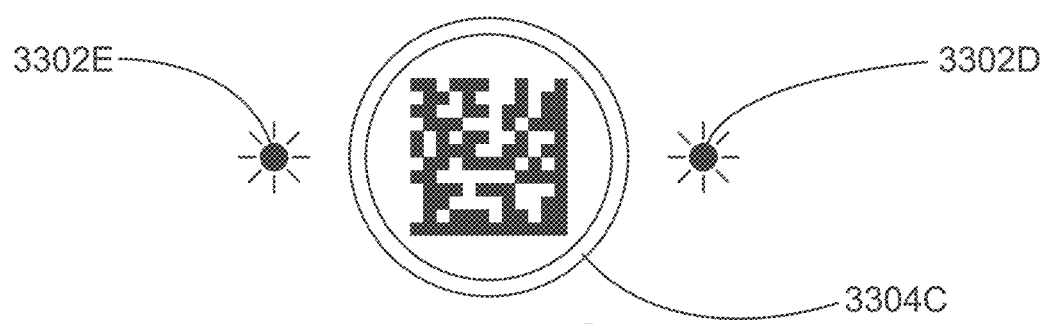

In some examples as shown in a top view in FIG. 32, if the distance of the handheld digital camera 3200 from the subject is important for accurate image recognition or distance or movement measurements by the ML or machine vision software, two laser pointers 3202AB may be used. The laser pointers 3202AB may be mounted on opposite sides of the handheld camera 3200, separated from each other by one or more inches. The pointers are aimed inward to form a triangle with the two beams 3204AB crossing at a prescribed point 3206 in front of the camera, for example, two feet ahead of the camera. Therefore, when the handheld camera 3200 is aimed at the QR code target, if only one point of laser light 3206 is seen, the target is at the crossover distance which is the preferred distance. As shown in FIGS. 33A-C, if two points of light 3302ABDE are visible near the target 3304AC (FIGS. 33A and 33C), the camera needs to be moved either toward or away from the target 3304AC until the two points of light merge into a single point of light 3302C (FIG. 33B) at the target 3304B. The two laser beams may be used to triangulate a preferred distance for the digital video or machine vision image. Similarly, if machine vision is being used to determine the size of an object-a pill for example, the two laser beams may be used to triangulate a preferred distance for the digital camera from the object because the distance of the digital camera from the object is critical when measuring or calculating the object's size with machine vision.

While this disclosure has referred to handheld digital cameras 2800, it should be noted that all portable digital cameras are anticipated. For example, a portable digital camera may be mounted on the users' glasses, or head band or cap or helmet or clothing. Any of these portable digital cameras may deliver the images of this disclosure. In some examples, the portable digital camera may be temporarily fixed in position, mounted to an IV poll for example, in order to record a scene. The portable cameras may be in wired or wireless communication with the processing circuitry of the module.

In some examples, response events may also be documented with the handheld digital cameras 2800 of this disclosure. Including but not limited to many vital signs monitors such as pulse oximeters and automatic blood pressure machines, are free standing entities that do not produce a data output that can be recorded. Thus the data that they display to the user must be manually recorded. In some examples, the handheld digital cameras 2800 of this disclosure can be used to automatically record the data displayed on the vital signs monitors or other physiologic measurement instruments.

In some examples, dose events that may be documented by the handheld digital camera 2800, the processing circuitry and ML or machine vision software of the module of this disclosure include but are not limited to: oral medications, IV medications, patient positioning and movement, volatile anesthetics, ventilator settings, inspired gasses, airway management (ie. intubation, mask ventilation), pneumoperitoneum insufflation pressures, patient warming parameters, surgical table Trendelenburg angles, train-of-four stimulation, nursing activities, surgery, procedures such as IV canulation and feeding.

In some examples, response events that may be documented by the handheld digital camera 2800, the processing circuitry and ML or machine vision software of the module of this disclosure include but are not limited to: legacy vital signs monitor reporting, remote photoplethysmography, skin color changes, airway pressures, urine output surgical blood loss, chest tube output and train-of-four response.

In some examples, equipment operating settings that may be documented by the handheld digital camera 2800, the processing circuitry and ML or machine vision software of the module of this disclosure include but are not limited to: electrosurgical unit (ESU) settings, OR table positioning, pneumoperitoneum insufflation, sequential compression leggings, smoke evacuator settings, UV disinfection documentation, Archimedes air mattress, surgical sponge count, maximum skin support pressures and bed positioning.

As previously discussed in this disclosure, the current standard for patient monitor display location in the anesthesia space in the operating room is beside or behind the anesthesia provider. This is a poor design because a monitor alert (whether real or erroneous) focuses the anesthesia providers attention away from the patient. In some examples, it may be useful to use the design of an airplane cockpit as an example—the windshield and instruments are all in front of the pilot. During WWII it was realized that even looking down at the instruments very briefly could be distracting, so the early "head-up displays" (HUD) were developed to move the instrument information up and into the view out of the windshield. The origin of the name "head-up displays" stems from a pilot being able to view information with the head positioned "up" and looking forward, instead of angled down looking at instruments below the windshield. In some examples, the HUD of this disclosure would project data and waveforms from the physiologic monitors along with other important data and messaging to the space directly above the patient's head, neck or chest for easy, convenient and distraction-free viewing by the anesthesia provider.

Since WWI, HUDs have been developed for many airplanes and cars. HUDs typically consist of three components: a control module that produces the image and determines how the image should be projected; a projector unit which is typically an LED or LCD display/projector; and a combiner, which is the surface onto which the image is projected (generally a coated windshield glass or retractable glass screen above the dashboard). The transparent combiner is necessary in order to see through the projected information while viewing the scene ahead of the plane or car.

In some examples, it is advantageous to place the monitor displays as close to the patient's head as possible so that the monitor and the patient can be viewed in the same field-of-vision. In some examples as shown in FIG. 12, the module 1200 may be used to mount monitor display 226 in a position directly above the patient's 202 head. In this case, module 1200 is advantageously located adjacent the patient 202 and therefore is in an ideal location for mounting monitor display 226. In some examples as shown in FIG. 13, the module 1300 may be used to mount monitor display 326 in a position adjacent the patient's 302 head. In this case, module 1300 is advantageously located adjacent the patient 202 and therefore is in an ideal location for mounting monitor display 326.

Unlike the HUD in a plane or car, there is little need to see "through" the projected information while viewing the patient. Therefore, in some examples it may be advantageous to project the information onto a projection screen above the patient's head or even the vertical anesthesia screen portion of the surgical drape above the patient's head. Unlike the HUD in a plane or car, mounting a rigid sheet of glass or plastic directly above the patient's head may encumber the anesthesiologist during procedures such as induction or emergence from anesthesia, intubation, or even CPR. Therefore, in some examples it may be advantageous to project the information onto a flexible projection screen or flexible sheet of plastic that can easily be moved out of the way if it is in the way of the anesthesiologist doing his or her work.

Unlike the HUD in a plane or car, where the projector is below the combiner aiming upward, placing a projector directly in front of the patient's face will inevitably be in the way. Therefore, in some examples it may be advantageous to project the information onto a projection screen or flexible sheet of plastic, from above or from the sides of the projection screen or flexible sheet of plastic.

Figure 34:
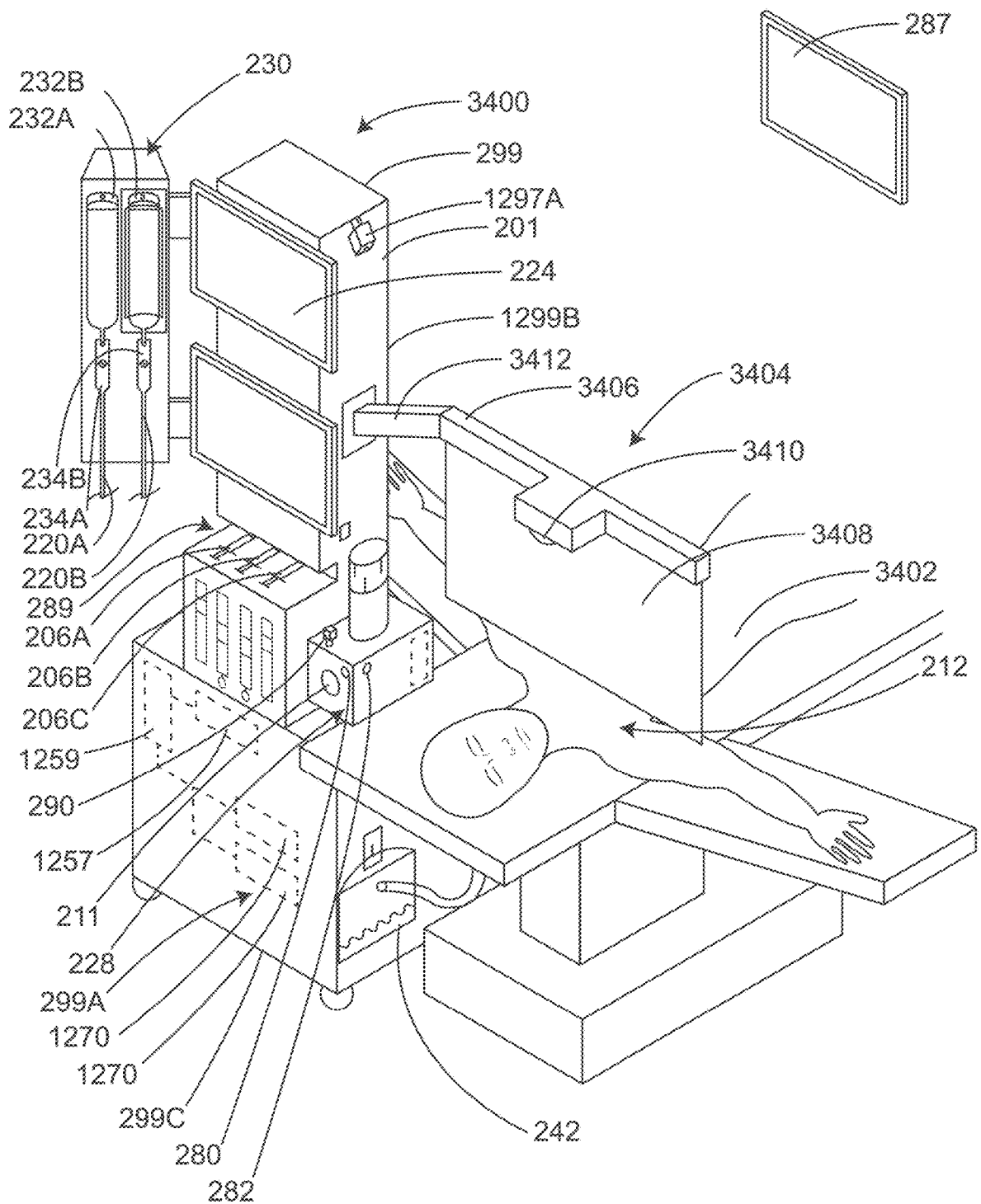
FIG. 34 illustrates a perspective view of an example of a head-up display (HUD), in accordance with at least one example of this disclosure.
Figure 35:
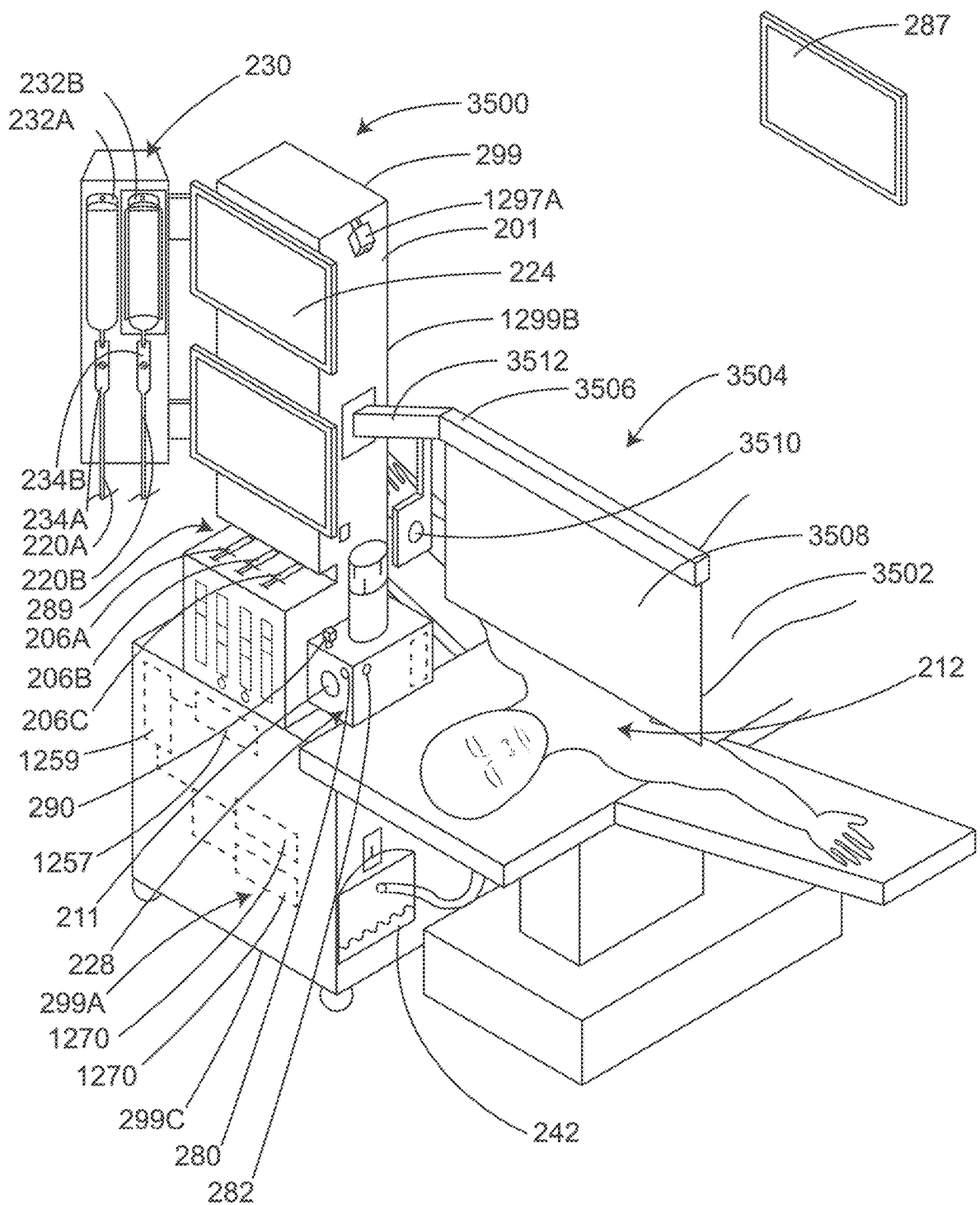
FIG. 35 illustrates a perspective view of an example of a head-up display (HUD), in accordance with at least one example of this disclosure.

In some examples as shown in FIGS. 34 and 35, a HUD 3404 and 3504 may be substituted for the flat screen display 226 shown in FIG. 12. In some examples as shown in FIGS. 34 and 35, HUDs 3404, 3504 may be mounted to modules 3400, 3500 and positioned over the patient's head or neck or chest so that the combiners 3408, 3508 can be viewed in the same field of vision as the patient's head.

In some examples, the HUDs 3404, 3504 may include a support member 3406, 3506 that can support a flexible combiner 3408, 3508 and maintain the flexible combiner 3408, 3508 in a predetermined shape such as flat or curved. In order to prevent the combiner 3408, 3508 from injuring the patient 3402, 3502 or preventing the anesthesiologist from caring for the patient 3402, 3502, the combiner 3408, 3508 may be made of a flexible material including but not limited to plastic film, coated plastic film, fabric, coated fabric, foam or combinations of these materials. The combiners 3408, 3508 may be made of clear or opaque materials. Various coatings that have been developed for automotive HUDs or projection screens, may be utilized to better reflect the images, making them more visible. Rigid combiners 3408, 3508 made of plastic or glass are also anticipated. It is also anticipated that the anesthesia screen can be used as a combiner.

In some examples, the support members 3406, 3506 are adjustably mounted to modules 3400, 3500 through a second support member 3412, 3512 and one or more hinges. Support members 3406, 3506, 3412, 3512 of many sizes, shapes and adjustable constructions are anticipated.

In some examples, the HUDs 3404, 3504 may include one or more projector units 3410, 3510. In some examples, the projector units 3410, 3510 are light emitting diode (LED) or liquid crystal display (LCD) displays/projectors. Other types of projectors are anticipated. In some examples as shown in FIG. 34, the projector unit 3410 may be mounted above the combiner 3408, shining downward on to the combiner 3408. In some examples as shown in FIG. 35, the projector unit 3510 may be mounted at the side of the combiner 3508, shining laterally on to the combiner 3508. It is also anticipated that the projector unit could be mounted next to the patient's head, shining upward on to the combiners 3408, 3508 or could be mounted behind the combiners 3408, 3508, shining at the back side of a transparent combiner 3408, 3508.

In some examples, the processing circuitry of modules 3400, 3500 provide the image data to the projector units 3410, 3510.

Figure 36:
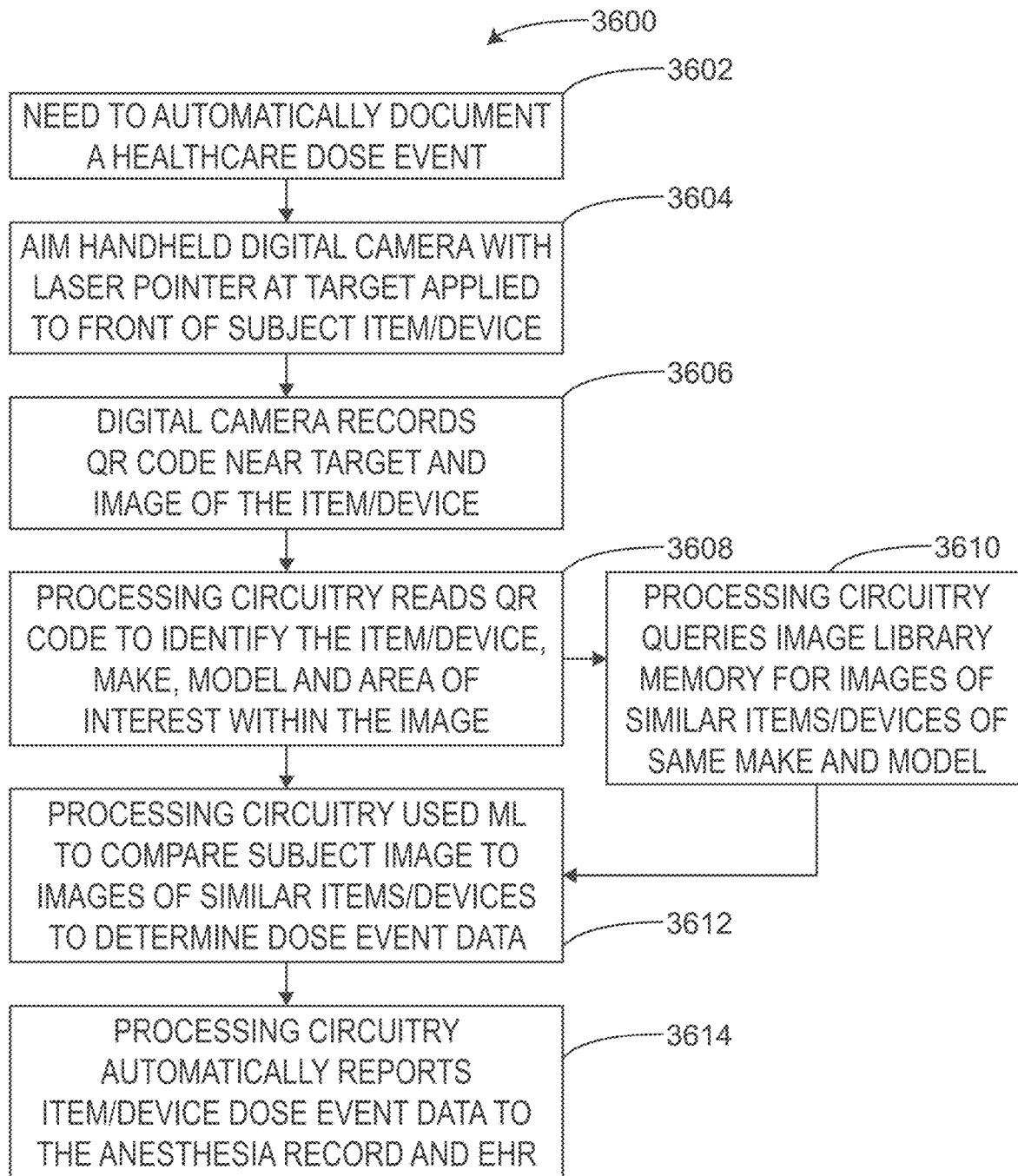
FIG. 36 is a flow chart illustrating a technique or process 3600 for documenting dose events with a portable digital camera, in accordance with at least one example of this disclosure.

FIG. 36 is a flow chart illustrating a process 3600 for automatically recording dose events using a portable digital camera 2800 and processing circuitry, such as, but not limited to, processing circuitry 157, FIG. 1; 257, FIG. 2; 1502, FIG. 15. FIG. 36 illustrates generally an example of a block diagram of process 3600 for automatically recording dose events using a portable digital camera 2800.

In some examples, the process for automatically recording dose events starts at 3602 when the healthcare provider desires to automatically record and document a healthcare dose event such as changing the concentration of an anesthetic gas produced by the item or device, anesthetic vaporizer 2900, 3000 for example. In some examples, in operation 3604, a handheld digital camera 2800 is equipped with a laser pointer 2806 and the laser pointer 2806 is aimed at a target 2902, 3006, 3106 or icon attached to the item or device 2900, 3000 in a prescribed location. In some examples, the target 2902, 3006, 3106 is attached to the front of the item/device 2900, 3000 to "standardize the scene" or standardize the viewing angle of the camera relative to the item/device 2900, 3000.

In some examples in operation 3606, when the laser pointer 2806 is correctly aimed at the target 2902, 3006, 3106 the trigger is pulled and the handheld digital camera 2800 simultaneously records both a QR code 2904, 3004, 3104 (or other coding technology) attached to the item or device 2900, 3000 near or within the target 2902, 3006, 3106 and an image of the item/device 2900, 3000.

In some examples in operation 3608, the processing circuitry processes the data from the digital camera 2800, first reading the QR code 2904, 3004, 3104 to identify the specific type of item/device 2900, 3000, 3100 the make and the model. In some examples, the processing circuitry and memory include information on the specific area of interest 2910, 3008, 3112 for that item/device 2900, 3000, 3100. For example, the area of interest 2910 for vaporizer 2900 is the concentration dial 3002 at the top of the vaporizer 2900. Since the metal can is of little interest, the ML software may be programed to focus on the area of interest 2910, ignoring the rest of the item/device 2900.

In some examples in operation 3610, the processing circuitry uses the information from the QR code 3004 to query an image library stored in the memory. Rather than comparing the image of the subject item/device 3000A to every image in the library, the query can be focused on only images of items/devices 3000B-D identical to the subject item/device 3000A and those images of identical items/devices 3000B-D may be stored together in a labeled file in the memory for easy access. This reduces the inquiry/comparison of images by many orders of magnitude, both speeding the process and improving accuracy.

In some examples in operation 3612, the processing circuitry uses ML techniques to compare the image of the subject item/device 3000A, to images in the image library of items/devices 3000B-D identical to the subject item/device 3000A. The different images of items/devices 3000B-D in the image library may be identical except for the control dial 3002B-D being photographed at the various possible settings throughout the entire range. When the processing circuitry successfully matches the image of the control dial 3002A of the subject item/device 3000A with the image of the control dial 3002C of a known item/device 3000C in the image library, the numerical setting on the control dial 3002A of the subject item/device 3000A can assumed to equal the known numerical setting of the known item/device 3000C in the image library.

In some examples in operation 3614, the processing circuitry takes the numerical setting or numerical dose event and automatically adds a time-stamp to the dose event data. The processing circuitry then reports the time-stamped dose event data from the subject item/device 3000A to at least one of the EAR, EMR, EHR or database in the cloud.

Any operations of the various methods described herein can be used in combination with or separately from one another, depending on the desired features and in consideration of constraints such as financial, space, material and manufacturing availability.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects. The terms approximately, about or substantially are defined herein as being within 10% of the stated value or arrangement.

The above description is intended to be illustrative, and not restrictive. For example, the above-described examples (or one or more aspects thereof) may be used in combination with each other. Other examples can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed example. Thus, the following claims are hereby incorporated into the Detailed Description as examples or examples, with each claim standing on its own as a separate example, and it is contemplated that such examples can be combined with each other in various combinations or permutations. The scope of the invention should be determined with reference to the appended claims, along with the full scope of equivalents to which such claims are entitled.

Notes and Various Examples

Each of these non-limiting examples may stand on its own, or may be combined in various permutations or combinations with one or more of the other examples. The examples are supported by the preceding written description as well as the drawings of this disclosure.

Example 1 is a system for intravenous (IV) medications to deliver a medication from a syringe, the system comprising: a provider identification sensor configured to identify (e.g., sense) provider identification information; an injection portal configured to receive the syringe; one or more medication sensors configured to identify medication identification information that is coupled to the received syringe when the received syringe is located in the injection portal and configured to capture an image of the received syringe; one or more displays; one or more storage devices; and processing circuitry that is in electrical communication with the provider identification sensor, the one or more medication sensors, the one or more displays and the one or more storage devices, wherein the processing circuitry is configured to receive the provider identification information and to store the provider identification to at least one of the one or more storage devices, wherein the processing circuitry is configured to send instructions to at least one of the one or more displays to output a visual image or representation of the received syringe on the at least one display, wherein the processing circuitry is configured to determine a volume of medication dispensed from the received syringe based on an image of the syringe captured by the one or more medication sensors, and wherein the processing circuitry is configured to at least one of: save the volume of medication dispensed to the one or more storage devices or send instructions to at least one of the one or more displays to output the volume of medication dispensed on the at least one display.

In Example 2, the subject matter of Example 1 includes, wherein the injection portal further comprises: an injection port that is configured to fluidly couple to IV tubing; and at least one orienting member configured to guide the received syringe having a diameter that is a first diameter of a plurality of different diameters, to mate with the injection port.

In Example 3, the subject matter of Examples 1-2 includes, wherein at least one of the one or more medications sensors is located to capture an image of an inside of the injection portal, and wherein the processing circuitry is configured to receive a captured image of the received syringe and to calculate the volume of medication dispensed from the received syringe from the captured image by determining an internal diameter of the syringe and measuring a distance a plunger of the received syringe moves to calculate an injected volume.

In Example 4, the subject matter of Examples 1-3 includes, wherein at least one of the one or more medication sensors is an RFID interrogator, and wherein the medication identification information is an RFID tag.

In Example 5, the subject matter of Examples 1-4 includes, wherein at least one of the one or more medication sensors is configured to read the medication identification information and transmit a medication identity to the processing circuitry.

In Example 6, the subject matter of Examples 1-5 includes, wherein at least one of the one or more medication sensors is a machine vision digital camera.

In Example 7, the subject matter of Examples 1-6 includes, wherein when the provider identification sensor is configured to read the provider identification information and to generate provider identification data, and wherein the processing circuitry is configured to receive the generated provider identification information and to compare the generated provider identification information to withdrawing provider information, wherein the withdrawing provider information includes an identity of the provider who withdrew the syringe from a vending source.

In Example 8, the subject matter of Example 7 includes, wherein the provider identification sensor is a barcode reader, an RFID interrogator, a retinal scanner, a facial recognition scanner, or a fingerprint reader.

In Example 9, the subject matter of Examples 1-8 includes, wherein the processing circuitry is configured to send instructions to at least one of the one or more displays to output one or more of: a brand name of a drug, a generic name of a drug, a drug concentration, a dosage of a drug, a dosage delivered, a fluid flow rate, a fluid volume delivered, a patient allergy, an over-dosing alert, a drug allergy alert and a drug interaction alert.

In Example 10, the subject matter of Examples 1-9 includes, wherein the processing circuitry is configured to transmit dispensing information to one or more of: an electronic anesthetic record (EAR) and an electronic medical record (EMR), to automatically record dispensing information about the medication dispensed from the received syringe to the EAR or the EMR.

In Example 11, the subject matter of Examples 1-10 includes, an injection port located in the injection portal that is configured to fluidly couple the received syringe to IV tubing; and at least one clamp in electrical communication with the processing circuitry, wherein the processing circuitry is configured send an instruction to actuate the at least one clamp positioned one or more of upstream or downstream from the injection port, and wherein the processing circuitry is configured to send instructions to the at least one clamp to inhibit dispensing of the medication or an IV fluid when an adverse condition is determined by the processing circuitry.

Example 12 is a system for intravenous (IV) medications to deliver a medication from a syringe, the system comprising: a provider identification sensor configured to identify (e.g., sense) a provider; an injection portal configured to receive the syringe; one or more medication sensors configured to identify medication information that is coupled to the received syringe when the received syringe is located in the injection portal, wherein at least one of the one or more medication sensors is located to capture an image of an inside of the injection portal; one or more displays; one or more storage devices; and processing circuitry that is in electrical communication with the provider identification sensor, the one or more medication sensors, the one or more displays, and the one or more storage devices, wherein the processing circuitry is configured to receive the provider identification information and to store the provider identification to at least one of the one or more storage devices, wherein the processing circuitry is configured to send instructions to at least one of the one or more displays to output a visual image or representation of the received syringe on the at least one display, wherein the processing circuitry is configured to receive a captured image of the received syringe and to calculate a volume of medication dispensed from the received syringe from the captured image by determining an internal diameter of the syringe and measuring a distance a plunger of the received syringe moves to calculate an injected volume, and wherein the processing circuitry is configured to at least one of: save the volume of medication dispensed to the one or more storage devices or send instructions to at least one of the one or more displays to output the volume of medication dispensed on the at least one display.

In Example 13, the subject matter of Example 12 includes, wherein the injection portal further comprises: an injection port that is configured to fluidly couple to IV tubing; and at least one orienting member configured to guide the received syringe having a diameter that is a first diameter of a plurality of different diameters, to mate with the injection port.

In Example 14, the subject matter of Examples 12-13 includes, wherein at least one of the one or more medication sensors is an RFID interrogator, and wherein the medication identification information is an RFID tag.

In Example 15, the subject matter of Examples 12-14 includes, wherein at least one of the one or more medication sensors is configured to read the medication identification information and transmit a medication identity to the processing circuitry.

In Example 16, the subject matter of Examples 12-15 includes, wherein the processing circuitry is configured to send instructions to at least one of the one or more displays to output one or more of: a brand name of a drug, a generic name of a drug, a drug concentration, a dosage of a drug, a dosage delivered, a fluid flow rate, a fluid volume delivered, a patient allergy, an over-dosing alert, a drug allergy alert and a drug interaction alert.

In Example 17, the subject matter of Examples 12-16 includes, wherein the processing circuitry is configured to transmit dispensing information to one or more of: an electronic anesthetic record (EAR) and an electronic medical record (EMR), to automatically record dispensing information about the medication dispensed from the received syringe to the EAR or the EMR.

In Example 18, the subject matter of Examples 12-17 includes, an injection port located in the injection portal that is configured to fluidly couple the received syringe to IV tubing; and at least one clamp in electrical communication with the processing circuitry, wherein the processing circuitry is configured send an instruction to actuate the at least one clamp positioned one or more of upstream or downstream from the injection port, and wherein the processing circuitry is configured to send instructions to the at least one clamp to inhibit dispensing of the medication or an IV fluid when an adverse condition is determined by the processing circuitry.

Example 19 is a system for delivering intravenous (IV) fluids from an IV bag fluidly that is coupled to a drip chamber and IV tubing, the system comprising: an IV scale configured to receive and support the IV bag; one or more sensors, wherein at least one of the one or more sensors is configured to identify an IV fluid in the IV bag hanging on the IV scale and wherein at least one of the one or more sensors is located adjacent to the received drip chamber and is configured to capture an image of the drip chamber; one or more displays; one or more storage devices; and processing circuitry that is in electrical communication with the IV scale, the one or more sensors, the one or more displays and the one or more storage devices, wherein the processing circuitry is configured to receive a medication identity and a captured image of the drip chamber from the one or more sensors, and wherein the processing circuitry is configured to determine a fluid flow rate by analyzing an image of fluid drops falling in the drip chamber including determining a size of drops and a number of drops per unit time; wherein the processing circuitry is configured to at least one of: save the fluid flow rate to one or more storage devices or send instructions to at least one of the one or more displays to output the fluid flow rate on at least one of the one or more displays.

In Example 20, the subject matter of Example 27 includes, wherein the IV scale includes a hanger configured to support the IV bag, and wherein the IV scale is configured to measure a combined weight of the IV bag, the IV drip chamber, the IV tubing and the fluids in the IV bag, and wherein the processing circuitry is configured to determine a reduction in a measured combined weight over time to determine a weight of the fluid removed from the IV bag and to convert the measured combined weight over time to a fluid flow rate and an infused fluid volume.

In Example 21, the subject matter of Examples 27-28 includes, a float located in the IV drip chamber, wherein when the processing circuitry determines from the captured image that the fluid drops in the drip chamber cannot be distinguished from one another and that the float is moving, the processing circuitry is configured to measure the fluid flow rate by determining a reduction of a combined weight of the IV bag, the IV drip chamber, the IV tubing and fluid in the IV bag over time.

In Example 22, the subject matter of Examples 19-22 includes, one or more electromechanical clamps that is in electrical communication with the processing circuitry, wherein the processing circuitry is configured to determine from the captured image that no fluid meniscus is present in the drip chamber, the processing circuitry sends an instruction to cause at least one of the one or more electromechanical clamps to compress the IV tubing to inhibit fluid flow prior to air entering the IV tubing.

Example 23 is at least one machine-readable medium including instructions that, when executed by processing circuitry, cause the processing circuitry to perform operations to implement of any of Examples 1-30.

Example 24 is an apparatus comprising means to implement of any of Examples 1-23.

Example 25 is a system to implement of any of Examples 1-23.

Example 26 is a method to implement of any of Examples 1-23.

What is claimed is:

1. An automated data consolidation module including a system to receive and record data produced by medical equipment, the automated data consolidation module comprising:
   a module;
   at least one digital camera configured to produce digital data; and
   processing circuitry in wired or wireless electrical communication with the at least one digital camera to receive the digital data, wherein the digital data is automatically delivered to the processing circuitry and software, and wherein the processing circuitry and software is configured to interpret the digital data by performing at least one of machine learning (ML) and artificial intelligence (AI) analysis to:
      identify specific visual elements of an image of the digital data by matching a subject image of the digital data to known images stored in an image library, to create matched identified specific visual elements of the image that show an operating parameter of a medical item or device performing a dose event or the specific visual elements of an image that show a measurement of a response event;
      add time stamps or other indicators of time to the identified specific visual elements so that the digital data can be temporally correlated during subsequent big data or clinical decision support analysis; and
      automatically save information provided by the matched identified specific visual elements of the image or the image itself to an electronic record or database;
   wherein the at least one digital camera, processing circuitry and software are configured to photograph, analyze, and record an identifier including at least one of a quick response (QR) code, a barcode, or other identifier that is attached to a medical item or device, and wherein the QR code, barcode, or other identifier identifies at least one of a type of item or device, a manufacturer of the item or device, a model of the item or device, and a content of the item or device, narrowing the ML or AI analysis by directing the ML or AI analysis to a folder containing images of a specific type, manufacturer, model, or content of the item or device associated with the identifier.

2. The automated data consolidation module of claim 1, wherein the QR code, barcode, or other identifier is attached to a subject medical item or device in a prescribed location on the medical item or device relative to the specific visual elements to be identified and the prescribed location of the QR code, barcode, or other identifier becomes a target for a laser pointer to standardize a scene and to orient the at least one digital camera to match similarly structured scenes and camera orientations of the known images stored in an image library.

3. The automated data consolidation module of claim 1, wherein the QR code, barcode, or other identifier identifies an area or areas of interest within a scene so that the ML or AI analysis can focus on the area or areas of interest on the medical item or device that show desired information.

4. The automated data consolidation module of claim 1, wherein the at least one digital camera, processing circuitry, and software includes machine vision capabilities for one or more of:
   pill identification, pill counting, or observation of and verification of a patient taking pills.

5. The automated data consolidation module of claim 1, wherein the medical item or device performing a dose event is a syringe and the quick response (QR) code, barcode, or other identifier that is attached to the medical item or device identifies at least a content of the syringe.

6. The automated data consolidation module of claim 1, wherein the medical item or device performing a dose event is a IV bag and drip set and the quick response (QR) code, barcode, or other identifier that is attached to the medical item or device identifies at least a content of the IV bag and drip set.

7. The automated data consolidation module of claim 1, wherein the medical item or device performing a dose event is a drug infusion pump and the quick response (QR) code, barcode, or other identifier that is attached to the medical item or device identifies at least a content of the drug infusion pump.

8. The automated data consolidation module of claim 1, wherein the medical item or device performing a dose event is an anesthetic vaporizer and the quick response (QR) code, barcode, or other identifier that is attached to the medical item or device identifies at least a content of the anesthetic vaporizer.

9. The automated data consolidation module of claim 1, wherein the medical item or device performing a dose event is a gas supply and the quick response (QR) code, barcode, or other identifier that is attached to the medical item or device identifies at least a content of the gas supply.

10. The automated data consolidation module of claim 1, wherein the identified specific visual elements of the image constitute dose events or response events and the processing circuitry is configured to add time stamps or other indicators of time so that unrelated data can be temporally correlated during subsequent "big data" analysis.

11. The automated data consolidation module of claim 1, wherein the processing circuitry includes artificial intelligence or machine learning algorithms that compare the response event to the dose event and provide immediate feedback via a display or alert device.

12. The automated data consolidation module of claim 1, wherein the electronic record or database is configured to be accessed by artificial intelligence or machine learning algorithms to retrieve one or more temporally correlated dose-response event and compare the one or more temporally correlated dose-response event to other temporally correlated dose-response events across a population of patients and output big data correlation insights to at least one storage device or display.

13. The automated data consolidation module of claim 1, wherein the processing circuitry and software can temporally correlate the dose event and the response event and artificial intelligence (AI) analytics can identify expected and unexpected physiologic responses to a given dose event.

14. An automated data consolidation module including a digital camera comprising:
a module;
at least one digital camera; and
processing circuitry in wired or wireless electrical communication with the at least one digital camera to receive and record digital data produced by the at least one digital camera, wherein the at least one digital camera and the processing circuitry and software are configured to photograph, analyze, and record an identifier including at least one of a QR code, a barcode or other identifier that is attached to a medical item or device, the QR code, barcode, or other identifier identifying at least one of a type of the medical item or device, a manufacturer of the medical item or device, a model of the medical item or device, and a content of a medical item or device;
wherein the digital data from the at least one digital camera includes an image of the medical item or device that is automatically delivered to the processing circuitry and software, and wherein the processing circuitry and software are configured to perform at least one of machine learning (ML) and artificial intelligence (AI) analysis to:
identify specific visual elements of the image by matching the image to known images stored in an image library to form matched specific visual elements of the image that show an operating parameter of a medical item or device performing a dose event or the specific visual elements of an image that show a measurement of a response event; and
automatically save information provided by the matched specific visual elements of the image or the image itself to an electronic record or database; and
wherein the QR code, barcode, or other identifier that is attached to the medical item or device narrows the ML and AI image analysis by directing a search of the ML or AI analysis to a folder containing images of the type, manufacturer, model, or content of the medical item or device.

15. The automated data consolidation module of claim 14, wherein the QR code, barcode, or other identifier is attached to a subject medical item or device in a prescribed location on the medical item or device relative to the specific visual elements to be identified and the prescribed location of the QR code, barcode, or other identifier becomes a target for a laser pointer to standardize a scene and to orient the at least one digital camera to match similarly structured scenes and camera orientations of the known images stored in an image library.

16. The automated data consolidation module of claim 14, wherein the QR code, barcode, or other identifier identifies an area or areas of interest within a scene so that the ML or AI analysis can focus on the area or areas of interest on the medical item or device that show desired information.

17. The automated data consolidation module of claim 14, wherein the at least one digital camera, processing circuitry, and software includes machine vision capabilities for one or more of:
pill identification, pill counting, or observation of and verification of a patient taking pills.

18. The automated data consolidation module of claim 14, wherein the medical item or device performing a dose event is a syringe and the QR code, barcode, or other identifier that is attached to the medical item or device identifies at least a content of the syringe.

19. The automated data consolidation module of claim 14, wherein the medical item or device performing a dose event is a IV bag and drip set and the QR code, barcode, or other identifier that is attached to the medical item or device identifies at least a content of the IV bag and drip set.

20. The automated data consolidation module of claim 14, wherein the medical item or device performing a dose event is a drug infusion pump and the QR code, barcode, or other identifier that is attached to the medical item or device identifies at least a content of the drug infusion pump.

21. The automated data consolidation module of claim 14, wherein the medical item or device performing a dose event is a anesthetic vaporizer and the QR code, barcode, or other identifier that is attached to the medical item or device identifies at least a content of the anesthetic vaporizer.

22. The automated data consolidation module of claim 14, wherein the medical item or device performing a dose event is a gas supply and the QR code, barcode, or other identifier that is attached to the medical item or device identifies at least a content of the gas supply.

23. The automated data consolidation module of claim 14, wherein the identified specific visual elements of the image constitute the dose events or the response event and the processing circuitry is configured to add time stamps or other indicators of time so that unrelated data can be temporally correlated during subsequent "big data" analysis.

24. The automated data consolidation module of claim 14, wherein the processing circuitry includes artificial intelligence or machine learning algorithms that compare the response event to the dose event and provide immediate feedback via a display or alert device.

25. The automated data consolidation module of claim 14, wherein the electronic record or database is configured to be accessed by artificial intelligence or machine learning algorithms to retrieve one or more temporally correlated dose-response event and compare the one or more temporally correlated dose-response events to other temporally correlated dose-response events across a population of patients and output big data correlation insights to at least one storage device or display.

26. The automated data consolidation module of claim 14, wherein the processing circuitry and software can temporally correlate the dose event and the response event and artificial intelligence (AI) analytics can identify expected and unexpected physiologic responses to a given dose event.

27. An automated data consolidation module including a digital camera comprising:
a module;
at least one digital camera; and
processing circuitry in wired or wireless electrical communication with the at least one digital camera to receive and record digital data produced by the at least one digital camera, wherein the at least one digital camera and the processing circuitry and software are configured to photograph, analyze, and record an identifier including at least one of a QR code, a barcode or other identifier that is attached to a medical item or device, the QR code, barcode, or other identifier identifying at least one of a type of the medical item or device, a manufacturer of the medical item or device, a model of the medical item or device, and a content of a medical item or device;

wherein the digital data from the at least one digital camera includes an image of the medical item or device that is automatically delivered to the processing circuitry and software, and wherein the processing circuitry and software are configured to perform at least one of machine learning (ML) and artificial intelligence (AI) analysis to:

identify specific visual elements of the image by matching the image to known images stored in an image library to form matched specific visual elements of the image that show an operating parameter of a medical item or device performing one or more dose event or the specific visual elements of an image that show a measurement of one or more response event; and automatically save information provided by the matched specific visual elements of the image or the image itself to an electronic record or database;

wherein the QR code, barcode, or other identifier that is attached to the medical item or device narrows the ML and AI image analysis by directing a search of the analysis to a folder containing images of the type, manufacturer, model, or content of the medical item or device; and wherein the QR code, barcode, or other identifier is attached to a subject medical item or device in a prescribed location on the medical item or device relative to the specific visual elements to be identified and the prescribed location of the QR code, barcode, or other identifier becomes a target for a laser pointer to standardize a scene and to orient the at least one digital camera to match similarly structured scenes and camera orientations of the known images stored in an image library.

28. The automated data consolidation module of claim 27, wherein the QR code, barcode, or other identifier identifies an area or areas of interest within a scene so that the ML or AI analysis can focus on the area or areas of interest on the medical item or device that show desired information.

29. The automated data consolidation module of claim 27, wherein the at least one digital camera, processing circuitry, and software includes machine vision capabilities for one or more of:

pill identification, pill counting, or observation of and verification of a patient taking pills.

30. The automated data consolidation module of claim 27, wherein the medical item or device performing the one or more dose event is a syringe and the QR code, barcode, or other identifier that is attached to the medical item or device identifies at least a content of the syringe.

31. The automated data consolidation module of claim 27, wherein the medical item or device performing the one or more dose event is a IV bag and drip set and the QR code, barcode, or other identifier that is attached to the medical item or device identifies at least a content of the IV bag and drip set.

32. The automated data consolidation module of claim 27, wherein the medical item or device performing the one or more dose event is a drug infusion pump and the QR code, barcode, or other identifier that is attached to the medical item or device identifies at least a content of the drug infusion pump.

33. The automated data consolidation module of claim 27, wherein the medical item or device performing the one or more dose event is a anesthetic vaporizer and the QR code, barcode, or other identifier that is attached to the medical item or device identifies at least a content of the anesthetic vaporizer.

34. The automated data consolidation module of claim 27, wherein the medical item or device performing the one or more dose event is a gas supply and the QR code, barcode, or other identifier that is attached to the medical item or device identifies at least a content of the gas supply.

35. The automated data consolidation module of claim 27, wherein the identified specific visual elements of the image constitute the one or more dose event or the one or more response event and the processing circuitry is configured to add time stamps or other indicators of time so that unrelated data can be temporally correlated during subsequent "big data" analysis.

36. The automated data consolidation module of claim 27, wherein the processing circuitry includes artificial intelligence or machine learning algorithms that compare the one or more response event to the one or more dose event and provide immediate feedback via a display or alert device.

37. The automated data consolidation module of claim 27, wherein the electronic record or database is configured to be accessed by artificial intelligence or machine learning algorithms to retrieve one or more temporally correlated dose-response event and compare the one or more temporally correlated dose-response event to other temporally correlated dose-response events across a population of patients and output big data correlation insights to at least one storage device or display.

38. The automated data consolidation module of claim 27, wherein the processing circuitry and software can temporally correlate the one or more dose event and the one or more response event and artificial intelligence (AI) analytics can identify expected and unexpected physiologic responses to a given dose event.

* * * * *